(12) United States Patent
Skerra et al.

(10) Patent No.: US 7,691,970 B2
(45) Date of Patent: Apr. 6, 2010

(54) MUTEINS OF A BILIN-BINDING PROTEIN WITH AFFINITY FOR A GIVEN TARGET

(75) Inventors: Arne Skerra, Freising (DE); Steffen Schlehuber, Langenbach (DE)

(73) Assignee: Pieris AG, Freising-Weihenstephan (DE)

( * ) Notice: Subject to any disclaimer, the term of this patent is extended or adjusted under 35 U.S.C. 154(b) by 685 days.

(21) Appl. No.: 10/569,133

(22) PCT Filed: Aug. 25, 2003

(86) PCT No.: PCT/EP03/09403

§ 371 (c)(1),
(2), (4) Date: Apr. 28, 2006

(87) PCT Pub. No.: WO2005/019254

PCT Pub. Date: Mar. 3, 2005

(65) Prior Publication Data

US 2007/0148201 A1 Jun. 28, 2007

(51) Int. Cl.
*C07K 14/00* (2006.01)
(52) U.S. Cl. .................................................... 530/350
(58) Field of Classification Search ........................ None
See application file for complete search history.

(56) References Cited

U.S. PATENT DOCUMENTS 5,849,576 A 12/1998 Skerra et al.

FOREIGN PATENT DOCUMENTS

| DE | 44 17 598 A1 | 12/1995 |
|---|---|---|
| EP | 1 270 725 A | 1/2003 |
| WO | WO 99/16873 A1 | 4/1999 |
| WO | WO 00/75308 A1 | 12/2000 |
| WO | WO 03 029471 A | 4/2003 |
| WO | WO 03/029471 A1 | 4/2003 |

OTHER PUBLICATIONS

Sakai et al. J. Insect. Biotechnology, 2001, 70:105-111.*
Appendix A—Result 3 from sequence alignment of Sakiai et al. and wild-type bilin binding protein from *Peiris brassicae.**
Bowie et al., Deciphering the Message in Protein Sequences: Tolerance to Amino Acid Substitutions. Science. 1990. vol. 247, pp. 1306-1310.*
Wells, J.A., Additivity of Mutational Effects in Proteins. Biochemistry. 1990. vol. 29, No. 37, pp. 8509-8517.*
Altschul et al., "Gapped BLAST and PSI-BLAST: a new generation of protein database search programs," Nucleic Acids Research, 1997, vol. 25, No. 17, pp. 3389-3402.

(Continued)

*Primary Examiner*—Suzanne M. Noakes
(74) *Attorney, Agent, or Firm*—Foley & Lardner LLP

(57) ABSTRACT

The present invention relates to novel muteins derived from a bilin-binding protein (BBP) that binds a given target, for example a macromolecular target, with detectable affinity. In particular, the invention relates to a mutein of the bilin-binding protein of *Pieris brassicae*. The invention also refers to a corresponding nucleic acid molecule encoding such a mutein and to a method for its generation. The invention further refers to a method for producing such a mutein. Finally, the invention is directed to a pharmaceutical composition comprising such a lipocalin mutein as well as to various use of the mutein.

26 Claims, 17 Drawing Sheets

OTHER PUBLICATIONS

Amstutz et al., "In vitri display technologies; novel developments and applications," Current Opinion in Biotechnology, Aug. 1, 2001, vol. 12, issue 4, pp. 400-405 (Abstract, one page).

Beste et al., "Small antibody-like proteins with prescribed ligand specificities derived from the lipocalin fold," Proc. Natl. Acad. Sci. USA, Mar. 1999, vol. 96, pp. 1898-1903.

Bullock et al., "XL1-Blue: A High Efficiency Plasmid Transforming recA *Escherichia coli* Strain With Beta-Galactosidase Selection," BioTechniques, 1987, vol. 5, No. 4, pp. 376-378.

Fling et al., "Peptide and protein molecular weight determination by electrophoresis using a high-molarity tris buffer system without urea," Anal Biochem., May 1986, vol. 155, No. 1, pp. 83-88 (Abstract, one page).

Flower, Darren R., "The lipocalin protein family: structure and function," Biochem. J., 1996, vol. 318, pp. 1-14.

Flower et al., "The lipocalin protein family: structural and sequence overview," Biochimica et Biophysica Acta (BBA), Oct. 18, 2000, vol. 1482, issues 1-2, pp. 9-24 (Abstract, two pages).

Hengen, Paul N. "Methods and reagents: Preparing ultra-competent *Escherichia coli*," TIBS, Feb. 1996, vol. 21, pp. 75-76.

Kraulis et al., "The serum albumin-binding domain of streptococcal protein G is a three-helical bundle: a heteronuclear NMR study," FEBS Letters, 1996, vol. 378, pp. 190-194.

Lindberg et al., "Molecular Cloning of Integrin-associated Protein: An Immunoglobulin Family Member with Multiple Membrane-spanning Domains Implicated in $\alpha_v\beta_3$-dependent Ligand Binding," J. Cell Biology, Oct. 1993, vol. 123, No. 2, pp. 485-496.

Lowman, H.B., "Bacteriophage display and discovery of peptide leads for drug development," Annu. Rev. Biophys. Biomol. Struct., 1997, vol. 26, pp. 401-424.

Maddon et al., "The isolation and nucleotide sequence of a cDNA encoding the T cell surface protein T4: a new member of the immunoglobulin gene family," Cell, Aug. 1985, vol. 42, No. 1, pp. 93-104.

Peitsch et al., "Is apolipoprotein D a mammalian bilin-binding protein?", New Biol., Feb. 1990, vol. 2, No. 2, pp. 197-206.

Pervaiz et al., "Homology and structure-function correlations between $\alpha_1$-acid glycoprotein and serum retinol-binding protein and its relatives," FASEB J., 1987, vol. 1, pp. 209-214.

Pini et al., "Phage Display and Colony Filter Screening for High-Throughput Selection of Antibody Libraries," Combinatorial Chemistry & High Throughput Screening, 2002, vol. 5, No. 7, 1 pg (Abstract).

Rodi et al., "Phage-display technology—finding a needle in a vast molecular haystack," Curr. Opin. Biotechnol., Feb. 1999, vol. 10, No. 1, pp. 87-93 (Abstract, one page).

Schlehuber et al., "Duocalins: Engineered Ligand-Binding Proteins with Dual Specificity Derived from the Lipocalin Fold," Biol. Chem., Sep. 2001, vol. 382, pp. 1335-1342.

Schlehuber et al., "A Novel Type of Receptor Protein, Based on the Lipocalin Scaffold, with Specificity for Digoxigenin," J. Mol. Biol., 2000, vol. 297, pp. 1105-1120.

Schmidt et al., "The bilin-binding protein of *Pieris brassicae*. cDNA sequence and regulation of expression reveal distinct features of this insect pigment protein," Eur. J. Biochem., Feb. 1994, vol. 219, No. 3, pp. 855-863 (Abstract, one page).

Schmidt et al., "Molecular Interaction Between the *Strep*-tag Affinity Peptide and its Cognate Target, Streptavidin," J. Mol. Biol., 1996, vol. 255, pp. 753-766.

Skerra et al., "Use of the *Strep*-Tag and Streptavidin for Detection and Purification of Recombinant Proteins," Methods in Enzymology, 2000, vol. 326, pp. 271-304.

Skerra, Arne, "Lipocalins as a scaffold," Biochimica et Biophysica Acta, 2000, vol. 1492, pp. 337-350.

Tung et al., "A modified medium for efficient electrotransformation of *E. coli*," TIG, Apr. 1995, vol. 11, No. 4, pp. 128-129.

Wang et al., "Expanding the Genetic Code of *Escherichia coil*," Science, Apr. 20, 2001, vol. 292, pp. 498-500.

Wang et al., "Expanding the genetic code," Chem. Commun., 2002, pp. 1-11.

Wilson et al., "The use of mRNA display to select high-affinity protein-binding peptides," PNAS, Mar. 27, 2001, vol. 98, No. 7, pp. 3750-3755.

Yanisch-Perron et al., "Improved M13 phage cloning vectors and host strains: nucleotide sequences of the M13mp18 and pUC19 vectors," Gene, May 1, 1992, vol. 114, No. 1, pp. 81-83 (Abstract, one page).

Zapun et al., "Structural and functional characterization of DsbC, a protein involved in disulfide bond formation in *Escherichia coli*," Biochemistry, Apr. 18, 1995, vol. 34, No. 15, pp. 5075-5089 (Abstract, one page).

A. Skerra, "Anticalins: A New Class of Engineered Ligand-Binding Proteins With Antibody-Like Properties", Reviews in Molecular Biotechnology, Elsevier, Amsterdam, NL, vol. 74, No. 4, Jun. 2001, pp. 257-275.

D. Flower, "Multiple molecular recognition properties of the lipocalin protein family", Journal of Molecular Recognition, Heyden & Son Ltd., London, GB, vol. 8, 1995, pp. 185-195.

\* cited by examiner

PCR No.1

PCR No.2

SEQUENCE LISTING

```
<160> NUMBER OF SEQ ID NOS: 73

<210> SEQ ID NO 1
<211> LENGTH: 1189
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: sig_peptide
<222> LOCATION: (22)..(84)
<220> FEATURE:
<221> NAME/KEY: mat_peptide
<222> LOCATION: (85)..(1179)
<223> OTHER INFORMATION: Fusion protein of modified BBP and a fragment
      of phage coat protein pIII
<220> FEATURE:
<221> NAME/KEY: CDS
<222> LOCATION: (22)..(1179)
<220> FEATURE:
<221> NAME/KEY: misc_feature
<222> LOCATION: (85)..(606)
<223> OTHER INFORMATION: Mature BBP
<220> FEATURE:
<221> NAME/KEY: misc_feature
<222> LOCATION: (607)..(609)
<223> OTHER INFORMATION: Amber stop codon
<220> FEATURE:
<221> NAME/KEY: misc_feature
<222> LOCATION: (610)..(1179)
<223> OTHER INFORMATION: Amino acids 217-406 of coat protein pIII

<400> SEQUENCE: 1
tctagataac gagggcaaaa a atg aaa aag aca gct atc gcg att gca gtg         51
                        Met Lys Lys Thr Ala Ile Ala Ile Ala Val
                            -20                 -15 gca ctg gct ggt ttc gct acc gta gcg cag gcc gac gtg tac cac gac         99
Ala Leu Ala Gly Phe Ala Thr Val Ala Gln Ala Asp Val Tyr His Asp
     -10                 -5              -1  1                 5
```

```
ggt gcc tgt ccc gaa gtc aag cca gtc gac aac ttc gac tgg tcc cag         147
Gly Ala Cys Pro Glu Val Lys Pro Val Asp Asn Phe Asp Trp Ser Gln
         10                  15                  20 tac cat ggt aaa tgg tgg gaa gtc gcc aaa tac ccc aac tca gtt gag         195
Tyr His Gly Lys Trp Trp Glu Val Ala Lys Tyr Pro Asn Ser Val Glu
         25                  30                  35 aag tac gga aat taa tga tgg gct gag tac act cct gaa ggc aag agt         243
Lys Tyr Gly Asn Cys Gly Trp Ala Glu Tyr Thr Pro Glu Gly Lys Ser
         40                  45                  50 gtc aaa gtt tcg aac tac cac gta atc cac ggc aag gaa tac ttt att         291
Val Lys Val Ser Asn Tyr His Val Ile His Gly Lys Glu Tyr Phe Ile
         55                  60                  65 gaa gga act gcc tac cca gtt ggt gac tcc aag att gga aag atc tac         339
Glu Gly Thr Ala Tyr Pro Val Gly Asp Ser Lys Ile Gly Lys Ile Tyr
 70              75                  80                  85 cac agc ctg act tac gga ggt gtc acc aag gag aac gta ttc aac gta         387
His Ser Leu Thr Tyr Gly Gly Val Thr Lys Glu Asn Val Phe Asn Val
                 90                  95                  100 ctc tcc act gac aac aag aac tac atc atc gga tac tac tgc aaa tac         435
Leu Ser Thr Asp Asn Lys Asn Tyr Ile Ile Gly Tyr Tyr Cys Lys Tyr
                 105                 110                 115 gac gag gac aag aag gga cac caa gac ttc gtc tgg gtg ctc tcc aga         483
Asp Glu Asp Lys Lys Gly His Gln Asp Phe Val Trp Val Leu Ser Arg
         120                 125                 130 agc atg gtc ctt act ggt gaa gcc aag acc gct gtc gag aac tac ctt         531
Ser Met Val Leu Thr Gly Glu Ala Lys Thr Ala Val Glu Asn Tyr Leu
         135                 140                 145 atc ggc tcc cca gta gtc gac tcc cag aaa ctg gta tac agt gac ttc         579
Ile Gly Ser Pro Val Val Asp Ser Gln Lys Leu Val Tyr Ser Asp Phe
150                 155                 160                 165 tct gaa gcc gcc tgc aag gtc aac aat tag gct ggc ggc tct ggt         627
Ser Glu Ala Ala Cys Lys Val Asn Asn Gln Ala Gly Gly Gly Ser Gly
                 170                 175                 180 ggt ggt tct ggc ggc ggc tct gag ggt ggt ggc tct gag ggt ggc ggt         675
Gly Gly Ser Gly Gly Gly Ser Glu Gly Gly Gly Ser Glu Gly Gly Gly
                 185                 190                 195 tct gag ggt ggc ggc tct gag gga ggc ggt tcc ggt ggt ggc tct ggt         723
Ser Glu Gly Gly Gly Ser Glu Gly Gly Gly Ser Gly Gly Gly Ser Gly
                 200                 205                 210 tcc ggt gat ttt gat tat gaa aag atg gca aac gct aat aag ggg gct         771
Ser Gly Asp Phe Asp Tyr Glu Lys Met Ala Asn Ala Asn Lys Gly Ala
215                 220                 225 atg acc gaa aat gcc gat gaa aac gcg cta cag tct gac gct aaa ggc         819
Met Thr Glu Asn Ala Asp Glu Asn Ala Leu Gln Ser Asp Ala Lys Gly
230                 235                 240                 245 aaa ctt gat tct gtc gct act gat tac ggt gct gct atc gat ggt ttc         867
Lys Leu Asp Ser Val Ala Thr Asp Tyr Gly Ala Ala Ile Asp Gly Phe
                 250                 255                 260 att ggt gac gtt tcc ggc ctt gct aat ggt aat ggt gct act ggt gat         915
Ile Gly Asp Val Ser Gly Leu Ala Asn Gly Asn Gly Ala Thr Gly Asp
                 265                 270                 275 ttt gct ggc tct aat tcc caa atg gct caa gtc ggt gac ggt gat aat         963
Phe Ala Gly Ser Asn Ser Gln Met Ala Gln Val Gly Asp Gly Asp Asn
                 280                 285                 290 tca cct tta atg aat aat ttc cgt caa tat tta cct tcc ctc cct caa        1011
Ser Pro Leu Met Asn Asn Phe Arg Gln Tyr Leu Pro Ser Leu Pro Gln
         295                 300                 305 tcg gtt gaa tgt cgc cct ttt gtc ttt ggc gct ggt aaa cca tat gaa        1059
Ser Val Glu Cys Arg Pro Phe Val Phe Gly Ala Gly Lys Pro Tyr Glu
310                 315                 320                 325
```

```
ttt tct att gat tgt gac aaa ata aac tta ttc cgt ggt gtc ttt gcg    1107
Phe Ser Ile Asp Cys Asp Lys Ile Asn Leu Phe Arg Gly Val Phe Ala
        330                 335                 340 ttt ctt tta tat gtt gcc acc ttt atg tat gta ttt tct acg ttt gct    1155
Phe Leu Leu Tyr Val Ala Thr Phe Met Tyr Val Phe Ser Thr Phe Ala
    345                 350                 355 aac ata ctg cgt aat aag gag tct taataagctt                         1189
Asn Ile Leu Arg Asn Lys Glu Ser
        360             365
```

<210> SEQ ID NO 2
<211> LENGTH: 71
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(39)
<223> OTHER INFORMATION: a, c, t or g
<220> FEATURE:
<221> NAME/KEY: modified_base
<222> LOCATION: (41)..(42)
<223> OTHER INFORMATION: a, c, t or g
<220> FEATURE:
<221> NAME/KEY: modified_base
<222> LOCATION: (47)..(48)
<223> OTHER INFORMATION: a, c, t or g
<220> FEATURE:
<221> NAME/KEY: modified_base
<222> LOCATION: (50)..(51)
<223> OTHER INFORMATION: a, c, t or g

<400> SEQUENCE: 2
ccatggtaaa tggtgggaag tcgccaaata ccccaacnns nnsgagnnsn nsggaaagtg    60
cggatgggct g                                                         71

<210> SEQ ID NO 3
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(26)
<223> OTHER INFORMATION: a, c, t or g
<220> FEATURE:
<221> NAME/KEY: modified_base
<222> LOCATION: (31)..(32)
<223> OTHER INFORMATION: a, c, t or g
<220> FEATURE:
<221> NAME/KEY: modified_base
<222> LOCATION: (34)..(35)
<223> OTHER INFORMATION: a, c, t or g
<220> FEATURE:
<221> NAME/KEY: modified_base
<222> LOCATION: (37)..(38)
<223> OTHER INFORMATION: a, c, t or g

<400> SEQUENCE: 3
gggtaggcgg taccttcaat aaasnnttcs nnsnnsnnga ttacgtggta gttcgaaac    59

<210> SEQ ID NO 4
<211> LENGTH: 65
<212> TYPE: DNA
<213> ORGANISM: Artificial Sequence
<220> FEATURE:

```
<223> OTHER INFORMATION: Description of Artificial Sequence: Synthetic
      primer
<220> FEATURE:
<221> NAME/KEY: modified_base
<222> LOCATION: (33)..(34)
<223> OTHER INFORMATION: a, c, t or g
<220> FEATURE:
<221> NAME/KEY: modified_base
<222> LOCATION: (36)..(37)
<223> OTHER INFORMATION: a, c, t or g
<220> FEATURE:
<221> NAME/KEY: modified_base
<222> LOCATION: (42)..(43)
<223> OTHER INFORMATION: a, c, t or g

<400> SEQUENCE: 4
ccaagattgg aaagatctac cacagcctga ctnnsnnsgg tnnsaccaag gagaacgtat      60
tcaac                                                                 65

<210> SEQ ID NO 5
<211> LENGTH: 73
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, t or g
<220> FEATURE:
<221> NAME/KEY: modified_base
<222> LOCATION: (38)..(39)
<223> OTHER INFORMATION: a, c, t or g
<220> FEATURE:
<221> NAME/KEY: modified_base
<222> LOCATION: (41)..(42)
<223> OTHER INFORMATION: a, c, t or g
<220> FEATURE:
<221> NAME/KEY: modified_base
<222> LOCATION: (47)..(48)
<223> OTHER INFORMATION: a, c, t or g
<220> FEATURE:
<221> NAME/KEY: modified_base
<222> LOCATION: (53)..(54)
<223> OTHER INFORMATION: a, c, t or g

<400> SEQUENCE: 5
tctggagagc acccagacga agtcsnngtg tcccttsnns nnctcsnngt asnngcagta      60
gtatccgatg atg                                                        73

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agatctttcc aatcttggag tcaccaactg ggtaggcggt accttc                    46

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
```

-continued

```
cttcgactgg tcccagtacc atggtaaatg gtggga                              36
```

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
caccagtaag gaccatgctt ctggagagca cccagac                             37
```

<210> SEQ ID NO 9
<211> LENGTH: 487
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: sig_peptide
<222> LOCATION: (22)..(84)
<220> FEATURE:
<221> NAME/KEY: mat_peptide
<222> LOCATION: (85)..(477)
<223> OTHER INFORMATION: Fusion protein of the extracellular domain of
      CD47-C15A, and a Strep-tag II affinity tag
<220> FEATURE:
<221> NAME/KEY: CDS
<222> LOCATION: (22)..(477)
<220> FEATURE:
<221> NAME/KEY: misc_feature
<222> LOCATION: (85)..(447)
<223> OTHER INFORMATION: Mature CD47-C15A
<220> FEATURE:
<221> NAME/KEY: misc_feature
<222> LOCATION: (448)..(477)
<223> OTHER INFORMATION: Strep-tag II affinity tag

<400> SEQUENCE: 9

```
tctagataac gagggcaaaa a atg aaa aag aca gct atc gcg att gca gtg       51
                        Met Lys Lys Thr Ala Ile Ala Ile Ala Val
                            -20                 -15 gca ctg gct ggt ttc gct acc gta gcg cag gcc cag cta cta ttt aat       99
Ala Leu Ala Gly Phe Ala Thr Val Ala Gln Ala Gln Leu Leu Phe Asn
    -10              -5                  -1  1                5 aaa aca aaa tct gta gaa ttc acg ttt gct aat gac act gtc gtc att      147
Lys Thr Lys Ser Val Glu Phe Thr Phe Ala Asn Asp Thr Val Val Ile
                10                  15                  20 cca tgc ttt gtt act aat atg gag gca caa aac act act gaa gta tac      195
Pro Cys Phe Val Thr Asn Met Glu Ala Gln Asn Thr Thr Glu Val Tyr
            25                  30                  35 gta aag tgg aaa ttt aaa gga aga gat att tac acc ttt gat gga gct      243
Val Lys Trp Lys Phe Lys Gly Arg Asp Ile Tyr Thr Phe Asp Gly Ala
        40                  45                  50 cta aac aag tcc act gtc ccc act gac ttt agt agt gca aaa att gaa      291
Leu Asn Lys Ser Thr Val Pro Thr Asp Phe Ser Ser Ala Lys Ile Glu
    55                  60                  65 gtc tca caa tta cta aaa gga gat gcc tct ttg aag atg gat aag agt      339
Val Ser Gln Leu Leu Lys Gly Asp Ala Ser Leu Lys Met Asp Lys Ser
70                  75                  80                  85 gat gct gtc tca cac aca gga aac tac act tgt gaa gta aca gaa tta      387
Asp Ala Val Ser His Thr Gly Asn Tyr Thr Cys Glu Val Thr Glu Leu
                90                  95                 100 acc aga gaa ggt gaa acg atc atc gag cta aaa tat cgt gtt gtt tca      435
```

```
Thr Arg Glu Gly Glu Thr Ile Ile Glu Leu Lys Tyr Arg Val Val Ser
            105                 110                 115 tgg ttt tct cca agc gct tgg tct cac ccg cag ttc gaa aaa              477
Trp Phe Ser Pro Ser Ala Trp Ser His Pro Gln Phe Glu Lys
        120                 125                 130 taataagctt                                                            487

<210> SEQ ID NO 10
<211> LENGTH: 679
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: sig_peptide
<222> LOCATION: (22)..(84)
<220> FEATURE:
<221> NAME/KEY: mat_peptide
<222> LOCATION: (85)..(669)
<223> OTHER INFORMATION: Fusion protein of T7-tag, BBP and Strep-tag II
<220> FEATURE:
<221> NAME/KEY: CDS
<222> LOCATION: (22)..(669)
<220> FEATURE:
<221> NAME/KEY: misc_feature
<222> LOCATION: (85)..(117)
<223> OTHER INFORMATION: T7-tag
<220> FEATURE:
<221> NAME/KEY: misc_feature
<222> LOCATION: (118)..(639)
<223> OTHER INFORMATION: Mature BBP
<220> FEATURE:
<221> NAME/KEY: misc_feature
<222> LOCATION: (640)..(669)
<223> OTHER INFORMATION: Strep-tag II affinity tag

<400> SEQUENCE: 10
tctagataac gagggcaaaa a atg aaa aag aca gct atc gcg att gca gtg       51
                       Met Lys Lys Thr Ala Ile Ala Ile Ala Val
                       -20                 -15 gca ctg gct ggt ttc gct acc gta gcg cag gcc gat gca tcg atg acc       99
Ala Leu Ala Gly Phe Ala Thr Val Ala Gln Ala Asp Ala Ser Met Thr
    -10                 -5                  -1   1               5 ggt ggt cag cag atg ggt gac gtg tac cac gac ggt gcc tgt ccc gaa      147
Gly Gly Gln Gln Met Gly Asp Val Tyr His Asp Gly Ala Cys Pro Glu
                10                  15                  20 gtc aag cca gtc gac aac ttc gac tgg tcc cag tac cat ggt aaa tgg      195
Val Lys Pro Val Asp Asn Phe Asp Trp Ser Gln Tyr His Gly Lys Trp
            25                  30                  35 tgg gaa gtc gcc aaa tac ccc aac tca gtt gag aag tac gga aag tgc      243
Trp Glu Val Ala Lys Tyr Pro Asn Ser Val Glu Lys Tyr Gly Lys Cys
        40                  45                  50 gga tgg gct gag tac act cct gaa ggc aag agt gtc aaa gtt tcg aac      291
Gly Trp Ala Glu Tyr Thr Pro Glu Gly Lys Ser Val Lys Val Ser Asn
    55                  60                  65 tac cac gta atc cac ggc aag gaa tac ttt att gaa gga act gcc tac      339
Tyr His Val Ile His Gly Lys Glu Tyr Phe Ile Glu Gly Thr Ala Tyr
70                  75                  80                  85 cca gtt ggt gac tcc aag att gga aag atc tac cac agc ctg act tac      387
Pro Val Gly Asp Ser Lys Ile Gly Lys Ile Tyr His Ser Leu Thr Tyr
                90                  95                 100 gga ggt gtc acc aag gag aac gta ttc aac gta ctc tcc act gac aac      435
Gly Gly Val Thr Lys Glu Asn Val Phe Asn Val Leu Ser Thr Asp Asn
            105                 110                 115 aag aac tac atc atc gga tac tac tgc aaa tac gac gag gac aag aag      483
```

```
                Lys Asn Tyr Ile Ile Gly Tyr Tyr Cys Lys Tyr Asp Glu Asp Lys Lys
                            120                 125                 130 gga cac caa gac ttc gtc tgg gtg ctc tcc aga agc atg gtc ctt act            531
Gly His Gln Asp Phe Val Trp Val Leu Ser Arg Ser Met Val Leu Thr
        135                 140                 145 ggt gaa gcc aag acc gct gtc gag aac tac ctt atc ggc tcc cca gta            579
Gly Glu Ala Lys Thr Ala Val Glu Asn Tyr Leu Ile Gly Ser Pro Val
150                 155                 160                 165 gtc gac tcc cag aaa ctg gta tac agt gac ttc tct gaa gcc gcc tgc            627
Val Asp Ser Gln Lys Leu Val Tyr Ser Asp Phe Ser Glu Ala Ala Cys
                170                 175                 180 aag gtc aac aat agc aac tgg tct cac ccg cag ttc gaa aaa                    669
Lys Val Asn Asn Ser Asn Trp Ser His Pro Gln Phe Glu Lys
            185                 190                 195 taataagctt                                                                 679
```

<210> SEQ ID NO 11
<211> LENGTH: 679
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: sig_peptide
<222> LOCATION: (22)..(84)
<220> FEATURE:
<221> NAME/KEY: mat_peptide
<222> LOCATION: (85)..(669)
<223> OTHER INFORMATION: Fusion protein of modified BBP, T7-tag and
      Strep-tag II
<220> FEATURE:
<221> NAME/KEY: CDS
<222> LOCATION: (22)..(669)
<220> FEATURE:
<221> NAME/KEY: misc_feature
<222> LOCATION: (85)..(606)
<223> OTHER INFORMATION: Mature BBP
<220> FEATURE:
<221> NAME/KEY: misc_feature
<222> LOCATION: (607)..(639)
<223> OTHER INFORMATION: T7-tag
<220> FEATURE:
<221> NAME/KEY: misc_feature
<222> LOCATION: (640)..(669)
<223> OTHER INFORMATION: Strep-tag II

<400> SEQUENCE: 11

```
tctagataac gagggcaaaa a atg aaa aag aca gct atc gcg att gca gtg            51
                         Met Lys Lys Thr Ala Ile Ala Ile Ala Val
                             -20                 -15 gca ctg gct ggt ttc gct acc gta gcg cag gcc gac gtg tac cac gac            99
Ala Leu Ala Gly Phe Ala Thr Val Ala Gln Ala Asp Val Tyr His Asp
    -10                 -5              -1  1                   5 ggt gcc tgt ccc gaa gtc aag cca gtc gac aac ttc gac tgg tcc cag            147
Gly Ala Cys Pro Glu Val Lys Pro Val Asp Asn Phe Asp Trp Ser Gln
                    10                  15                  20 tac cat ggt aaa tgg tgg gaa gtc gcc aaa tac ccc aac tca gtt gag            195
Tyr His Gly Lys Trp Trp Glu Val Ala Lys Tyr Pro Asn Ser Val Glu
            25                  30                  35 aag tac gga aag tgc gga tgg gct gag tac act cct gaa ggc aag agt            243
Lys Tyr Gly Lys Cys Gly Trp Ala Glu Tyr Thr Pro Glu Gly Lys Ser
        40                  45                  50 gtc aaa gtt tcg aac tac cac gta atc cac ggc aag gaa tac ttt att            291
Val Lys Val Ser Asn Tyr His Val Ile His Gly Lys Glu Tyr Phe Ile
55                  60                  65
```

```
gaa gga act gcc tac cca gtt ggt gac tcc aag att gga aag atc tac        339
Glu Gly Thr Ala Tyr Pro Val Gly Asp Ser Lys Ile Gly Lys Ile Tyr
 70              75                  80                  85 cac agc ctg act tac gga ggt gtc acc aag gag aac gta ttc aac gta        387
His Ser Leu Thr Tyr Gly Gly Val Thr Lys Glu Asn Val Phe Asn Val
             90                  95                 100 ctc tcc act gac aac aag aac tac atc atc gga tac tac tgc aaa tac       435
Leu Ser Thr Asp Asn Lys Asn Tyr Ile Ile Gly Tyr Tyr Cys Lys Tyr
            105                 110                 115 gac gag gac aag aag gga cac caa gac ttc gtc tgg gtg ctc tcc aga       483
Asp Glu Asp Lys Lys Gly His Gln Asp Phe Val Trp Val Leu Ser Arg
        120                 125                 130 agc atg gtc ctt act ggt gaa gcc aag acc gct gtc gag aac tac ctt       531
Ser Met Val Leu Thr Gly Glu Ala Lys Thr Ala Val Glu Asn Tyr Leu
    135                 140                 145 atc ggc tcc cca gta gtc gac tcc cag aaa ctg gta tac agt gac ttc       579
Ile Gly Ser Pro Val Val Asp Ser Gln Lys Leu Val Tyr Ser Asp Phe
150                 155                 160                 165 tct gaa gcc gcc tgc aag gtc aac aat gat gca tcg atg acc ggt ggt       627
Ser Glu Ala Ala Cys Lys Val Asn Asn Asp Ala Ser Met Thr Gly Gly
                170                 175                 180 cag cag atg ggt agc gct tgg tct cac ccg cag ttc gaa aaa                669
Gln Gln Met Gly Ser Ala Trp Ser His Pro Gln Phe Glu Lys
            185                 190                 195 taataagctt                                                             679

<210> SEQ ID NO 12
<211> LENGTH: 1222
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: sig_peptide
<222> LOCATION: (22)..(84)
<220> FEATURE:
<221> NAME/KEY: mat_peptide
<222> LOCATION: (85)..(1212)
<223> OTHER INFORMATION: Fusion protein of T7-tag, a modified BBP, and a
      fragment of phage coat protein III
<220> FEATURE:
<221> NAME/KEY: CDS
<222> LOCATION: (22)..(1212)
<220> FEATURE:
<221> NAME/KEY: misc_feature
<222> LOCATION: (85)..(117)
<223> OTHER INFORMATION: T7-tag
<220> FEATURE:
<221> NAME/KEY: misc_feature
<222> LOCATION: (118)..(639)
<223> OTHER INFORMATION: Mature BBP
<220> FEATURE:
<221> NAME/KEY: misc_feature
<222> LOCATION: (640)..(642)
<223> OTHER INFORMATION: Amber stop codon
<220> FEATURE:
<221> NAME/KEY: misc_feature
<222> LOCATION: (643)..(1212)
<223> OTHER INFORMATION: Amino acids 217-406 of coat protein pIII

<400> SEQUENCE: 12
tctagataac gagggcaaaa a atg aaa aag aca gct atc gcg att gca gtg        51
                        Met Lys Lys Thr Ala Ile Ala Ile Ala Val
                            -20                 -15 gca ctg gct ggt ttc gct acc gta gcg cag gcc gat gca tcg atg acc        99
Ala Leu Ala Gly Phe Ala Thr Val Ala Gln Ala Asp Ala Ser Met Thr
        -10                  -5          -1   1               5
```

-continued

```
ggt ggt cag cag atg ggt gac gtg tac cac gac ggt gcc tgt ccc gaa      147
Gly Gly Gln Gln Met Gly Asp Val Tyr His Asp Gly Ala Cys Pro Glu
             10                  15                  20 gtc aag cca gtc gac aac ttc gac tgg tcc cag tac cat ggt aaa tgg      195
Val Lys Pro Val Asp Asn Phe Asp Trp Ser Gln Tyr His Gly Lys Trp
         25                  30                  35 tgg gaa gtc gcc aaa tac ccc aac tca gtt gag aag tac gga aat taa      243
Trp Glu Val Ala Lys Tyr Pro Asn Ser Val Glu Lys Tyr Gly Asn Cys
     40                  45                  50 tga tgg gct gag tac act cct gaa ggc aag agt gtc aaa gtt tcg aac      291
Gly Trp Ala Glu Tyr Thr Pro Glu Gly Lys Ser Val Lys Val Ser Asn
 55                  60                  65 tac cac gta atc cac ggc aag gaa tac ttt att gaa gga act gcc tac      339
Tyr His Val Ile His Gly Lys Glu Tyr Phe Ile Glu Gly Thr Ala Tyr
 70                  75                  80                  85 cca gtt ggt gac tcc aag att gga aag atc tac cac agc ctg act tac      387
Pro Val Gly Asp Ser Lys Ile Gly Lys Ile Tyr His Ser Leu Thr Tyr
             90                  95                 100 gga ggt gtc acc aag gag aac gta ttc aac gta ctc tcc act gac aac      435
Gly Gly Val Thr Lys Glu Asn Val Phe Asn Val Leu Ser Thr Asp Asn
        105                 110                 115 aag aac tac atc atc gga tac tac tgc aaa tac gac gag gac aag aag      483
Lys Asn Tyr Ile Ile Gly Tyr Tyr Cys Lys Tyr Asp Glu Asp Lys Lys
    120                 125                 130 gga cac caa gac ttc gtc tgg gtg ctc tcc aga agc atg gtc ctt act      531
Gly His Gln Asp Phe Val Trp Val Leu Ser Arg Ser Met Val Leu Thr
135                 140                 145 ggt gaa gcc aag acc gct gtc gag aac tac ctt atc ggc tcc cca gta      579
Gly Glu Ala Lys Thr Ala Val Glu Asn Tyr Leu Ile Gly Ser Pro Val
150                 155                 160                 165 gtc gac tcc cag aaa ctg gta tac agt gac ttc tct gaa gcc gcc tgc      627
Val Asp Ser Gln Lys Leu Val Tyr Ser Asp Phe Ser Glu Ala Ala Cys
                170                 175                 180 aag gtc aac aat tag gct ggc ggc ggc tct ggt ggt ggt tct ggc ggc      675
Lys Val Asn Asn Gln Ala Gly Gly Gly Ser Gly Gly Gly Ser Gly Gly
            185                 190                 195 ggc tct gag ggt ggt ggc tct gag ggt ggc ggt tct gag ggt ggc ggc      723
Gly Ser Glu Gly Gly Gly Ser Glu Gly Gly Gly Ser Glu Gly Gly Gly
        200                 205                 210 tct gag gga ggc ggt tcc ggt ggt ggc tct ggt tcc ggt gat ttt gat      771
Ser Glu Gly Gly Gly Ser Gly Gly Gly Ser Gly Ser Gly Asp Phe Asp
    215                 220                 225 tat gaa aag atg gca aac gct aat aag ggg gct atg acc gaa aat gcc      819
Tyr Glu Lys Met Ala Asn Ala Asn Lys Gly Ala Met Thr Glu Asn Ala
230                 235                 240                 245 gat gaa aac gcg cta cag tct gac gct aaa ggc aaa ctt gat tct gtc      867
Asp Glu Asn Ala Leu Gln Ser Asp Ala Lys Gly Lys Leu Asp Ser Val
                250                 255                 260 gct act gat tac ggt gct gct atc gat ggt ttc att ggt gac gtt tcc      915
Ala Thr Asp Tyr Gly Ala Ala Ile Asp Gly Phe Ile Gly Asp Val Ser
            265                 270                 275 ggc ctt gct aat ggt aat ggt gct act ggt gat ttt gct ggc tct aat      963
Gly Leu Ala Asn Gly Asn Gly Ala Thr Gly Asp Phe Ala Gly Ser Asn
        280                 285                 290 tcc caa atg gct caa gtc ggt gac ggt gat aat tca cct tta atg aat     1011
Ser Gln Met Ala Gln Val Gly Asp Gly Asp Asn Ser Pro Leu Met Asn
    295                 300                 305 aat ttc cgt caa tat tta cct tcc ctc cct caa tcg gtt gaa tgt cgc     1059
Asn Phe Arg Gln Tyr Leu Pro Ser Leu Pro Gln Ser Val Glu Cys Arg
```

-continued

```
                   310                 315                 320                 325
cct ttt gtc ttt ggc gct ggt aaa cca tat gaa ttt tct att gat tgt         1107
Pro Phe Val Phe Gly Ala Gly Lys Pro Tyr Glu Phe Ser Ile Asp Cys
                        330                 335                 340 gac aaa ata aac tta ttc cgt ggt gtc ttt gcg ttt ctt tta tat gtt         1155
Asp Lys Ile Asn Leu Phe Arg Gly Val Phe Ala Phe Leu Leu Tyr Val
            345                 350                 355 gcc acc ttt atg tat gta ttt tct acg ttt gct aac ata ctg cgt aat         1203
Ala Thr Phe Met Tyr Val Phe Ser Thr Phe Ala Asn Ile Leu Arg Asn
        360                 365                 370 aag gag tct taataagctt                                                  1222
Lys Glu Ser
    375

<210> SEQ ID NO 13
<211> LENGTH: 796
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: sig_peptide
<222> LOCATION: (22)..(84)
<220> FEATURE:
<221> NAME/KEY: mat_peptide
<222> LOCATION: (85)..(786)
<223> OTHER INFORMATION: Fusion protein of modified BBP, Strep-tag II
      and albumin-binding domain
<220> FEATURE:
<221> NAME/KEY: CDS
<222> LOCATION: (22)..(786)
<220> FEATURE:
<221> NAME/KEY: misc_feature
<222> LOCATION: (118)..(639)
<223> OTHER INFORMATION: Mature BBP
<220> FEATURE:
<221> NAME/KEY: misc_feature
<222> LOCATION: (607)..(636)
<223> OTHER INFORMATION: Strep-tag II affinity tag
<220> FEATURE:
<221> NAME/KEY: misc_feature
<222> LOCATION: (640)..(786)
<223> OTHER INFORMATION: Albumin binding domain of Protein G

<400> SEQUENCE: 13
tctagataac gagggcaaaa a atg aaa aag aca gct atc gcg att gca gtg         51
                        Met Lys Lys Thr Ala Ile Ala Ile Ala Val
                            -20                 -15 gca ctg gct ggt ttc gct acc gta gcg cag gcc gac gtg tac cac gac         99
Ala Leu Ala Gly Phe Ala Thr Val Ala Gln Ala Asp Val Tyr His Asp
        -10                 -5              -1  1                   5 ggt gcc tgt ccc gaa gtc aag cca gtc gac aac ttc gac tgg tcc cag         147
Gly Ala Cys Pro Glu Val Lys Pro Val Asp Asn Phe Asp Trp Ser Gln
                    10                  15                  20 tac cat ggt aaa tgg tgg gaa gtc gcc aaa tac ccc aac tca gtt gag         195
Tyr His Gly Lys Trp Trp Glu Val Ala Lys Tyr Pro Asn Ser Val Glu
            25                  30                  35 aag tac gga aag tgc gga tgg gct gag tac act cct gaa ggc aag agt         243
Lys Tyr Gly Lys Cys Gly Trp Ala Glu Tyr Thr Pro Glu Gly Lys Ser
        40                  45                  50 gtc aaa gtt tcg aac tac cac gta atc cac ggc aag gaa tac ttt att         291
Val Lys Val Ser Asn Tyr His Val Ile His Gly Lys Glu Tyr Phe Ile
    55                  60                  65 gaa gga act gcc tac cca gtt ggt gac tcc aag att gga aag atc tac         339
Glu Gly Thr Ala Tyr Pro Val Gly Asp Ser Lys Ile Gly Lys Ile Tyr
70                  75                  80                  85
```

```
cac agc ctg act tac gga ggt gtc acc aag gag aac gta ttc aac gta      387
His Ser Leu Thr Tyr Gly Gly Val Thr Lys Glu Asn Val Phe Asn Val
                90                  95                 100 ctc tcc act gac aac aag aac tac atc atc gga tac tac tgc aaa tac      435
Leu Ser Thr Asp Asn Lys Asn Tyr Ile Ile Gly Tyr Tyr Cys Lys Tyr
            105                 110                 115 gac gag gac aag aag gga cac caa gac ttc gtc tgg gtg ctc tcc aga      483
Asp Glu Asp Lys Lys Gly His Gln Asp Phe Val Trp Val Leu Ser Arg
        120                 125                 130 agc atg gtc ctt act ggt gaa gcc aag acc gct gtc gag aac tac ctt      531
Ser Met Val Leu Thr Gly Glu Ala Lys Thr Ala Val Glu Asn Tyr Leu
    135                 140                 145 atc ggc tcc cca gta gtc gac tcc cag aaa ctg gta tac agt gac ttc      579
Ile Gly Ser Pro Val Val Asp Ser Gln Lys Leu Val Tyr Ser Asp Phe
150                 155                 160                 165 tct gaa gcc gcc tgc aag gtc aac aat agc aac tgg tct cac ccg cag      627
Ser Glu Ala Ala Cys Lys Val Asn Asn Ser Asn Trp Ser His Pro Gln
                170                 175                 180 ttc gaa aaa tag cca gct agc ctg gct gaa gct aaa gtt ctg gct aac      675
Phe Glu Lys Gln Pro Ala Ser Leu Ala Glu Ala Lys Val Leu Ala Asn
            185                 190                 195 cgt gaa ctg gac aaa tac ggt gtt tcc gac tac tac aaa aac ctc atc      723
Arg Glu Leu Asp Lys Tyr Gly Val Ser Asp Tyr Tyr Lys Asn Leu Ile
        200                 205                 210 aac aac gct aaa acc gtt gaa ggt gtt aaa gct ctg atc gac gaa att      771
Asn Asn Ala Lys Thr Val Glu Gly Val Lys Ala Leu Ile Asp Glu Ile
    215                 220                 225 ctc gca gca ctg ccg taataagctt                                       796
Leu Ala Ala Leu Pro
230
```

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccactcccta tcagtgat                                                   18

<210> SEQ ID NO 15
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein CD47-F2

<400> SEQUENCE: 15

```
gac gtg t

-continued

```
                            35                  40                  45
cct gaa ggc aag agt gtc aaa gtt tcg aac tac cac gta atc cgg gcg      192
Pro Glu Gly Lys Ser Val Lys Val Ser Asn Tyr His Val Ile Arg Ala
        50                  55                  60 cag gaa tcc ttt att gaa ggt agc gcc tac cca gtt ggt gac tcc aag      240
Gln Glu Ser Phe Ile Glu Gly Ser Ala Tyr Pro Val Gly Asp Ser Lys
65                  70                  75                  80 att gga aag atc tac cac agc ctg act tac ttc ggt ctc acc aag gag      288
Ile Gly Lys Ile Tyr His Ser Leu Thr Tyr Phe Gly Leu Thr Lys Glu
                85                  90                  95 aac gta ttc aac gta ctc tcc act gac aac aag aac tac atc atc gga      336
Asn Val Phe Asn Val Leu Ser Thr Asp Asn Lys Asn Tyr Ile Ile Gly
            100                 105                 110 tac tac tgc gcc tac agg gag ctg ctc aag gga cac ggg gac ttc gtc      384
Tyr Tyr Cys Ala Tyr Arg Glu Leu Leu Lys Gly His Gly Asp Phe Val
        115                 120                 125 tgg gtg ctc tcc aga agc atg gtc ctt act ggt gaa gcc aag acc gct      432
Trp Val Leu Ser Arg Ser Met Val Leu Thr Gly Glu Ala Lys Thr Ala
    130                 135                 140 gtc gag aac tac ctt atc ggc tcc cca gta gtc gac tcc cag aaa ctg      480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat              522
Val Tyr Ser Asp Phe Ser Glu Ala Ala Cys Lys Val Asn Asn
                165                 170

<210> SEQ ID NO 16
<211> LENGTH: 519
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(519)
<223> OTHER INFORMATION: Mutein CD47-A9

<400> SEQUENCE: 16 gac gtg tac cac gac ggt gcc tgt ccc gaa gtc aag cca gtc gac aac       48
Asp Val Tyr His Asp Gly Ala Cys Pro Glu Val Lys Pro Val Asp Asn
1               5                   10                  15 ttc gac tgg tcc cag tac cat ggt aaa tgg tgg gaa gtc gcc aaa tac       96
Phe Asp Trp Ser Gln Tyr His Gly Lys Trp Trp Glu Val Ala Lys Tyr
                20                  25                  30 ccc aac gtc tag gag tgg acg gga aag tgc gga tgg gct gag tac act      144
Pro Asn Val Gln Glu Trp Thr Gly Lys Cys Gly Trp Ala Glu Tyr Thr
            35                  40                  45 cct gaa ggc aag agt gtc aaa gtt tcg aac tac cac gta atc agc ttc      192
Pro Glu Gly Lys Ser Val Lys Val Ser Asn Tyr His Val Ile Ser Phe
        50                  55                  60 aag gaa cgg ttt gaa ggt acc gcc tac cca gtt ggt gac ccc aag att      240
Lys Glu Arg Phe Glu Gly Thr Ala Tyr Pro Val Gly Asp Pro Lys Ile
65                  70                  75                  80 gga aag atc tac cac agc ctg act ttg cgg ggt tgg acc aag gag aac      288
Gly Lys Ile Tyr His Ser Leu Thr Leu Arg Gly Trp Thr Lys Glu Asn
                85                  90                  95 gta ttc aac gta ctc tcc act gac aac aag aac tac atc atc gga tac      336
Val Phe Asn Val Leu Ser Thr Asp Asn Lys Asn Tyr Ile Ile Gly Tyr
            100                 105                 110 tac tgc acg tac cgc gag tgg gcc aag gga cac ttc gac ttc gtc tgg      384
Tyr Cys Thr Tyr Arg Glu Trp Ala Lys Gly His Phe Asp Phe Val Trp
```

-continued

```
                115                 120                 125
gtg ctc tcc aga agc atg gtc ctt act ggt gaa gcc aag acc gct gtc      432
Val Leu Ser Arg Ser Met Val Leu Thr Gly Glu Ala Lys Thr Ala Val
    130                 135                 140 gag aac tac ctt atc ggc tcc cca gta gtc gac tcc cag aaa ctg gta      480
Glu Asn Tyr Leu Ile Gly Ser Pro Val Val Asp Ser Gln Lys Leu Val
145                 150                 155                 160 tac agt gac ttc tct gaa gcc gcc tgc aag gtc aac aat                  519
Tyr Ser Asp Phe Ser Glu Ala Ala Cys Lys Val Asn Asn
                165                 170
```

<210> SEQ ID NO 17
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein CD47-F11

<400> SEQUENCE: 17

```
gac gtg tac cac gac ggt gcc tgt ccc gaa gtc aag cca gtc gac aac      48
Asp Val Tyr His Asp Gly Ala Cys Pro Glu Val Lys Pro Val Asp Asn
1               5                   10                  15 ttc gac tgg tcc cag tac cat ggt aaa tgg tgg gaa gtc gcc aaa tac      96
Phe Asp Trp Ser Gln Tyr His Gly Lys Trp Trp Glu Val Ala Lys Tyr
            20                  25                  30 ccc aac tag ggg gag ccc ccc gga aag tgc gga tgg gct gag tac act      144
Pro Asn Gln Gly Glu Pro Pro Gly Lys Cys Gly Trp Ala Glu Tyr Thr
        35                  40                  45 cct gaa ggc aag agt gtc aaa gtt tcg aac tac cac gta atc agc cgg      192
Pro Glu Gly Lys Ser Val Lys Val Ser Asn Tyr His Val Ile Ser Arg
    50                  55                  60 tac gaa cgc ttt att gaa ggt acc gcc tac cca gtt ggt gac tcc aag      240
Tyr Glu Arg Phe Ile Glu Gly Thr Ala Tyr Pro Val Gly Asp Ser Lys
65                  70                  75                  80 att gga aag atc tac cac agc ctg act gtg ggg ggt tac acc aag gag      288
Ile Gly Lys Ile Tyr His Ser Leu Thr Val Gly Gly Tyr Thr Lys Glu
                85                  90                  95 aac gta ttc aac gta ctc tcc act gac aac aag aac tac atc atc gga      336
Asn Val Phe Asn Val Leu Ser Thr Asp Asn Lys Asn Tyr Ile Ile Gly
            100                 105                 110 tac tac tgc tcg tac ttg gag tac ctc aag gga cac ctc gac ttc ggc      384
Tyr Tyr Cys Ser Tyr Leu Glu Tyr Leu Lys Gly His Leu Asp Phe Gly
        115                 120                 125 tgg gtg ctc tcc aga agc atg gtc ctt act ggt gaa gcc aag acc gct      432
Trp Val Leu Ser Arg Ser Met Val Leu Thr Gly Glu Ala Lys Thr Ala
    130                 135                 140 gtc gag aac tac ctt atc ggc tcc cca gta gtc gac tcc cag aaa ctg      480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat              522
Val Tyr Ser Asp Phe Ser Glu Ala Ala Cys Lys Val Asn Asn
                165                 170
```

<210> SEQ ID NO 18
<211> LENGTH: 522
<212> TYPE: DNA
<213> ORGANISM: Artificial Sequence
<220> FEATURE:

-continued

<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein CD47-G6

<400> SEQUENCE: 18

```
gac gtg tac cac gac ggt gcc tgt ccc gaa gtc aag cca gtc gac aac        48
Asp Val Tyr His Asp Gly Ala Cys Pro Glu Val Lys Pro Val Asp Asn
  1               5                  10                  15 ttc gac tgg tcc cag tac cat ggt aaa tgg tgg gaa gtc gcc aaa tac        96
Phe Asp Trp Ser Gln Tyr His Gly Lys Trp Trp Glu Val Ala Lys Tyr
             20                  25                  30 ccc aac cgg cgg gag aag ttc gga aag tgc gga tgg gct gag tac act       144
Pro Asn Arg Arg Glu Lys Phe Gly Lys Cys Gly Trp Ala Glu Tyr Thr
         35                  40                  45 cct gaa ggc aag agt gtc aaa gtt tcg aac tac cac gta atc cgg tgg       192
Pro Glu Gly Lys Ser Val Lys Val Ser Asn Tyr His Val Ile Arg Trp
     50                  55                  60 ggc gaa cgc ttt att gaa ggt acc gcc tac cca gtt ggt gac tcc aag       240
Gly Glu Arg Phe Ile Glu Gly Thr Ala Tyr Pro Val Gly Asp Ser Lys
 65                  70                  75                  80 att gga aag atc tac cac agc ctg act ctg ccc ggt tac acc aag gag       288
Ile Gly Lys Ile Tyr His Ser Leu Thr Leu Pro Gly Tyr Thr Lys Glu
                 85                  90                  95 aac gta ttc aac gta ctc tcc act gac aac aag aac tac atc atc gga       336
Asn Val Phe Asn Val Leu Ser Thr Asp Asn Lys Asn Tyr Ile Ile Gly
            100                 105                 110 tac tac tgc aag tac ctc gag cgc ctg aag gga cac gcg gac ttc gtc       384
Tyr Tyr Cys Lys Tyr Leu Glu Arg Leu Lys Gly His Ala Asp Phe Val
        115                 120                 125 tgg gtg ctc tcc aga agc atg gtc ctt act ggt gaa gcc aag acc gct       432
Trp Val Leu Ser Arg Ser Met Val Leu Thr Gly Glu Ala Lys Thr Ala
    130                 135                 140 gtc gag aac tac ctt atc ggc tcc cca gta gtc gac tcc cag aaa ctg       480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat               522
Val Tyr Ser Asp Phe Ser Glu Ala Ala Cys Lys Val Asn Asn
                165                 170
```

<210> SEQ ID NO 19
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein Fer-N22

<400> SEQUENCE: 19

```
gac gtg tac cac gac ggt gcc tgt ccc gaa gtc aag cca gtc gac aac        48
Asp Val Tyr His Asp Gly Ala Cys Pro Glu Val Lys Pro Val Asp Asn
  1               5                  10                  15 ttc gac tgg tcc cag tac cat ggt aaa tgg tgg gaa gtc gcc aaa tac        96
Phe Asp Trp Ser Gln Tyr His Gly Lys Trp Trp Glu Val Ala Lys Tyr
             20                  25                  30 ccc aac ggg ggc gag agc ccc gga aag tgc gga tgg gct gag tac act       144
Pro Asn Gly Gly Glu Ser Pro Gly Lys Cys Gly Trp Ala Glu Tyr Thr
         35                  40                  45
```

```
cct gaa ggc aag agt gtc aaa gtt tcg aac tac cac gta atc aag aag      192
Pro Glu Gly Lys Ser Val Lys Val Ser Asn Tyr His Val Ile Lys Lys
     50                  55                  60 agg gaa agg ttt att gaa ggt acc gcc tac cca gtt ggt gac tcc aag      240
Arg Glu Arg Phe Ile Glu Gly Thr Ala Tyr Pro Val Gly Asp Ser Lys
 65                  70                  75                  80 att gga aag atc tgc cac agc ctg act tgg tcc ggt ttg acc aag gag      288
Ile Gly Lys Ile Cys His Ser Leu Thr Trp Ser Gly Leu Thr Lys Glu
                 85                  90                  95 aac gta ttc aac gta ctc tcc act gac aac aag aac tac atc atc gga      336
Asn Val Phe Asn Val Leu Ser Thr Asp Asn Lys Asn Tyr Ile Ile Gly
             100                 105                 110 tac tac tgc aag tac aag gag cgc aag aag gga cac ggc gac ttc gtc      384
Tyr Tyr Cys Lys Tyr Lys Glu Arg Lys Lys Gly His Gly Asp Phe Val
         115                 120                 125 tgg gtg ctc tcc aga agc atg gtc ctt act ggt gaa gcc aag acc gct      432
Trp Val Leu Ser Arg Ser Met Val Leu Thr Gly Glu Ala Lys Thr Ala
     130                 135                 140 gtc gag aac tac ctt atc ggc tcc cca gta gtc gac tcc cag aaa ctg      480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat              522
Val Tyr Ser Asp Phe Ser Glu Ala Ala Cys Lys Val Asn Asn
                165                 170

<210> SEQ ID NO 20
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein Fer-I21

<400> SEQUENCE: 20 gac gtg tac cac gac ggt gcc tgt ccc gaa gtc aag cca gtc gac aac      48
Asp Val Tyr His Asp Gly Ala Cys Pro Glu Val Lys Pro Val Asp Asn
 1               5                  10                  15 ttc gac tgg tcc cag tac cat ggt aaa tgg tgg gaa gtc gcc aaa tac      96
Phe Asp Trp Ser Gln Tyr His Gly Lys Trp Trp Glu Val Ala Lys Tyr
                 20                  25                  30 ccc aac cag aag gag aag tgg gga aag tgc gga tgg gct gag tac act     144
Pro Asn Gln Lys Glu Lys Trp Gly Lys Cys Gly Trp Ala Glu Tyr Thr
             35                  40                  45 cct gaa ggc aag agt gtc aaa gtt tcg aac tac cac gta atc aag agg     192
Pro Glu Gly Lys Ser Val Lys Val Ser Asn Tyr His Val Ile Lys Arg
     50                  55                  60 ccg gaa agg ttt att gaa ggt acc gcc tac cca gtt ggt gac tcc aag     240
Pro Glu Arg Phe Ile Glu Gly Thr Ala Tyr Pro Val Gly Asp Ser Lys
 65                  70                  75                  80 att gga aag atc tac cac agc ctg act agg ttg ggt aag acc aag gag     288
Ile Gly Lys Ile Tyr His Ser Leu Thr Arg Leu Gly Lys Thr Lys Glu
                 85                  90                  95 aac gta ttc aac gta ctc tcc act gac aac aag aac tac atc atc gga     336
Asn Val Phe Asn Val Leu Ser Thr Asp Asn Lys Asn Tyr Ile Ile Gly
             100                 105                 110 tac tac tgc ctg tac ccg gag ggc tgg aag gga cac aag gac ttc gtc     384
Tyr Tyr Cys Leu Tyr Pro Glu Gly Trp Lys Gly His Lys Asp Phe Val
         115                 120                 125
```

```
tgg gtg ctc tcc aga agc atg gtc ctt act ggt gaa gcc aag acc gct    432
Trp Val Leu Ser Arg Ser Met Val Leu Thr Gly Glu Ala Lys Thr Ala
    130                 135                 140 gtc gag aac tac ctt atc ggc tcc cca gta gtc gac tcc cag aaa ctg    480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat            522
Val Tyr Ser Asp Phe Ser Glu Ala Ala Cys Lys Val Asn Asn
                165                 170

<210> SEQ ID NO 21
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein Fer-D24

<400> SEQUENCE: 21 gac gtg tac cac gac ggt gcc tgt ccc gaa gtc aag cca gtc gac aac     48
Asp Val Tyr His Asp Gly Ala Cys Pro Glu Val Lys Pro Val Asp Asn
  1               5                  10                  15 ttc gac tgg tcc cag tac cat ggt aaa tgg tgg gaa gtc gcc aaa tac     96
Phe Asp Trp Ser Gln Tyr His Gly Lys Trp Trp Glu Val Ala Lys Tyr
             20                  25                  30 ccc agt aag aag ggg aag cag gga aag tgc gga tgg gct gag tac act    144
Pro Ser Lys Lys Gly Lys Gln Gly Lys Cys Gly Trp Ala Glu Tyr Thr
         35                  40                  45 cct gaa ggc aag agt gtc aaa gtt tcg cgc tac gat gta atc ccc tgc    192
Pro Glu Gly Lys Ser Val Lys Val Ser Arg Tyr Asp Val Ile Pro Cys
     50                  55                  60 ctg gaa tcc ttt atg gaa ggt acc gcc tac cca gtt ggt gac tcc aag    240
Leu Glu Ser Phe Met Glu Gly Thr Ala Tyr Pro Val Gly Asp Ser Lys
 65                  70                  75                  80 att gga aag atc tac cac agc agg act aag ccc ggt agg acc aaa aag    288
Ile Gly Lys Ile Tyr His Ser Arg Thr Lys Pro Gly Arg Thr Lys Lys
                 85                  90                  95 acg gta ttc aac gta ccc tcc act gac aac aag aac tac atc atc gga    336
Thr Val Phe Asn Val Pro Ser Thr Asp Asn Lys Asn Tyr Ile Ile Gly
            100                 105                 110 tac tcg tgc gtc tac ccc gag ggc cgc aag gga cac cgc gac cat gtc    384
Tyr Ser Cys Val Tyr Pro Glu Gly Arg Lys Gly His Arg Asp His Val
        115                 120                 125 tgg gtg ctc tcc aga agc atg gtc ctt act ggt gaa gcc aag acc gct    432
Trp Val Leu Ser Arg Ser Met Val Leu Thr Gly Glu Ala Lys Thr Ala
    130                 135                 140 gtc gag aac tac ctt atc ggc tcc cca gta gtc gac tcc cag aaa ctg    480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat            522
Val Tyr Ser Asp Phe Ser Glu Ala Ala Cys Lys Val Asn Asn
                165                 170

<210> SEQ ID NO 22
<211> LENGTH: 522
<212> TYPE: DNA
<213> ORGANISM: Artificial Sequence
<220> FEATURE:
<223> OTHER INFORMATION: Description of Artificial Sequence: Synthetic
```

-continued

```
                    construct
<220> FEATURE:
<221> NAME/KEY: CDS
<222> LOCATION: (1)..(522)
<223> OTHER INFORMATION: Mutein Fer-N21

<400> SEQUENCE: 22 gac gtg tac cac gac ggt gcc tgt ccc gaa gtc aag cca gtc gac aac      48
Asp Val Tyr His Asp Gly Ala Cys Pro Glu Val Lys Pro Val Asp Asn
 1               5                  10                  15 ttc gac tgg tcc cag tac cat ggt aaa tgg tgg gaa gtc gcc aaa tac      96
Phe Asp Trp Ser Gln Tyr His Gly Lys Trp Trp Glu Val Ala Lys Tyr
                20                  25                  30 ccc agt aac cgg ggg tcg aag gga aag tgc gga tgg gct gag tac act     144
Pro Ser Asn Arg Gly Ser Lys Gly Lys Cys Gly Trp Ala Glu Tyr Thr
            35                  40                  45 cct gaa ggc aag agt gtc aaa gtt tcg cgc tac gat gta atc ccg cgc     192
Pro Glu Gly Lys Ser Val Lys Val Ser Arg Tyr Asp Val Ile Pro Arg
        50                  55                  60 ttg gaa gcc ttt atg gaa ggt acc gcc tac cca gtt ggt gac tcc aag     240
Leu Glu Ala Phe Met Glu Gly Thr Ala Tyr Pro Val Gly Asp Ser Lys
 65                 70                  75                  80 att gga aag atc tac cac agc agg act agc aag ggt aag acc aaa aag     288
Ile Gly Lys Ile Tyr His Ser Arg Thr Ser Lys Gly Lys Thr Lys Lys
                85                  90                  95 acg gta ttc aac gta ctc tcc act gac aac aag aac tac atc atc gga     336
Thr Val Phe Asn Val Leu Ser Thr Asp Asn Lys Asn Tyr Ile Ile Gly
               100                 105                 110 tac tcg tgc atc tac aac gag cgg tac aag gga cac tac gac cat gtc     384
Tyr Ser Cys Ile Tyr Asn Glu Arg Tyr Lys Gly His Tyr Asp His Val
            115                 120                 125 tgg gtg ctc tcc aga agc atg gtc ctt act ggt gaa gcc aag acc gct     432
Trp Val Leu Ser Arg Ser Met Val Leu Thr Gly Glu Ala Lys Thr Ala
        130                 135                 140 gtc gag aac tac ctt atc ggc tcc cca gta gtc gac tcc cag aaa ctg     480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat                 522
Val Tyr Ser Asp Phe Ser Glu Ala Ala Cys Lys Val Asn Asn
                165                 170

<210> SEQ ID NO 23
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein Fer-P4

<400> SEQUENCE: 23 gac gtg tac cac gac ggt gcc tgt ccc gaa gtc aag cca gtc gac aac      48
Asp Val Tyr His Asp Gly Ala Cys Pro Glu Val Lys Pro Val Asp Asn
 1               5                  10                  15 ttc gac tgg tcc cag tac cat ggt aaa tgg tgg gaa gtc gcc aaa tac      96
Phe Asp Trp Ser Gln Tyr His Gly Lys Trp Trp Glu Val Ala Lys Tyr
                20                  25                  30 ccc agt aag ggg ggg gag aag gga aag tgc gga tgg gct gag tac act     144
Pro Ser Lys Gly Gly Glu Lys Gly Lys Cys Gly Trp Ala Glu Tyr Thr
            35                  40                  45
```

```
cct gaa ggc aag agt gtc aaa gtt tcg cgc tac gat gta atc ctc tcc        192
Pro Glu Gly Lys Ser Val Lys Val Ser Arg Tyr Asp Val Ile Leu Ser
    50                  55                  60 tcg gaa ccg ttt atg gaa ggt acc gcc tac cca gtt ggt gac tcc aag        240
Ser Glu Pro Phe Met Glu Gly Thr Ala Tyr Pro Val Gly Asp Ser Lys
65                  70                  75                  80 att gga aag atc tac cac agc agg act aag aag ggt gag acc aaa aag        288
Ile Gly Lys Ile Tyr His Ser Arg Thr Lys Lys Gly Glu Thr Lys Lys
                85                  90                  95 acg gta ttc aac gta ctc tcc act gac aac aag aac tac atc atc gga        336
Thr Val Phe Asn Val Leu Ser Thr Asp Asn Lys Asn Tyr Ile Ile Gly
            100                 105                 110 tac tcg tgc ggg tac tgc gag tgc cgc aag gga cac gcc gac cat gtc        384
Tyr Ser Cys Gly Tyr Cys Glu Cys Arg Lys Gly His Ala Asp His Val
        115                 120                 125 tgg gtg ctc tcc aga agc atg gtc ctt act ggt gaa gcc aag acc gct        432
Trp Val Leu Ser Arg Ser Met Val Leu Thr Gly Glu Ala Lys Thr Ala
130                 135                 140 gtc gag aac tac ctt atc ggc tcc cca gta gtc gac tcc cag aaa ctg        480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat                522
Val Tyr Ser Asp Phe Ser Glu Ala Ala Cys Lys Val Asn Asn
                165                 170

<210> SEQ ID NO 24
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein Fer-O20

<400> SEQUENCE: 24 gac gtg tac cac gac ggt gcc tgt ccc gaa gtc aag cca gtc gac aac        48
Asp Val Tyr His Asp Gly Ala Cys Pro Glu Val Lys Pro Val Asp Asn
1               5                   10                  15 ttc gac tgg tcc cag tac cat ggt aaa tgg tgg gaa gtc gcc aaa tgc        96
Phe Asp Trp Ser Gln Tyr His Gly Lys Trp Trp Glu Val Ala Lys Cys
                20                  25                  30 ccc agt ggc aag ggg cgg gcc gga aag tgc gga tgg gct gag ttc act        144
Pro Ser Gly Lys Gly Arg Ala Gly Lys Cys Gly Trp Ala Glu Phe Thr
            35                  40                  45 cct gaa ggc aag agt gtc aaa gtt tcg cgc tac gat gta atc ccg gcc        192
Pro Glu Gly Lys Ser Val Lys Val Ser Arg Tyr Asp Val Ile Pro Ala
    50                  55                  60 ccg gaa ctg ttt atg gaa ggt acc gcc tac cca gtt ggt gac ccc aag        240
Pro Glu Leu Phe Met Glu Gly Thr Ala Tyr Pro Val Gly Asp Pro Lys
65                  70                  75                  80 att gga aag atc tac cac agc agg act aac aag ggt ctg acc aaa aag        288
Ile Gly Lys Ile Tyr His Ser Arg Thr Asn Lys Gly Leu Thr Lys Lys
                85                  90                  95 acg gta ttc aac gta ctc tcc act gac aac aag aac tac atc atc gga        336
Thr Val Phe Asn Val Leu Ser Thr Asp Asn Lys Asn Tyr Ile Ile Gly
            100                 105                 110 tac tcg tgc aag tac ggc gag gac cag aag gga cac aag gac cat gtc        384
Tyr Ser Cys Lys Tyr Gly Glu Asp Gln Lys Gly His Lys Asp His Val
        115                 120                 125
```

```
tgg gtg ctc tcc aga agc atg gtc ctt act ggt gaa gcc aag acc gct    432
Trp Val Leu Ser Arg Ser Met Val Leu Thr Gly Glu Ala Lys Thr Ala
    130                 135                 140 gtc gag aac tac ctt atc ggc tcc cca gta gtc gac tcc cag aaa ctg    480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat            522
Val Tyr Ser Asp Phe Ser Glu Ala Ala Cys Lys Val Asn Asn
                165                 170

<210> SEQ ID NO 25
<211> LENGTH: 430
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: sig_peptide
<222> LOCATION: (22)..(84)
<220> FEATURE:
<221> NAME/KEY: mat_peptide
<222> LOCATION: (85)..(420)
<223> OTHER INFORMATION: Fusion protein of extracellular domain CD4V and
      strep-tag II
<220> FEATURE:
<221> NAME/KEY: CDS
<222> LOCATION: (22)..(420)
<220> FEATURE:
<221> NAME/KEY: misc_feature
<222> LOCATION: (85)..(390)
<223> OTHER INFORMATION: Mature CD4V
<220> FEATURE:
<221> NAME/KEY: misc_feature
<222> LOCATION: (391)..(420)
<223> OTHER INFORMATION: Strep-tag II affinity tag

<400> SEQUENCE: 25
tctagataac gagggcaaaa a atg aaa aag aca gct atc gcg att gca gtg    51
                       Met Lys Lys Thr Ala Ile Ala Ile Ala Val
                           -20                 -15 gca ctg gct ggt ttc gct acc gta gcg cag gcc gca aag aaa gtg gtg    99
Ala Leu Ala Gly Phe Ala Thr Val Ala Gln Ala Ala Lys Lys Val Val
    -10                 -5              -1   1               5 ctg ggc aaa aaa ggg gat aca gtg gaa ctg acc tgt aca gct tcc cag    147
Leu Gly Lys Lys Gly Asp Thr Val Glu Leu Thr Cys Thr Ala Ser Gln
                10                  15                  20 aag aag agc ata caa ttc cac tgg aaa aac tcc aac cag ata aag att    195
Lys Lys Ser Ile Gln Phe His Trp Lys Asn Ser Asn Gln Ile Lys Ile
            25                  30                  35 ctg gga aat cag ggc tcc ttc tta act aaa ggt cca tcc aag ctg aat    243
Leu Gly Asn Gln Gly Ser Phe Leu Thr Lys Gly Pro Ser Lys Leu Asn
        40                  45                  50 gat cgc gct gac tca aga aga agc ctt tgg gac caa gga aac ttt ccc    291
Asp Arg Ala Asp Ser Arg Arg Ser Leu Trp Asp Gln Gly Asn Phe Pro
    55                  60                  65 ctg atc atc aag aat ctt aag ata gaa gac tca gat act tac atc tgt    339
Leu Ile Ile Lys Asn Leu Lys Ile Glu Asp Ser Asp Thr Tyr Ile Cys
70                  75                  80                  85 gaa gtg gag gac cag aag gag gag gtg caa ttg cta gtg ttc gga ttg    387
Glu Val Glu Asp Gln Lys Glu Glu Val Gln Leu Leu Val Phe Gly Leu
                90                  95                  100 act agc gct tgg tct cac ccg cag ttc gaa aaa taataagctt             430
Thr Ser Ala Trp Ser His Pro Gln Phe Glu Lys
            105                 110
```

<210> SEQ ID NO 26
<211> LENGTH: 373
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: sig_peptide
<222> LOCATION: (22)..(84)
<220> FEATURE:
<221> NAME/KEY: mat_peptide
<222> LOCATION: (85)..(363)
<223> OTHER INFORMATION: Fusion protein of extracellular domain CD4D1
      and strep-tag II
<220> FEATURE:
<221> NAME/KEY: CDS
<222> LOCATION: (22)..(363)
<220> FEATURE:
<221> NAME/KEY: misc_feature
<222> LOCATION: (85)..(333)
<223> OTHER INFORMATION: Mature CD4D1
<220> FEATURE:
<221> NAME/KEY: misc_feature
<222> LOCATION: (334)..(363)
<223> OTHER INFORMATION: Strep-tag II affinity tag

<400> SEQUENCE: 26

```
tctagataac gagggcaaaa a atg aaa aag aca gct atc gcg att gca gtg       51
                        Met Lys Lys Thr Ala Ile Ala Ile Ala Val
                            -20                 -15 gca ctg gct ggt ttc gct acc gta gcg cag gcc gcc aac tct gac acc       99
Ala Leu Ala Gly Phe Ala Thr Val Ala Gln Ala Ala Asn Ser Asp Thr
    -10                 -5                  -1   1               5 cac ctg ctt cag ggg cag agc ctg acc ctg acc ttg gag agc ccc cct      147
His Leu Leu Gln Gly Gln Ser Leu Thr Leu Thr Leu Glu Ser Pro Pro
                10                  15                  20 ggt agt agc ccc tca gtg caa tgt agg agt cca agg ggt aaa aac ata      195
Gly Ser Ser Pro Ser Val Gln Cys Arg Ser Pro Arg Gly Lys Asn Ile
            25                  30                  35 cag ggg ggg aag acc ctc tcc gtg tct cag ctg gag ctc cag gat agt      243
Gln Gly Gly Lys Thr Leu Ser Val Ser Gln Leu Glu Leu Gln Asp Ser
        40                  45                  50 ggc acc tgg aca tgc act gtc ttg cag aac cag aag aag gtg gag ttc      291
Gly Thr Trp Thr Cys Thr Val Leu Gln Asn Gln Lys Lys Val Glu Phe
    55                  60                  65 aaa ata gac atc gtg gtg cta gct ttc cag aag gcc tcc agc agc gct      339
Lys Ile Asp Ile Val Val Leu Ala Phe Gln Lys Ala Ser Ser Ser Ala
70                  75                  80                  85 tgg tct cac ccg cag ttc gaa aaa taataagctt                           373
Trp Ser His Pro Gln Phe Glu Lys
                90
```

<210> SEQ ID NO 27
<211> LENGTH: 679
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: sig_peptide
<222> LOCATION: (22)..(84)
<220> FEATURE:
<221> NAME/KEY: mat_peptide
<222> LOCATION: (85)..(669)
<223> OTHER INFORMATION: Fusion protein of extracellular domain CD4VD1
      and strep-tag II
<220> FEATURE:
<221> NAME/KEY: CDS

```
<222> LOCATION: (22)..(669)
<220> FEATURE:
<221> NAME/KEY: misc_feature
<222> LOCATION: (85)..(639)
<223> OTHER INFORMATION: Mature CD4VD1
<220> FEATURE:
<221> NAME/KEY: misc_feature
<222> LOCATION: (640)..(669)
<223> OTHER INFORMATION: Strep-tag II affinity tag

<400> SEQUENCE: 27
tctagataac gagggcaaaa a atg aaa aag aca gct atc gcg att gca gtg          51
                        Met Lys Lys Thr Ala Ile Ala Ile Ala Val
                            -20                 -15 gca ctg gct ggt ttc gct acc gta gcg cag gcc gca aag aaa gtg gtg          99
Ala Leu Ala Gly Phe Ala Thr Val Ala Gln Ala Ala Lys Lys Val Val
    -10                 -5                  -1   1               5 ctg ggc aaa aaa ggg gat aca gtg gaa ctg acc tgt aca gct tcc cag         147
Leu Gly Lys Lys Gly Asp Thr Val Glu Leu Thr Cys Thr Ala Ser Gln
                10                  15                  20 aag aag agc ata caa ttc cac tgg aaa aac tcc aac cag ata aag att         195
Lys Lys Ser Ile Gln Phe His Trp Lys Asn Ser Asn Gln Ile Lys Ile
            25                  30                  35 ctg gga aat cag ggc tcc ttc tta act aaa ggt cca tcc aag ctg aat         243
Leu Gly Asn Gln Gly Ser Phe Leu Thr Lys Gly Pro Ser Lys Leu Asn
        40                  45                  50 gat cgc gct gac tca aga aga agc ctt tgg gac caa gga aac ttt ccc         291
Asp Arg Ala Asp Ser Arg Arg Ser Leu Trp Asp Gln Gly Asn Phe Pro
    55                  60                  65 ctg atc atc aag aat ctt aag ata gaa gac tca gat act tac atc tgt         339
Leu Ile Ile Lys Asn Leu Lys Ile Glu Asp Ser Asp Thr Tyr Ile Cys
70                  75                  80                  85 gaa gtg gag gac cag aag gag gag gtg caa ttg cta gtg ttc gga ttg         387
Glu Val Glu Asp Gln Lys Glu Glu Val Gln Leu Leu Val Phe Gly Leu
                90                  95                  100 act gcc aac tct gac acc cac ctg ctt cag ggg cag agc ctg acc ctg         435
Thr Ala Asn Ser Asp Thr His Leu Leu Gln Gly Gln Ser Leu Thr Leu
            105                 110                 115 acc ttg gag agc ccc cct ggt agt agc ccc tca gtg caa tgt agg agt         483
Thr Leu Glu Ser Pro Pro Gly Ser Ser Pro Ser Val Gln Cys Arg Ser
        120                 125                 130 cca agg ggt aaa aac ata cag ggg ggg aag acc ctc tcc gtg tct cag         531
Pro Arg Gly Lys Asn Ile Gln Gly Gly Lys Thr Leu Ser Val Ser Gln
    135                 140                 145 ctg gag ctc cag gat agt ggc acc tgg aca tgc act gtc ttg cag aac         579
Leu Glu Leu Gln Asp Ser Gly Thr Trp Thr Cys Thr Val Leu Gln Asn
150                 155                 160                 165 cag aag aag gtg gag ttc aaa ata gac atc gtg gtg cta gct ttc cag         627
Gln Lys Lys Val Glu Phe Lys Ile Asp Ile Val Val Leu Ala Phe Gln
                170                 175                 180 aag gcc tcc agc agc gct tgg tct cac ccg cag ttc gaa aaa                 669
Lys Ala Ser Ser Ser Ala Trp Ser His Pro Gln Phe Glu Lys
            185                 190                 195 taataagctt                                                              679

<210> SEQ ID NO 28
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
```

```
<221> NAME/KEY: CDS
<222> LOCATION: (1)..(522)
<223> OTHER INFORMATION: Mutein CD154-13-10-1

<400> SEQUENCE: 28 gac gtg tac cac gac ggt gcc tgt ccc gaa gtc aag cca gtc gac aac      48
Asp Val Tyr His Asp Gly Ala Cys Pro Glu Val Lys Pro Val Asp Asn
 1               5                  10                  15 ttc gac tgg tcc cag tac cat ggt aaa tgg tgg gaa gtc gcc aaa tac      96
Phe Asp Trp Ser Gln Tyr His Gly Lys Trp Trp Glu Val Ala Lys Tyr
             20                  25                  30 ccc aac cag atc gag cag ggg gga aag tgc gga tgg gct gag tac act     144
Pro Asn Gln Ile Glu Gln Gly Gly Lys Cys Gly Trp Ala Glu Tyr Thr
         35                  40                  45 cct gaa ggc aag agt gtc aaa gtt tcg aac tac cac gta atc tac gcc     192
Pro Glu Gly Lys Ser Val Lys Val Ser Asn Tyr His Val Ile Tyr Ala
     50                  55                  60 tcc gaa gac ttt att gaa ggt acc gcc tac cca gtt ggt gac tcc aag     240
Ser Glu Asp Phe Ile Glu Gly Thr Ala Tyr Pro Val Gly Asp Ser Lys
 65                  70                  75                  80 att gga aag atc tac cac agc ctg act tcg tcg ggt gtc acc aag gag     288
Ile Gly Lys Ile Tyr His Ser Leu Thr Ser Ser Gly Val Thr Lys Glu
                 85                  90                  95 aac gta ttc aac gta ctc tcc act gac aac aag aac tac atc atc gga     336
Asn Val Phe Asn Val Leu Ser Thr Asp Asn Lys Asn Tyr Ile Ile Gly
            100                 105                 110 tac tac tgc ggc tac cgg gag gcc ccc aag gga cac atg gac ttc gtc     384
Tyr Tyr Cys Gly Tyr Arg Glu Ala Pro Lys Gly His Met Asp Phe Val
        115                 120                 125 tgg gtg ctc tcc aga agc atg gtc ctt act ggt gaa gcc aag acc gct     432
Trp Val Leu Ser Arg Ser Met Val Leu Thr Gly Glu Ala Lys Thr Ala
    130                 135                 140 gtc gag aac tac ctt atc ggc tcc cca gta gtc gac tcc cag aaa ctg     480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat             522
Val Tyr Ser Asp Phe Ser Glu Ala Ala Cys Lys Val Asn Asn
                165                 170

<210> SEQ ID NO 29
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein CD154-13-10-2

<400> SEQUENCE: 29 gac gtg tac cac gac ggt gcc tgt ccc gaa gtc aag cca gtc gac aac      48
Asp Val Tyr His Asp Gly Ala Cys Pro Glu Val Lys Pro Val Asp Asn
 1               5                  10                  15 ttc gac tgg tcc cag tac cat ggt aaa tgg tgg gaa gtc gcc aaa tac      96
Phe Asp Trp Ser Gln Tyr His Gly Lys Trp Trp Glu Val Ala Lys Tyr
             20                  25                  30 ccc aac ggg acc gag gag agc gga aag tgc gga tgg gct gag tac act     144
Pro Asn Gly Thr Glu Glu Ser Gly Lys Cys Gly Trp Ala Glu Tyr Thr
         35                  40                  45 cct gaa ggc aag agt gtc aaa gtt tcg aac tac cac gta atc acg cag     192
Pro Glu Gly Lys Ser Val Lys Val Ser Asn Tyr His Val Ile Thr Gln
     50                  55                  60
```

```
                  50                  55                  60
ggg gaa aag ttt att gaa ggt acc gcc tac cca gtt ggt gac tcc aag        240
Gly Glu Lys Phe Ile Glu Gly Thr Ala Tyr Pro Val Gly Asp Ser Lys
 65                  70                  75                  80 att gga aag atc tac cac agc ctg act cgc ccg ggt ctc acc aag gag        288
Ile Gly Lys Ile Tyr His Ser Leu Thr Arg Pro Gly Leu Thr Lys Glu
                 85                  90                  95 aac gta ttc aac gta ctc tcc act gac aac aag aac tac atc atc gga        336
Asn Val Phe Asn Val Leu Ser Thr Asp Asn Lys Asn Tyr Ile Ile Gly
            100                 105                 110 tac tac tgc gac tac atg gag tgc aag aag gga cac gag gac ttc gtc        384
Tyr Tyr Cys Asp Tyr Met Glu Cys Lys Lys Gly His Glu Asp Phe Val
        115                 120                 125 tgg gtg ctc tcc aga agc atg gtc ctt act ggt gaa gcc aag acc gct        432
Trp Val Leu Ser Arg Ser Met Val Leu Thr Gly Glu Ala Lys Thr Ala
    130                 135                 140 gtc gag aac tac ctt atc ggc tcc cca gta gtc gac tcc cag aaa ctg        480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat                522
Val Tyr Ser Asp Phe Ser Glu Ala Ala Cys Lys Val Asn Asn
                165                 170

<210> SEQ ID NO 30
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein CD154-13-10-3

<400> SEQUENCE: 30 gac gtg tac cac gac ggt gcc tgt ccc gaa gtc aag cca gtc gac aac         48
Asp Val Tyr His Asp Gly Ala Cys Pro Glu Val Lys Pro Val Asp Asn
 1               5                  10                  15 ttc gac tgg tcc cag tac cat ggt aaa tgg tgg gaa gtc gcc aaa tac         96
Phe Asp Trp Ser Gln Tyr His Gly Lys Trp Trp Glu Val Ala Lys Tyr
                 20                  25                  30 ccc aac tgg ctc gag ctc gag gga aag tgc gga tgg gct gag tac act        144
Pro Asn Trp Leu Glu Leu Glu Gly Lys Cys Gly Trp Ala Glu Tyr Thr
             35                  40                  45 cct gaa ggt aag agt gtc aaa gtt tcg aac tac cac gta atc atg cag        192
Pro Glu Gly Lys Ser Val Lys Val Ser Asn Tyr His Val Ile Met Gln
         50                  55                  60 cag gaa ctg ttt att gaa ggt acc gcc tac cca gtt ggt gac tcc aag        240
Gln Glu Leu Phe Ile Glu Gly Thr Ala Tyr Pro Val Gly Asp Ser Lys
 65                  70                  75                  80 att gga aag atc tac cac agc ctg act gtg ccg ggt tag acc aag gag        288
Ile Gly Lys Ile Tyr His Ser Leu Thr Val Pro Gly Gln Thr Lys Glu
                 85                  90                  95 aac gta ttc aac gta ctc tcc act gac aac aag aac tac atc atc gga        336
Asn Val Phe Asn Val Leu Ser Thr Asp Asn Lys Asn Tyr Ile Ile Gly
            100                 105                 110 tac tac tgc ttc tac ccc gag gac gcc aag gga cac gtg gac ttc gtc        384
Tyr Tyr Cys Phe Tyr Pro Glu Asp Ala Lys Gly His Val Asp Phe Val
        115                 120                 125 tgg gtg ctc tcc aga agc atg gtc ctt act ggt gaa gcc aag acc gct        432
Trp Val Leu Ser Arg Ser Met Val Leu Thr Gly Glu Ala Lys Thr Ala
```

-continued

```
                130                 135                 140
gtc gag aac tac ctt atc ggc tcc cca gta gtc gac tcc cag aaa ctg     480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat             522
Val Tyr Ser Asp Phe Ser Glu Ala Ala Cys Lys Val Asn Asn
                165                 170

<210> SEQ ID NO 31
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein CD154-13-10-4

<400> SEQUENCE: 31 gac gtg tac cac gac ggt gcc tgt ccc gaa gtc aag cca gtc gac aac     48
Asp Val Tyr His Asp Gly Ala Cys Pro Glu Val Lys Pro Val Asp Asn
1               5                   10                  15 ttc gac tgg tcc cag tac cat ggt aaa tgg tgg gaa gtc gcc aaa tac     96
Phe Asp Trp Ser Gln Tyr His Gly Lys Trp Trp Glu Val Ala Lys Tyr
                20                  25                  30 ccc aac agc cac gag acc ggg gga aag tgc gga tgg gct gag tac act     144
Pro Asn Ser His Glu Thr Gly Gly Lys Cys Gly Trp Ala Glu Tyr Thr
            35                  40                  45 cct gaa ggc aag agt gtc aaa gtt tcg aac tac cac gta atc acc ccg     192
Pro Glu Gly Lys Ser Val Lys Val Ser Asn Tyr His Val Ile Thr Pro
        50                  55                  60 cac gaa cgc ttt att gaa ggt acc gcc tac cca gtt ggt gac tcc aag     240
His Glu Arg Phe Ile Glu Gly Thr Ala Tyr Pro Val Gly Asp Ser Lys
65                  70                  75                  80 att gga aag atc tac cac agc ctg act tgg atc ggt acg acc aag gag     288
Ile Gly Lys Ile Tyr His Ser Leu Thr Trp Ile Gly Thr Thr Lys Glu
                85                  90                  95 aac gta ttc aac gta ctc tcc act gac aac aag aac tac atc atc gga     336
Asn Val Phe Asn Val Leu Ser Thr Asp Asn Lys Asn Tyr Ile Ile Gly
            100                 105                 110 tac tac tgc tcc tac tcg gag gcc ggc aag gga cac cag gac ttc gtc     384
Tyr Tyr Cys Ser Tyr Ser Glu Ala Gly Lys Gly His Gln Asp Phe Val
        115                 120                 125 tgg gtg ctc tcc aga agc atg gtc ctt act ggt gaa gcc aag acc gct     432
Trp Val Leu Ser Arg Ser Met Val Leu Thr Gly Glu Ala Lys Thr Ala
130                 135                 140 gtc gag aac tac ctt atc ggc tcc cca gta gtc gac tcc cag aaa ctg     480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat             522
Val Tyr Ser Asp Phe Ser Glu Ala Ala Cys Lys Val Asn Asn
                165                 170

<210> SEQ ID NO 32
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
```

-continued

```
<222> LOCATION: (1)..(522)
<223> OTHER INFORMATION: Mutein CD154-13-10-5

<400> SEQUENCE: 32 gac gtg tac cac gac ggt gcc tgt ccc gaa gtc aag cca gtc gac aac      48
Asp Val Tyr His Asp Gly Ala Cys Pro Glu Val Lys Pro Val Asp Asn
 1               5                  10                  15 ttc gac tgg tcc cag tac cat ggt aaa tgg tgg gaa gtc gcc aaa tac      96
Phe Asp Trp Ser Gln Tyr His Gly Lys Trp Trp Glu Val Ala Lys Tyr
             20                  25                  30 ccc aac gtc acc gag atc ccg gga aag tgc gga tgg gct gag tac act     144
Pro Asn Val Thr Glu Ile Pro Gly Lys Cys Gly Trp Ala Glu Tyr Thr
         35                  40                  45 cct gaa ggc aag agt gtc aaa gtt tcg aac tac cac gta atc atg tcg     192
Pro Glu Gly Lys Ser Val Lys Val Ser Asn Tyr His Val Ile Met Ser
     50                  55                  60 ttc gaa ccg ttt att gaa ggt acc gcc tac cca gtt ggt gac tcc aag     240
Phe Glu Pro Phe Ile Glu Gly Thr Ala Tyr Pro Val Gly Asp Ser Lys
 65                  70                  75                  80 att gga aag atc tac cac agc ctg act agc tac ggt tag acc aag gag     288
Ile Gly Lys Ile Tyr His Ser Leu Thr Ser Tyr Gly Gln Thr Lys Glu
                 85                  90                  95 aac gta ttc aac gta ctc tcc act gac aac aag aac tac atc atc gga     336
Asn Val Phe Asn Val Leu Ser Thr Asp Asn Lys Asn Tyr Ile Ile Gly
            100                 105                 110 tac tac tgc gag tac atg gag tcc tcg aag gga cac aag gac ttc gtc     384
Tyr Tyr Cys Glu Tyr Met Glu Ser Ser Lys Gly His Lys Asp Phe Val
        115                 120                 125 tgg gtg ctc tcc aga agc atg gtc ctt act ggt gaa gcc aag acc gct     432
Trp Val Leu Ser Arg Ser Met Val Leu Thr Gly Glu Ala Lys Thr Ala
    130                 135                 140 gtc gag aac tac ctt atc ggc tcc cca gta gtc gac tcc cag aaa ctg     480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat              522
Val Tyr Ser Asp Phe Ser Glu Ala Ala Cys Lys Val Asn Asn
                165                 170

<210> SEQ ID NO 33
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein CD4-13-F4-10

<400> SEQUENCE: 33 gac gtg tac cac gac ggt gcc tgt ccc gaa gtc aag cca gtc gac aac      48
Asp Val Tyr His Asp Gly Ala Cys Pro Glu Val Lys Pro Val Asp Asn
 1               5                  10                  15 ttc gac tgg tcc cag tac cat ggt aaa tgg tgg gaa gtc gcc aaa tac      96
Phe Asp Trp Ser Gln Tyr His Gly Lys Trp Trp Glu Val Ala Lys Tyr
             20                  25                  30 ccc aac ccg gag gag tag gag gga aag tgc gga tgg gct gag tac act     144
Pro Asn Pro Glu Glu Gln Glu Gly Lys Cys Gly Trp Ala Glu Tyr Thr
         35                  40                  45 cct gaa ggc aag agt gtc aaa gtt tcg aac tac cac gta atc acc acg     192
Pro Glu Gly Lys Ser Val Lys Val Ser Asn Tyr His Val Ile Thr Thr
     50                  55                  60
```

```
gcc gaa aac ttt att gaa ggt acc gcc tac cca gtt ggt gac tcc aag      240
Ala Glu Asn Phe Ile Glu Gly Thr Ala Tyr Pro Val Gly Asp Ser Lys
 65                  70                  75                  80 att gga aag atc tac cac agc ctg act tgg cgg ggt atc acc aag gag      288
Ile Gly Lys Ile Tyr His Ser Leu Thr Trp Arg Gly Ile Thr Lys Glu
                 85                  90                  95 aac gta ttc aac gta ctc tcc act gac aac aag aac tac atc atc gga      336
Asn Val Phe Asn Val Leu Ser Thr Asp Asn Lys Asn Tyr Ile Ile Gly
            100                 105                 110 tac tac tgc tcc tac cgg gag tgg ttc aag gga cac ttc gac ttc gtc      384
Tyr Tyr Cys Ser Tyr Arg Glu Trp Phe Lys Gly His Phe Asp Phe Val
        115                 120                 125 tgg gtg ctc tcc aga agc atg gtc ctt act ggt gaa gcc aag acc gct      432
Trp Val Leu Ser Arg Ser Met Val Leu Thr Gly Glu Ala Lys Thr Ala
    130                 135                 140 gtc gag aac tac ctt atc ggc tcc cca gta gtc gac tcc cag aaa ctg      480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat              522
Val Tyr Ser Asp Phe Ser Glu Ala Ala Cys Lys Val Asn Asn
                165                 170

<210> SEQ ID NO 34
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein CD4-2C3-K20

<400> SEQUENCE: 34 gac gtg tac cac gac ggt gcc tgt ccc gaa gtc aag cca gtc gac aac       48
Asp Val Tyr His Asp Gly Ala Cys Pro Glu Val Lys Pro Val Asp Asn
  1               5                  10                  15 ttc gac tgg tcc cag tac cat ggt aaa tgg tgg gaa gtc gcc aaa tac       96
Phe Asp Trp Ser Gln Tyr His Gly Lys Trp Trp Glu Val Ala Lys Tyr
             20                  25                  30 ccc aac acc tcg gag cac tcc gga aag tgc gga tgg gct gag tac act      144
Pro Asn Thr Ser Glu His Ser Gly Lys Cys Gly Trp Ala Glu Tyr Thr
         35                  40                  45 cct gaa ggc aag agt gtc aaa gtt tcg aac tac cac gta atc aag aag      192
Pro Glu Gly Lys Ser Val Lys Val Ser Asn Tyr His Val Ile Lys Lys
     50                  55                  60 aag gaa agg ttt att gaa ggt acc gcc tac tca gct ggt gac tcc aag      240
Lys Glu Arg Phe Ile Glu Gly Thr Ala Tyr Ser Ala Gly Asp Ser Lys
 65                  70                  75                  80 att gga aag atc tac cac agc ctg act tcg gtc ggt aag acc aag gag      288
Ile Gly Lys Ile Tyr His Ser Leu Thr Ser Val Gly Lys Thr Lys Glu
                 85                  90                  95 aac gta ttc aac gta ctc tcc act gac aac aag aac tac atc atc gga      336
Asn Val Phe Asn Val Leu Ser Thr Asp Asn Lys Asn Tyr Ile Ile Gly
            100                 105                 110 tac tac tgc tcc tac aag gag aag acg aag gga cac ggc gac ttc gtc      384
Tyr Tyr Cys Ser Tyr Lys Glu Lys Thr Lys Gly His Gly Asp Phe Val
        115                 120                 125 tgg gtg ctc tcc aga agc atg gtc ctt act ggt gaa gcc aag acc gct      432
Trp Val Leu Ser Arg Ser Met Val Leu Thr Gly Glu Ala Lys Thr Ala
    130                 135                 140
```

-continued

```
gtc gag aac tac ctt atc ggc tcc cca gta gtc gac tcc cag aaa ctg      480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat              522
Val Tyr Ser Asp Phe Ser Glu Ala Ala Cys Lys Val Asn Asn
                165                 170
```

<210> SEQ ID NO 35
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein CD4-2C3-N22

<400> SEQUENCE: 35

```
gac gtg tac cac gac ggt gcc tgt ccc gaa gtc aag cca gtc gac aac       48
Asp Val Tyr His Asp Gly Ala Cys Pro Glu Val Lys Pro Val Asp Asn
1               5                   10                  15 ttc gac tgg tcc cag tac cat ggt aaa tgg tgg gaa gtc gcc aaa tac       96
Phe Asp Trp Ser Gln Tyr His Gly Lys Trp Trp Glu Val Ala Lys Tyr
            20                  25                  30 ccc aac gcc aag gag agc ccg gga aag tgc gga tgg gct gag tac act      144
Pro Asn Ala Lys Glu Ser Pro Gly Lys Cys Gly Trp Ala Glu Tyr Thr
        35                  40                  45 cct gaa ggc aag agt gtc aaa gtt tcg aac tac cac gta atc cag agg      192
Pro Glu Gly Lys Ser Val Lys Val Ser Asn Tyr His Val Ile Gln Arg
    50                  55                  60 ttg gaa ggg ttt att gaa ggt acc gcc tac cct gtt ggt gac tcc aag      240
Leu Glu Gly Phe Ile Glu Gly Thr Ala Tyr Pro Val Gly Asp Ser Lys
65                  70                  75                  80 att gga aag atc tac cac agc ctg act acg tgg ggt ttg acc aag gag      288
Ile Gly Lys Ile Tyr His Ser Leu Thr Thr Trp Gly Leu Thr Lys Glu
                85                  90                  95 aac gta ttc aac gta ctc tcc act gac aac aag aac tac atc atc gga      336
Asn Val Phe Asn Val Leu Ser Thr Asp Asn Lys Asn Tyr Ile Ile Gly
            100                 105                 110 tac tac tgc ggg tac gtg gag aag tcg aag gga cac ccg gac ttc gtc      384
Tyr Tyr Cys Gly Tyr Val Glu Lys Ser Lys Gly His Pro Asp Phe Val
        115                 120                 125 tgg gtg ctc tcc aga agc atg gtc ctt act ggt gaa gcc aag acc gct      432
Trp Val Leu Ser Arg Ser Met Val Leu Thr Gly Glu Ala Lys Thr Ala
    130                 135                 140 gtc gag aac tac ctt atc ggc tcc cca gta gtc gac tcc cag aaa ctg      480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat              522
Val Tyr Ser Asp Phe Ser Glu Ala Ala Cys Lys Val Asn Asn
                165                 170
```

<210> SEQ ID NO 36
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)

<223> OTHER INFORMATION: Mutein CD4-2G3-H22

<400> SEQUENCE: 36

```
gac gtg tac cac gac ggt gcc tgt ccc gaa gtc aag cca gtc gac aac        48
Asp Val Tyr His Asp Gly Ala Cys Pro Glu Val Lys Pro Val Asp Asn
 1               5                  10                  15 ttc gac tgg tcc cag tac cat ggt aaa tgg tgg gaa gtc gcc aaa tac        96
Phe Asp Trp Ser Gln Tyr His Gly Lys Trp Trp Glu Val Ala Lys Tyr
             20                  25                  30 ccc aac atg acc gag gtg aag gga aag tgc gga tgg gct gag tac act       144
Pro Asn Met Thr Glu Val Lys Gly Lys Cys Gly Trp Ala Glu Tyr Thr
         35                  40                  45 cct gaa ggc aag agt gtc aaa gtt tcg aac tac cac gta atc cgg gag       192
Pro Glu Gly Lys Ser Val Lys Val Ser Asn Tyr His Val Ile Arg Glu
     50                  55                  60 aag gaa tgg ttt att gaa ggt acc gcc tac cca gtt ggt gac tcc aag       240
Lys Glu Trp Phe Ile Glu Gly Thr Ala Tyr Pro Val Gly Asp Ser Lys
 65                  70                  75                  80 att gga aag atc tac cac agc ctg act atc tcc ggt ctg acc aag gag       288
Ile Gly Lys Ile Tyr His Ser Leu Thr Ile Ser Gly Leu Thr Lys Glu
                 85                  90                  95 aac gta ttc aac gta ctc tcc act gac gac aag aac tac atc atc gga       336
Asn Val Phe Asn Val Leu Ser Thr Asp Asp Lys Asn Tyr Ile Ile Gly
            100                 105                 110 tac tac tgc aag tac atg gag ttg tgg aag gga cac cgc gac ttc gtc       384
Tyr Tyr Cys Lys Tyr Met Glu Leu Trp Lys Gly His Arg Asp Phe Val
        115                 120                 125 tgg gtg ctc tcc aga agc atg gtc ctt act ggt gaa gcc aag acc gct       432
Trp Val Leu Ser Arg Ser Met Val Leu Thr Gly Glu Ala Lys Thr Ala
    130                 135                 140 gtc gag aac tac ctt atc ggc tcc cca gta gtc gac tcc cag aaa ctg       480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat               522
Val Tyr Ser Asp Phe Ser Glu Ala Ala Cys Lys Val Asn Asn
                165                 170
```

<210> SEQ ID NO 37
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein CD4-2G3-L22

<400> SEQUENCE: 37

```
gac gtg tac cac gac ggt gcc tgt ccc gaa gtc aag cca gtc gac aac        48
Asp Val Tyr His Asp Gly Ala Cys Pro Glu Val Lys Pro Val Asp Asn
 1               5                  10                  15 ttc gac tgg tcc cag tac cat ggt aaa tgg tgg gaa gtc gcc aaa tac        96
Phe Asp Trp Ser Gln Tyr His Gly Lys Trp Trp Glu Val Ala Lys Tyr
             20                  25                  30 ccc aac atc gcc gag ttg ggg gga aag tgc gga tgg gct gag tac act       144
Pro Asn Ile Ala Glu Leu Gly Gly Lys Cys Gly Trp Ala Glu Tyr Thr
         35                  40                  45 cct gaa ggc aag agt gtc aaa gtt tcg aac tac cac gta atc aac tgg       192
Pro Glu Gly Lys Ser Val Lys Val Ser Asn Tyr His Val Ile Asn Trp
     50                  55                  60
```

```
aac gaa atg ttt att gaa ggt acc gcc tac cca gtt ggt gac tcc aag      240
Asn Glu Met Phe Ile Glu Gly Thr Ala Tyr Pro Val Gly Asp Ser Lys
 65                  70                  75                  80 att gga aag atc tcc cac agc ctg act aag gtc ggt cag acc aag gag      288
Ile Gly Lys Ile Ser His Ser Leu Thr Lys Val Gly Gln Thr Lys Glu
                 85                  90                  95 aac gta ttc aac gta ctc tcc act gac aac aag aac tac atc atc gga      336
Asn Val Phe Asn Val Leu Ser Thr Asp Asn Lys Asn Tyr Ile Ile Gly
            100                 105                 110 tac tac tgc cag tac tcg gag cgg gcc aag gga cac ctg gac ttc gtc      384
Tyr Tyr Cys Gln Tyr Ser Glu Arg Ala Lys Gly His Leu Asp Phe Val
        115                 120                 125 tgg gtg ctc tcc aga agc atg gtc ctt act ggt gaa gcc aag acc gct      432
Trp Val Leu Ser Arg Ser Met Val Leu Thr Gly Glu Ala Lys Thr Ala
130                 135                 140 gtc gag aac tac ctt atc ggc tcc cca gta gtc gac tcc cag aaa ctg      480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat              522
Val Tyr Ser Asp Phe Ser Glu Ala Ala Cys Lys Val Asn Asn
                165                 170

<210> SEQ ID NO 38
<211> LENGTH: 522
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(522)
<223> OTHER INFORMATION: Mutein CD4-7B4-K21

<400> SEQUENCE: 38 gac gtg tac cac gac ggt gcc tgt ccc gaa gtc aag cca gtc gac aac       48
Asp Val Tyr His Asp Gly Ala Cys Pro Glu Val Lys Pro Val Asp Asn
  1               5                  10                  15 ttc gac tgg tcc cag tac cat ggt aaa tgg tgg gaa gtc gcc aaa tac       96
Phe Asp Trp Ser Gln Tyr His Gly Lys Trp Trp Glu Val Ala Lys Tyr
             20                  25                  30 ccc aac aag agg gag ggc cgg gga aag tgc gga tgg gct gag tac act      144
Pro Asn Lys Arg Glu Gly Arg Gly Lys Cys Gly Trp Ala Glu Tyr Thr
         35                  40                  45 cct gaa ggc aag agt gtc aaa gtt tcg aac tac cac gta atc acg ggg      192
Pro Glu Gly Lys Ser Val Lys Val Ser Asn Tyr His Val Ile Thr Gly
 50                  55                  60 aac gaa atc ttt att gaa ggt acc gcc tac cca gtt ggt gac tcc aag      240
Asn Glu Ile Phe Ile Glu Gly Thr Ala Tyr Pro Val Gly Asp Ser Lys
 65                  70                  75                  80 att gga aag atc tac tac agc ctg act aag acc ggt tcg acc aag gag      288
Ile Gly Lys Ile Tyr Tyr Ser Leu Thr Lys Thr Gly Ser Thr Lys Glu
                 85                  90                  95 aac gta ttc aac gta ctc tcc act gac aac aag aac tac atc atc gga      336
Asn Val Phe Asn Val Leu Ser Thr Asp Asn Lys Asn Tyr Ile Ile Gly
            100                 105                 110 tac tac tgc gtc tac ctc gag tac agc aag gga cac agg gac ttc gtc      384
Tyr Tyr Cys Val Tyr Leu Glu Tyr Ser Lys Gly His Arg Asp Phe Val
        115                 120                 125 tgg gtg ctc tcc aga agc atg gtc ctt act ggt gaa gcc aag acc gct      432
Trp Val Leu Ser Arg Ser Met Val Leu Thr Gly Glu Ala Lys Thr Ala
130                 135                 140
```

```
gtc gag aac tac ctt atc ggc tcc cca gta gtc gac tcc cag aaa ctg      480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat              522
Val Tyr Ser Asp Phe Ser Glu Ala Ala Cys Lys Val Asn Asn
            165                 170
```

<210> SEQ ID NO 39
<211> LENGTH: 522
<212> TYPE: DNA
<213> ORGANISM: Artificial Sequence
<220> FEATURE:
<223> OTHER INFORMATION: Description of Artificial Sequence: Synthetic construct
<220> FEATURE:
<221> NAME/KEY: CDS
<222> LOCATION: (1)..(522)
<223> OTHER INFORMATION: Mutein CD4-7B4-K23

<400> SEQUENCE: 39

```
gac gtg tac cac gac ggt gcc tgt ccc gaa gtc aag cca gtc gac aac      48
Asp Val Tyr His Asp Gly Ala Cys Pro Glu Val Lys Pro Val Asp Asn
1               5                   10                  15 ttc gac tgg tcc cag tac cat ggt aaa tgg tgg gaa gtc gcc aaa tac      96
Phe Asp Trp Ser Gln Tyr His Gly Lys Trp Trp Glu Val Ala Lys Tyr
            20                  25                  30 ccc aac ggc aac gag ctg agg gga aag tgc gga tgg gct gag tac act      144
Pro Asn Gly Asn Glu Leu Arg Gly Lys Cys Gly Trp Ala Glu Tyr Thr
        35                  40                  45 cct gaa ggc aag agt gtc aaa gtt tcg aac tac cac gta atc aac acg      192
Pro Glu Gly Lys Ser Val Lys Val Ser Asn Tyr His Val Ile Asn Thr
    50                  55                  60 tcc gaa ggg ttt att gaa ggt acc gcc tac cca gtt ggt gac tcc aag      240
Ser Glu Gly Phe Ile Glu Gly Thr Ala Tyr Pro Val Gly Asp Ser Lys
65                  70                  75                  80 att gga aag atc tac cac agc ctg act aac acc ggt atg acc aag gag      288
Ile Gly Lys Ile Tyr His Ser Leu Thr Asn Thr Gly Met Thr Lys Glu
                85                  90                  95 aac gta ttc aac gta ctc tcc act gac aac aag aac tac atc atc gga      336
Asn Val Phe Asn Val Leu Ser Thr Asp Asn Lys Asn Tyr Ile Ile Gly
            100                 105                 110 tac tac tgc agc tgg gag gtg tcc aag gga cac cac gac ttc gtc tgg      384
Tyr Tyr Cys Ser Trp Glu Val Ser Lys Gly His His Asp Phe Val Trp
        115                 120                 125 gtg ctc tcc aga agc atg gtc ctt act ggt gaa gcc aag acc gct gtc      432
Val Leu Ser Arg Ser Met Val Leu Thr Gly Glu Ala Lys Thr Ala Val
    130                 135                 140 gag aac tac ctt atc ggc tcc cca gta gtc gac tcc cag aaa ctg gta      480
Glu Asn Tyr Leu Ile Gly Ser Pro Val Val Asp Ser Gln Lys Leu Val
145                 150                 155                 160 tac agt gac ttc tct gaa gcc gcc tgc aag gtc aac aat agc              522
Tyr Ser Asp Phe Ser Glu Ala Ala Cys Lys Val Asn Asn Ser
            165                 170
```

<210> SEQ ID NO 40
<211> LENGTH: 522
<212> TYPE: DNA
<213> ORGANISM: Artificial Sequence
<220> FEATURE:
<223> OTHER INFORMATION: Description of Artificial Sequence: Synthetic construct
<220> FEATURE:
<221> NAME/KEY: CDS
<222> LOCATION: (1)..(522)
<223> OTHER INFORMATION: Mutein CD4-7B4-N14

```
<400> SEQUENCE: 40 gac gtg tac cac gac ggt gcc tgt ccc gaa gtc aag cca gtc gac aac    48
Asp Val Tyr His Asp Gly Ala Cys Pro Glu Val Lys Pro Val Asp Asn
 1               5                  10                  15 ttc gac tgg tcc cag tac cat ggt aaa tgg tgg gaa gtc gcc aaa tac    96
Phe Asp Trp Ser Gln Tyr His Gly Lys Trp Trp Glu Val Ala Lys Tyr
             20                  25                  30 ccc aac cgc gcc gag atc ggc gga aag tgc gga tgg gct gag tac act   144
Pro Asn Arg Ala Glu Ile Gly Gly Lys Cys Gly Trp Ala Glu Tyr Thr
         35                  40                  45 cct gaa ggc aag agt gtc aaa gtt tcg aac tac cac gta atc aag cag   192
Pro Glu Gly Lys Ser Val Lys Val Ser Asn Tyr His Val Ile Lys Gln
 50                  55                  60 tgg gaa aag ttt att gaa ggt acc gcc tac cca gtt ggt gac tcc aag   240
Trp Glu Lys Phe Ile Glu Gly Thr Ala Tyr Pro Val Gly Asp Ser Lys
 65                  70                  75                  80 att gga aag atc tac cac agc ctg act ggg acc ggt agc acc aag gag   288
Ile Gly Lys Ile Tyr His Ser Leu Thr Gly Thr Gly Ser Thr Lys Glu
             85                  90                  95 aac gta ttc aac gta ctc tcc act gac aac aag aac tac atc atc gga   336
Asn Val Phe Asn Val Leu Ser Thr Asp Asn Lys Asn Tyr Ile Ile Gly
            100                 105                 110 tac tac tgc aac tac cac gag tcc cgc aag gga cac cgg gac ttc gtc   384
Tyr Tyr Cys Asn Tyr His Glu Ser Arg Lys Gly His Arg Asp Phe Val
        115                 120                 125 tgg gtg ctc tcc aga agc atg gtc ctt act ggt gaa gcc aag acc gct   432
Trp Val Leu Ser Arg Ser Met Val Leu Thr Gly Glu Ala Lys Thr Ala
130                 135                 140 gtc gag aac tac ctt atc ggc tcc cca gta gtc gac tcc cag aaa ctg   480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat             522
Val Tyr Ser Asp Phe Ser Glu Ala Ala Cys Lys Val Asn Asn
                165                 170

<210> SEQ ID NO 41
<211> LENGTH: 386
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 41

Met Lys Lys Thr Ala Ile Ala Ile Ala Val Ala Leu Ala Gly Phe Ala
    -20                 -15                 -10

Thr Val Ala Gln Ala Asp Val Tyr His Asp Gly Ala Cys Pro Glu Val
 -5                  -1   1               5                  10

Lys Pro Val Asp Asn Phe Asp Trp Ser Gln Tyr His Gly Lys Trp Trp
                 15                  20                  25

Glu Val Ala Lys Tyr Pro Asn Ser Val Glu Lys Tyr Gly Asn Cys Gly
             30                  35                  40

Trp Ala Glu Tyr Thr Pro Glu Gly Lys Ser Val Lys Val Ser Asn Tyr
         45                  50                  55

His Val Ile His Gly Lys Glu Tyr Phe Ile Glu Gly Thr Ala Tyr Pro
 60                  65                  70                  75

Val Gly Asp Ser Lys Ile Gly Lys Ile Tyr His Ser Leu Thr Tyr Gly
             80                  85                  90
```

```
Gly Val Thr Lys Glu Asn Val Phe Asn Val Leu Ser Thr Asp Asn Lys
                 95                 100                 105

Asn Tyr Ile Ile Gly Tyr Tyr Cys Lys Tyr Asp Glu Asp Lys Lys Gly
            110                 115                 120

His Gln Asp Phe Val Trp Val Leu Ser Arg Ser Met Val Leu Thr Gly
        125                 130                 135

Glu Ala Lys Thr Ala Val Glu Asn Tyr Leu Ile Gly Ser Pro Val Val
140                 145                 150                 155

Asp Ser Gln Lys Leu Val Tyr Ser Asp Phe Ser Glu Ala Ala Cys Lys
                160                 165                 170

Val Asn Asn Gln Ala Gly Gly Ser Gly Gly Ser Gly Gly Ser Gly Gly
            175                 180                 185

Ser Glu Gly Gly Gly Ser Glu Gly Gly Ser Glu Gly Gly Gly Ser
        190                 195                 200

Glu Gly Gly Gly Ser Gly Gly Ser Gly Ser Gly Asp Phe Asp Tyr
205                 210                 215

Glu Lys Met Ala Asn Ala Asn Lys Gly Ala Met Thr Glu Asn Ala Asp
220                 225                 230                 235

Glu Asn Ala Leu Gln Ser Asp Ala Lys Gly Lys Leu Asp Ser Val Ala
                240                 245                 250

Thr Asp Tyr Gly Ala Ala Ile Asp Gly Phe Ile Gly Asp Val Ser Gly
            255                 260                 265

Leu Ala Asn Gly Asn Gly Ala Thr Gly Asp Phe Ala Gly Ser Asn Ser
        270                 275                 280

Gln Met Ala Gln Val Gly Asp Gly Asp Asn Ser Pro Leu Met Asn Asn
        285                 290                 295

Phe Arg Gln Tyr Leu Pro Ser Leu Pro Gln Ser Val Glu Cys Arg Pro
300                 305                 310                 315

Phe Val Phe Gly Ala Gly Lys Pro Tyr Glu Phe Ser Ile Asp Cys Asp
                320                 325                 330

Lys Ile Asn Leu Phe Arg Gly Val Phe Ala Phe Leu Leu Tyr Val Ala
            335                 340                 345

Thr Phe Met Tyr Val Phe Ser Thr Phe Ala Asn Ile Leu Arg Asn Lys
        350                 355                 360

Glu Ser
    365

<210> SEQ ID NO 42
<211> LENGTH: 152
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 42

Met Lys Lys Thr Ala Ile Ala Ile Ala Val Ala Leu Ala Gly Phe Ala
        -20                 -15                 -10

Thr Val Ala Gln Ala Gln Leu Leu Phe Asn Lys Thr Lys Ser Val Glu
 -5                  -1   1                   5                  10

Phe Thr Phe Ala Asn Asp Thr Val Val Ile Pro Cys Phe Val Thr Asn
            15                  20                  25

Met Glu Ala Gln Asn Thr Thr Glu Val Tyr Val Lys Trp Lys Phe Lys
        30                  35                  40

Gly Arg Asp Ile Tyr Thr Phe Asp Gly Ala Leu Asn Lys Ser Thr Val
    45                  50                  55
```

```
Pro Thr Asp Phe Ser Ser Ala Lys Ile Glu Val Ser Gln Leu Leu Lys
 60                  65                  70                  75

Gly Asp Ala Ser Leu Lys Met Asp Lys Ser Asp Ala Val Ser His Thr
                 80                  85                  90

Gly Asn Tyr Thr Cys Glu Val Thr Glu Leu Thr Arg Glu Gly Glu Thr
             95                 100                 105

Ile Ile Glu Leu Lys Tyr Arg Val Val Ser Trp Phe Ser Pro Ser Ala
        110                 115                 120

Trp Ser His Pro Gln Phe Glu Lys
    125                 130

<210> SEQ ID NO 43
<211> LENGTH: 216
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 43

Met Lys Lys Thr Ala Ile Ala Ile Ala Val Ala Leu Ala Gly Phe Ala
    -20                 -15                 -10

Thr Val Ala Gln Ala Asp Ala Ser Met Thr Gly Gly Gln Gln Met Gly
 -5              -1   1               5                  10

Asp Val Tyr His Asp Gly Ala Cys Pro Glu Val Lys Pro Val Asp Asn
             15                  20                  25

Phe Asp Trp Ser Gln Tyr His Gly Lys Trp Trp Glu Val Ala Lys Tyr
         30                  35                  40

Pro Asn Ser Val Glu Lys Tyr Gly Lys Cys Gly Trp Ala Glu Tyr Thr
     45                  50                  55

Pro Glu Gly Lys Ser Val Lys Val Ser Asn Tyr His Val Ile His Gly
 60                  65                  70                  75

Lys Glu Tyr Phe Ile Glu Gly Thr Ala Tyr Pro Val Gly Asp Ser Lys
                 80                  85                  90

Ile Gly Lys Ile Tyr His Ser Leu Thr Tyr Gly Gly Val Thr Lys Glu
             95                 100                 105

Asn Val Phe Asn Val Leu Ser Thr Asp Asn Lys Asn Tyr Ile Ile Gly
        110                 115                 120

Tyr Tyr Cys Lys Tyr Asp Glu Asp Lys Lys Gly His Gln Asp Phe Val
    125                 130                 135

Trp Val Leu Ser Arg Ser Met Val Leu Thr Gly Glu Ala Lys Thr Ala
140                 145                 150                 155

Val Glu Asn Tyr Leu Ile Gly Ser Pro Val Val Asp Ser Gln Lys Leu
                160                 165                 170

Val Tyr Ser Asp Phe Ser Glu Ala Ala Cys Lys Val Asn Asn Ser Asn
            175                 180                 185

Trp Ser His Pro Gln Phe Glu Lys
        190                 195

<210> SEQ ID NO 44
<211> LENGTH: 216
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 44
```

```
Met Lys Lys Thr Ala Ile Ala Ile Ala Val Ala Leu Ala Gly Phe Ala
    -20             -15             -10

Thr Val Ala Gln Ala Asp Val Tyr His Asp Gly Ala Cys Pro Glu Val
 -5         -1   1              5                      10

Lys Pro Val Asp Asn Phe Asp Trp Ser Gln Tyr His Gly Lys Trp Trp
            15              20              25

Glu Val Ala Lys Tyr Pro Asn Ser Val Glu Lys Tyr Gly Lys Cys Gly
            30              35              40

Trp Ala Glu Tyr Thr Pro Glu Gly Lys Ser Val Lys Val Ser Asn Tyr
        45              50              55

His Val Ile His Gly Lys Glu Tyr Phe Ile Glu Gly Thr Ala Tyr Pro
60              65              70                      75

Val Gly Asp Ser Lys Ile Gly Lys Ile Tyr His Ser Leu Thr Tyr Gly
                80              85                  90

Gly Val Thr Lys Glu Asn Val Phe Asn Val Leu Ser Thr Asp Asn Lys
            95              100             105

Asn Tyr Ile Ile Gly Tyr Tyr Cys Lys Tyr Asp Glu Asp Lys Lys Gly
            110             115             120

His Gln Asp Phe Val Trp Val Leu Ser Arg Ser Met Val Leu Thr Gly
        125             130             135

Glu Ala Lys Thr Ala Val Glu Asn Tyr Leu Ile Gly Ser Pro Val Val
140             145             150             155

Asp Ser Gln Lys Leu Val Tyr Ser Asp Phe Ser Glu Ala Ala Cys Lys
            160             165             170

Val Asn Asp Ala Ser Met Thr Gly Gly Gln Gln Met Gly Ser Ala
            175             180             185

Trp Ser His Pro Gln Phe Glu Lys
            190             195

<210> SEQ ID NO 45
<211> LENGTH: 397
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 45

Met Lys Lys Thr Ala Ile Ala Ile Ala Val Ala Leu Ala Gly Phe Ala
    -20             -15             -10

Thr Val Ala Gln Ala Asp Ala Ser Met Thr Gly Gly Gln Gln Met Gly
 -5         -1   1              5                      10

Asp Val Tyr His Asp Gly Ala Cys Pro Glu Val Lys Pro Val Asp Asn
            15              20              25

Phe Asp Trp Ser Gln Tyr His Gly Lys Trp Trp Glu Val Ala Lys Tyr
            30              35              40

Pro Asn Ser Val Glu Lys Tyr Gly Asn Cys Gly Trp Ala Glu Tyr Thr
        45              50              55

Pro Glu Gly Lys Ser Val Lys Val Ser Asn Tyr His Val Ile His Gly
60              65              70                      75

Lys Glu Tyr Phe Ile Glu Gly Thr Ala Tyr Pro Val Gly Asp Ser Lys
            80              85                  90

Ile Gly Lys Ile Tyr His Ser Leu Thr Tyr Gly Gly Val Thr Lys Glu
            95              100             105

Asn Val Phe Asn Val Leu Ser Thr Asp Asn Lys Asn Tyr Ile Ile Gly
```

```
                110                 115                 120
Tyr Tyr Cys Lys Tyr Asp Glu Asp Lys Lys Gly His Gln Asp Phe Val
        125                 130                 135

Trp Val Leu Ser Arg Ser Met Val Leu Thr Gly Glu Ala Lys Thr Ala
140                 145                 150                 155

Val Glu Asn Tyr Leu Ile Gly Ser Pro Val Val Asp Ser Gln Lys Leu
                160                 165                 170

Val Tyr Ser Asp Phe Ser Glu Ala Ala Cys Lys Val Asn Asn Gln Ala
                175                 180                 185

Gly Gly Gly Ser Gly Gly Gly Ser Gly Gly Gly Ser Glu Gly Gly Gly
                190                 195                 200

Ser Glu Gly Gly Gly Ser Glu Gly Gly Ser Glu Gly Gly Gly Ser
        205                 210                 215

Gly Gly Gly Ser Gly Ser Gly Asp Phe Asp Tyr Glu Lys Met Ala Asn
220                 225                 230                 235

Ala Asn Lys Gly Ala Met Thr Glu Asn Ala Asp Glu Asn Ala Leu Gln
                240                 245                 250

Ser Asp Ala Lys Gly Lys Leu Asp Ser Val Ala Thr Asp Tyr Gly Ala
                255                 260                 265

Ala Ile Asp Gly Phe Ile Gly Asp Val Ser Gly Leu Ala Asn Gly Asn
                270                 275                 280

Gly Ala Thr Gly Asp Phe Ala Gly Ser Asn Ser Gln Met Ala Gln Val
                285                 290                 295

Gly Asp Gly Asp Asn Ser Pro Leu Met Asn Asn Phe Arg Gln Tyr Leu
300                 305                 310                 315

Pro Ser Leu Pro Gln Ser Val Glu Cys Arg Pro Phe Val Phe Gly Ala
                320                 325                 330

Gly Lys Pro Tyr Glu Phe Ser Ile Asp Cys Asp Lys Ile Asn Leu Phe
                335                 340                 345

Arg Gly Val Phe Ala Phe Leu Leu Tyr Val Ala Thr Phe Met Tyr Val
                350                 355                 360

Phe Ser Thr Phe Ala Asn Ile Leu Arg Asn Lys Glu Ser
        365                 370                 375

<210> SEQ ID NO 46
<211> LENGTH: 255
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 46

Met Lys Lys Thr Ala Ile Ala Ile Ala Val Ala Leu Ala Gly Phe Ala
        -20                 -15                 -10

Thr Val Ala Gln Ala Asp Val Tyr His Asp Gly Ala Cys Pro Glu Val
        -5              -1   1               5                  10

Lys Pro Val Asp Asn Phe Asp Trp Ser Gln Tyr His Gly Lys Trp Trp
                15                  20                  25

Glu Val Ala Lys Tyr Pro Asn Ser Val Glu Lys Tyr Gly Lys Cys Gly
                30                  35                  40

Trp Ala Glu Tyr Thr Pro Glu Gly Lys Ser Val Lys Val Ser Asn Tyr
        45                  50                  55

His Val Ile His Gly Lys Glu Tyr Phe Ile Glu Gly Thr Ala Tyr Pro
60                  65                  70                  75
```

```
Val Gly Asp Ser Lys Ile Gly Lys Ile Tyr His Ser Leu Thr Tyr Gly
            80                  85                  90

Gly Val Thr Lys Glu Asn Val Phe Asn Val Leu Ser Thr Asp Asn Lys
        95                 100                 105

Asn Tyr Ile Ile Gly Tyr Tyr Cys Lys Tyr Asp Glu Asp Lys Lys Gly
                110                 115                 120

His Gln Asp Phe Val Trp Val Leu Ser Arg Ser Met Val Leu Thr Gly
        125                 130                 135

Glu Ala Lys Thr Ala Val Glu Asn Tyr Leu Ile Gly Ser Pro Val Val
140                 145                 150                 155

Asp Ser Gln Lys Leu Val Tyr Ser Asp Phe Ser Glu Ala Ala Cys Lys
                160                 165                 170

Val Asn Asn Ser Asn Trp Ser His Pro Gln Phe Glu Lys Gln Pro Ala
                175                 180                 185

Ser Leu Ala Glu Ala Lys Val Leu Ala Asn Arg Glu Leu Asp Lys Tyr
                190                 195                 200

Gly Val Ser Asp Tyr Tyr Lys Asn Leu Ile Asn Asn Ala Lys Thr Val
        205                 210                 215

Glu Gly Val Lys Ala Leu Ile Asp Glu Ile Leu Ala Ala Leu Pro
220                 225                 230

<210> SEQ ID NO 47
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 47

Asp Val Tyr His Asp Gly Ala Cys Pro Glu Val Lys Pro Val Asp Asn
 1               5                  10                  15

Phe Asp Trp Ser Gln Tyr His Gly Lys Trp Trp Glu Val Ala Lys Tyr
            20                  25                  30

Pro Asn Gln Glu Glu Leu Arg Gly Lys Cys Gly Trp Ala Glu Tyr Thr
        35                  40                  45

Pro Glu Gly Lys Ser Val Lys Val Ser Asn Tyr His Val Ile Arg Ala
    50                  55                  60

Gln Glu Ser Phe Ile Glu Gly Ser Ala Tyr Pro Val Gly Asp Ser Lys
65                  70                  75                  80

Ile Gly Lys Ile Tyr His Ser Leu Thr Tyr Phe Gly Leu Thr Lys Glu
                85                  90                  95

Asn Val Phe Asn Val Leu Ser Thr Asp Asn Lys Asn Tyr Ile Ile Gly
            100                 105                 110

Tyr Tyr Cys Ala Tyr Arg Glu Leu Leu Lys Gly His Gly Asp Phe Val
        115                 120                 125

Trp Val Leu Ser Arg Ser Met Val Leu Thr Gly Glu Ala Lys Thr Ala
    130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

<210> SEQ ID NO 48
<211> LENGTH: 173
<212> TYPE: PRT
<213> ORGANISM: Artificial Sequence
```

```
<220> FEATURE:
<223> OTHER INFORMATION: Description of Artificial Sequence: Synthetic
      construct

<400> SEQUENCE: 48

Asp Val Tyr His Asp Gly Ala Cys Pro Glu Val Lys Pro Val Asp Asn
 1               5                  10                  15

Phe Asp Trp Ser Gln Tyr His Gly Lys Trp Trp Glu Val Ala Lys Tyr
                20                  25                  30

Pro Asn Val Gln Glu Trp Thr Gly Lys Cys Gly Trp Ala Glu Tyr Thr
            35                  40                  45

Pro Glu Gly Lys Ser Val Lys Val Ser Asn Tyr His Val Ile Ser Phe
50                  55                  60

Lys Glu Arg Phe Glu Gly Thr Ala Tyr Pro Val Gly Asp Pro Lys Ile
65                  70                  75                  80

Gly Lys Ile Tyr His Ser Leu Thr Leu Arg Gly Trp Thr Lys Glu Asn
                85                  90                  95

Val Phe Asn Val Leu Ser Thr Asp Asn Lys Asn Tyr Ile Ile Gly Tyr
            100                 105                 110

Tyr Cys Thr Tyr Arg Glu Trp Ala Lys Gly His Phe Asp Phe Val Trp
        115                 120                 125

Val Leu Ser Arg Ser Met Val Leu Thr Gly Glu Ala Lys Thr Ala Val
130                 135                 140

Glu Asn Tyr Leu Ile Gly Ser Pro Val Val Asp Ser Gln Lys Leu Val
145                 150                 155                 160

Tyr Ser Asp Phe Ser Glu Ala Ala Cys Lys Val Asn Asn
                165                 170

<210> SEQ ID NO 49
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 49

Asp Val Tyr His Asp Gly Ala Cys Pro Glu Val Lys Pro Val Asp Asn
 1               5                  10                  15

Phe Asp Trp Ser Gln Tyr His Gly Lys Trp Trp Glu Val Ala Lys Tyr
                20                  25                  30

Pro Asn Gln Gly Glu Pro Pro Gly Lys Cys Gly Trp Ala Glu Tyr Thr
            35                  40                  45

Pro Glu Gly Lys Ser Val Lys Val Ser Asn Tyr His Val Ile Ser Arg
50                  55                  60

Tyr Glu Arg Phe Ile Glu Gly Thr Ala Tyr Pro Val Gly Asp Ser Lys
65                  70                  75                  80

Ile Gly Lys Ile Tyr His Ser Leu Thr Val Gly Gly Tyr Thr Lys Glu
                85                  90                  95

Asn Val Phe Asn Val Leu Ser Thr Asp Asn Lys Asn Tyr Ile Ile Gly
            100                 105                 110

Tyr Tyr Cys Ser Tyr Leu Glu Tyr Leu Lys Gly His Leu Asp Phe Gly
        115                 120                 125

Trp Val Leu Ser Arg Ser Met Val Leu Thr Gly Glu Ala Lys Thr Ala
130                 135                 140

Val Glu Asn Tyr Leu Ile Gly Ser Pro Val Val Asp Ser Gln Lys Leu
145                 150                 155                 160
```

Val Tyr Ser Asp Phe Ser Glu Ala Ala Cys Lys Val Asn Asn
            165                 170

<210> SEQ ID NO 50
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 50

Asp Val Tyr His Asp Gly Ala Cys Pro Glu Val Lys Pro Val Asp Asn
 1               5                  10                  15

Phe Asp Trp Ser Gln Tyr His Gly Lys Trp Trp Glu Val Ala Lys Tyr
            20                  25                  30

Pro Asn Arg Arg Glu Lys Phe Gly Lys Cys Gly Trp Ala Glu Tyr Thr
        35                  40                  45

Pro Glu Gly Lys Ser Val Lys Val Ser Asn Tyr His Val Ile Arg Trp
 50                  55                  60

Gly Glu Arg Phe Ile Glu Gly Thr Ala Tyr Pro Val Gly Asp Ser Lys
 65                  70                  75                  80

Ile Gly Lys Ile Tyr His Ser Leu Thr Leu Pro Gly Tyr Thr Lys Glu
                85                  90                  95

Asn Val Phe Asn Val Leu Ser Thr Asp Asn Lys Asn Tyr Ile Ile Gly
            100                 105                 110

Tyr Tyr Cys Lys Tyr Leu Glu Arg Leu Lys Gly His Ala Asp Phe Val
        115                 120                 125

Trp Val Leu Ser Arg Ser Met Val Leu Thr Gly Glu Ala Lys Thr Ala
    130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
            165                 170

<210> SEQ ID NO 51
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 51

Asp Val Tyr His Asp Gly Ala Cys Pro Glu Val Lys Pro Val Asp Asn
 1               5                  10                  15

Phe Asp Trp Ser Gln Tyr His Gly Lys Trp Trp Glu Val Ala Lys Tyr
            20                  25                  30

Pro Asn Gly Gly Glu Ser Pro Gly Lys Cys Gly Trp Ala Glu Tyr Thr
        35                  40                  45

Pro Glu Gly Lys Ser Val Lys Val Ser Asn Tyr His Val Ile Lys Lys
 50                  55                  60

Arg Glu Arg Phe Ile Glu Gly Thr Ala Tyr Pro Val Gly Asp Ser Lys
 65                  70                  75                  80

Ile Gly Lys Ile Cys His Ser Leu Thr Trp Ser Gly Leu Thr Lys Glu
                85                  90                  95

Asn Val Phe Asn Val Leu Ser Thr Asp Asn Lys Asn Tyr Ile Ile Gly
            100                 105                 110

Tyr Tyr Cys Lys Tyr Lys Glu Arg Lys Gly His Gly Asp Phe Val
            115                 120                 125

Trp Val Leu Ser Arg Ser Met Val Leu Thr Gly Glu Ala Lys Thr Ala
        130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

<210> SEQ ID NO 52
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 52

Asp Val Tyr His Asp Gly Ala Cys Pro Glu Val Lys Pro Val Asp Asn
1               5                   10                  15

Phe Asp Trp Ser Gln Tyr His Gly Lys Trp Trp Glu Val Ala Lys Tyr
            20                  25                  30

Pro Asn Gln Lys Glu Lys Trp Gly Lys Cys Gly Trp Ala Glu Tyr Thr
        35                  40                  45

Pro Glu Gly Lys Ser Val Lys Val Ser Asn Tyr His Val Ile Lys Arg
    50                  55                  60

Pro Glu Arg Phe Ile Glu Gly Thr Ala Tyr Pro Val Gly Asp Ser Lys
65                  70                  75                  80

Ile Gly Lys Ile Tyr His Ser Leu Thr Arg Leu Gly Lys Thr Lys Glu
                85                  90                  95

Asn Val Phe Asn Val Leu Ser Thr Asp Asn Lys Asn Tyr Ile Ile Gly
            100                 105                 110

Tyr Tyr Cys Leu Tyr Pro Glu Gly Trp Lys Gly His Lys Asp Phe Val
        115                 120                 125

Trp Val Leu Ser Arg Ser Met Val Leu Thr Gly Glu Ala Lys Thr Ala
    130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

<210> SEQ ID NO 53
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 53

Asp Val Tyr His Asp Gly Ala Cys Pro Glu Val Lys Pro Val Asp Asn
1               5                   10                  15

Phe Asp Trp Ser Gln Tyr His Gly Lys Trp Trp Glu Val Ala Lys Tyr
            20                  25                  30

Pro Ser Lys Lys Gly Lys Gln Gly Lys Cys Gly Trp Ala Glu Tyr Thr
        35                  40                  45

Pro Glu Gly Lys Ser Val Lys Val Ser Arg Tyr Asp Val Ile Pro Cys
    50                  55                  60

```
Leu Glu Ser Phe Met Glu Gly Thr Ala Tyr Pro Val Gly Asp Ser Lys
 65                  70                  75                  80

Ile Gly Lys Ile Tyr His Ser Arg Thr Lys Pro Gly Arg Thr Lys Lys
                 85                  90                  95

Thr Val Phe Asn Val Pro Ser Thr Asp Asn Lys Asn Tyr Ile Ile Gly
            100                 105                 110

Tyr Ser Cys Val Tyr Pro Glu Gly Arg Lys Gly His Arg Asp His Val
            115                 120                 125

Trp Val Leu Ser Arg Ser Met Val Leu Thr Gly Glu Ala Lys Thr Ala
        130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

<210> SEQ ID NO 54
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 54

Asp Val Tyr His Asp Gly Ala Cys Pro Glu Val Lys Pro Val Asp Asn
  1               5                  10                  15

Phe Asp Trp Ser Gln Tyr His Gly Lys Trp Trp Glu Val Ala Lys Tyr
                 20                  25                  30

Pro Ser Asn Arg Gly Ser Lys Gly Lys Cys Gly Trp Ala Glu Tyr Thr
             35                  40                  45

Pro Glu Gly Lys Ser Val Lys Val Ser Arg Tyr Asp Val Ile Pro Arg
         50                  55                  60

Leu Glu Ala Phe Met Glu Gly Thr Ala Tyr Pro Val Gly Asp Ser Lys
 65                  70                  75                  80

Ile Gly Lys Ile Tyr His Ser Arg Thr Ser Lys Gly Lys Thr Lys Lys
                 85                  90                  95

Thr Val Phe Asn Val Leu Ser Thr Asp Asn Lys Asn Tyr Ile Ile Gly
            100                 105                 110

Tyr Ser Cys Ile Tyr Asn Glu Arg Tyr Lys Gly His Tyr Asp His Val
            115                 120                 125

Trp Val Leu Ser Arg Ser Met Val Leu Thr Gly Glu Ala Lys Thr Ala
        130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

<210> SEQ ID NO 55
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 55

Asp Val Tyr His Asp Gly Ala Cys Pro Glu Val Lys Pro Val Asp Asn
  1               5                  10                  15
```

```
Phe Asp Trp Ser Gln Tyr His Gly Lys Trp Trp Glu Val Ala Lys Tyr
             20                  25                  30

Pro Ser Lys Gly Gly Glu Lys Gly Lys Cys Gly Trp Ala Glu Tyr Thr
             35                  40                  45

Pro Glu Gly Lys Ser Val Lys Val Ser Arg Tyr Asp Val Ile Leu Ser
 50                  55                  60

Ser Glu Pro Phe Met Glu Gly Thr Ala Tyr Pro Val Gly Asp Ser Lys
 65                  70                  75                  80

Ile Gly Lys Ile Tyr His Ser Arg Thr Lys Lys Gly Glu Thr Lys Lys
                 85                  90                  95

Thr Val Phe Asn Val Leu Ser Thr Asp Asn Lys Asn Tyr Ile Ile Gly
                100                 105                 110

Tyr Ser Cys Gly Tyr Cys Glu Cys Arg Lys Gly His Ala Asp His Val
                115                 120                 125

Trp Val Leu Ser Arg Ser Met Val Leu Thr Gly Glu Ala Lys Thr Ala
            130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

<210> SEQ ID NO 56
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 56

Asp Val Tyr His Asp Gly Ala Cys Pro Glu Val Lys Pro Val Asp Asn
  1               5                  10                  15

Phe Asp Trp Ser Gln Tyr His Gly Lys Trp Trp Glu Val Ala Lys Cys
             20                  25                  30

Pro Ser Gly Lys Gly Arg Ala Gly Lys Cys Gly Trp Ala Glu Phe Thr
             35                  40                  45

Pro Glu Gly Lys Ser Val Lys Val Ser Arg Tyr Asp Val Ile Pro Ala
 50                  55                  60

Pro Glu Leu Phe Met Glu Gly Thr Ala Tyr Pro Val Gly Asp Pro Lys
 65                  70                  75                  80

Ile Gly Lys Ile Tyr His Ser Arg Thr Asn Lys Gly Leu Thr Lys Lys
                 85                  90                  95

Thr Val Phe Asn Val Leu Ser Thr Asp Asn Lys Asn Tyr Ile Ile Gly
                100                 105                 110

Tyr Ser Cys Lys Tyr Gly Glu Asp Gln Lys Gly His Lys Asp His Val
                115                 120                 125

Trp Val Leu Ser Arg Ser Met Val Leu Thr Gly Glu Ala Lys Thr Ala
            130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

<210> SEQ ID NO 57
<211> LENGTH: 133
<212> TYPE: PRT
```

```
<213> ORGANISM: Artificial Sequence
<220> FEATURE:
<223> OTHER INFORMATION: Description of Artificial Sequence: Synthetic
      construct

<400> SEQUENCE: 57

Met Lys Lys Thr Ala Ile Ala Ile Ala Val Ala Leu Ala Gly Phe Ala
    -20                 -15                 -10

Thr Val Ala Gln Ala Ala Lys Lys Val Val Leu Gly Lys Lys Gly Asp
 -5              -1   1               5                      10

Thr Val Glu Leu Thr Cys Thr Ala Ser Gln Lys Lys Ser Ile Gln Phe
                 15                  20                  25

His Trp Lys Asn Ser Asn Gln Ile Lys Ile Leu Gly Asn Gln Gly Ser
             30                  35                  40

Phe Leu Thr Lys Gly Pro Ser Lys Leu Asn Asp Arg Ala Asp Ser Arg
         45                  50                  55

Arg Ser Leu Trp Asp Gln Gly Asn Phe Pro Leu Ile Ile Lys Asn Leu
 60                  65                  70                  75

Lys Ile Glu Asp Ser Asp Thr Tyr Ile Cys Glu Val Glu Asp Gln Lys
                 80                  85                  90

Glu Glu Val Gln Leu Leu Val Phe Gly Leu Thr Ser Ala Trp Ser His
             95                 100                 105

Pro Gln Phe Glu Lys
            110

<210> SEQ ID NO 58
<211> LENGTH: 114
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 58

Met Lys Lys Thr Ala Ile Ala Ile Ala Val Ala Leu Ala Gly Phe Ala
    -20                 -15                 -10

Thr Val Ala Gln Ala Ala Asn Ser Asp Thr His Leu Leu Gln Gly Gln
 -5              -1   1               5                      10

Ser Leu Thr Leu Thr Leu Glu Ser Pro Pro Gly Ser Ser Pro Ser Val
                 15                  20                  25

Gln Cys Arg Ser Pro Arg Gly Lys Asn Ile Gln Gly Gly Lys Thr Leu
             30                  35                  40

Ser Val Ser Gln Leu Glu Leu Gln Asp Ser Gly Thr Trp Thr Cys Thr
         45                  50                  55

Val Leu Gln Asn Gln Lys Lys Val Glu Phe Lys Ile Asp Ile Val Val
 60                  65                  70                  75

Leu Ala Phe Gln Lys Ala Ser Ser Ser Ala Trp Ser His Pro Gln Phe
                 80                  85                  90

Glu Lys

<210> SEQ ID NO 59
<211> LENGTH: 216
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 59
```

```
Met Lys Lys Thr Ala Ile Ala Ile Ala Val Ala Leu Ala Gly Phe Ala
    -20             -15              -10

Thr Val Ala Gln Ala Ala Lys Lys Val Val Leu Gly Lys Lys Gly Asp
 -5          -1   1              5                      10

Thr Val Glu Leu Thr Cys Thr Ala Ser Gln Lys Lys Ser Ile Gln Phe
            15               20               25

His Trp Lys Asn Ser Asn Gln Ile Lys Ile Leu Gly Asn Gln Gly Ser
        30               35               40

Phe Leu Thr Lys Gly Pro Ser Lys Leu Asn Asp Arg Ala Asp Ser Arg
        45               50              55

Arg Ser Leu Trp Asp Gln Gly Asn Phe Pro Leu Ile Ile Lys Asn Leu
 60              65               70                      75

Lys Ile Glu Asp Ser Asp Thr Tyr Ile Cys Glu Val Glu Asp Gln Lys
            80               85               90

Glu Glu Val Gln Leu Leu Val Phe Gly Leu Thr Ala Asn Ser Asp Thr
            95              100              105

His Leu Leu Gln Gly Gln Ser Leu Thr Leu Thr Leu Glu Ser Pro Pro
           110              115              120

Gly Ser Ser Pro Ser Val Gln Cys Arg Ser Pro Arg Gly Lys Asn Ile
    125              130              135

Gln Gly Gly Lys Thr Leu Ser Val Ser Gln Leu Glu Leu Gln Asp Ser
140              145              150              155

Gly Thr Trp Thr Cys Thr Val Leu Gln Asn Gln Lys Lys Val Glu Phe
            160              165              170

Lys Ile Asp Ile Val Val Leu Ala Phe Gln Lys Ala Ser Ser Ser Ala
            175              180              185

Trp Ser His Pro Gln Phe Glu Lys
        190              195

<210> SEQ ID NO 60
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 60

Asp Val Tyr His Asp Gly Ala Cys Pro Glu Val Lys Pro Val Asp Asn
 1               5                  10                  15

Phe Asp Trp Ser Gln Tyr His Gly Lys Trp Trp Glu Val Ala Lys Tyr
            20                  25                  30

Pro Asn Gln Ile Glu Gln Gly Gly Lys Cys Gly Trp Ala Glu Tyr Thr
            35                  40                  45

Pro Glu Gly Lys Ser Val Lys Val Ser Asn Tyr His Val Ile Tyr Ala
 50                  55                  60

Ser Glu Asp Phe Ile Glu Gly Thr Ala Tyr Pro Val Gly Asp Ser Lys
 65                  70                  75                  80

Ile Gly Lys Ile Tyr His Ser Leu Thr Ser Ser Gly Val Thr Lys Glu
                 85                  90                  95

Asn Val Phe Asn Val Leu Ser Thr Asp Asn Lys Asn Tyr Ile Ile Gly
            100                 105                 110

Tyr Tyr Cys Gly Tyr Arg Glu Ala Pro Lys Gly His Met Asp Phe Val
            115                 120                 125

Trp Val Leu Ser Arg Ser Met Val Leu Thr Gly Glu Ala Lys Thr Ala
130                 135                 140
```

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

<210> SEQ ID NO 61
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 61

Asp Val Tyr His Asp Gly Ala Cys Pro Glu Val Lys Pro Val Asp Asn
1               5                   10                  15

Phe Asp Trp Ser Gln Tyr His Gly Lys Trp Trp Glu Val Ala Lys Tyr
                20                  25                  30

Pro Asn Gly Thr Glu Glu Ser Gly Lys Cys Gly Trp Ala Glu Tyr Thr
            35                  40                  45

Pro Glu Gly Lys Ser Val Lys Val Ser Asn Tyr His Val Ile Thr Gln
    50                  55                  60

Gly Glu Lys Phe Ile Glu Gly Thr Ala Tyr Pro Val Gly Asp Ser Lys
65                  70                  75                  80

Ile Gly Lys Ile Tyr His Ser Leu Thr Arg Pro Gly Leu Thr Lys Glu
                85                  90                  95

Asn Val Phe Asn Val Leu Ser Thr Asp Asn Lys Asn Tyr Ile Ile Gly
            100                 105                 110

Tyr Tyr Cys Asp Tyr Met Glu Cys Lys Lys Gly His Glu Asp Phe Val
        115                 120                 125

Trp Val Leu Ser Arg Ser Met Val Leu Thr Gly Glu Ala Lys Thr Ala
    130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

<210> SEQ ID NO 62
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 62

Asp Val Tyr His Asp Gly Ala Cys Pro Glu Val Lys Pro Val Asp Asn
1               5                   10                  15

Phe Asp Trp Ser Gln Tyr His Gly Lys Trp Trp Glu Val Ala Lys Tyr
                20                  25                  30

Pro Asn Trp Leu Glu Leu Glu Gly Lys Cys Gly Trp Ala Glu Tyr Thr
            35                  40                  45

Pro Glu Gly Lys Ser Val Lys Val Ser Asn Tyr His Val Ile Met Gln
    50                  55                  60

Gln Glu Leu Phe Ile Glu Gly Thr Ala Tyr Pro Val Gly Asp Ser Lys
65                  70                  75                  80

Ile Gly Lys Ile Tyr His Ser Leu Thr Val Pro Gly Gln Thr Lys Glu
                85                  90                  95

```
Asn Val Phe Asn Val Leu Ser Thr Asp Asn Lys Asn Tyr Ile Ile Gly
            100                 105                 110

Tyr Tyr Cys Phe Tyr Pro Glu Asp Ala Lys Gly His Val Asp Phe Val
        115                 120                 125

Trp Val Leu Ser Arg Ser Met Val Leu Thr Gly Glu Ala Lys Thr Ala
    130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170
```

<210> SEQ ID NO 63
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 63

```
Asp Val Tyr His Asp Gly Ala Cys Pro Glu Val Lys Pro Val Asp Asn
1               5                   10                  15

Phe Asp Trp Ser Gln Tyr His Gly Lys Trp Trp Glu Val Ala Lys Tyr
            20                  25                  30

Pro Asn Ser His Glu Thr Gly Gly Lys Cys Gly Trp Ala Glu Tyr Thr
        35                  40                  45

Pro Glu Gly Lys Ser Val Lys Val Ser Asn Tyr His Val Ile Thr Pro
    50                  55                  60

His Glu Arg Phe Ile Glu Gly Thr Ala Tyr Pro Val Gly Asp Ser Lys
65                  70                  75                  80

Ile Gly Lys Ile Tyr His Ser Leu Thr Trp Ile Gly Thr Thr Lys Glu
                85                  90                  95

Asn Val Phe Asn Val Leu Ser Thr Asp Asn Lys Asn Tyr Ile Ile Gly
            100                 105                 110

Tyr Tyr Cys Ser Tyr Ser Glu Ala Gly Lys Gly His Gln Asp Phe Val
        115                 120                 125

Trp Val Leu Ser Arg Ser Met Val Leu Thr Gly Glu Ala Lys Thr Ala
    130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170
```

<210> SEQ ID NO 64
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 64

```
Asp Val Tyr His Asp Gly Ala Cys Pro Glu Val Lys Pro Val Asp Asn
1               5                   10                  15

Phe Asp Trp Ser Gln Tyr His Gly Lys Trp Trp Glu Val Ala Lys Tyr
            20                  25                  30

Pro Asn Val Thr Glu Ile Pro Gly Lys Cys Gly Trp Ala Glu Tyr Thr
        35                  40                  45
```

```
Pro Glu Gly Lys Ser Val Lys Val Ser Asn Tyr His Val Ile Met Ser
        50                  55                  60

Phe Glu Pro Phe Ile Glu Gly Thr Ala Tyr Pro Val Gly Asp Ser Lys
 65                  70                  75                  80

Ile Gly Lys Ile Tyr His Ser Leu Thr Ser Tyr Gly Gln Thr Lys Glu
                 85                  90                  95

Asn Val Phe Asn Val Leu Ser Thr Asp Asn Lys Asn Tyr Ile Ile Gly
            100                 105                 110

Tyr Tyr Cys Glu Tyr Met Glu Ser Ser Lys Gly His Lys Asp Phe Val
        115                 120                 125

Trp Val Leu Ser Arg Ser Met Val Leu Thr Gly Glu Ala Lys Thr Ala
    130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170
```

<210> SEQ ID NO 65
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 65

```
Asp Val Tyr His Asp Gly Ala Cys Pro Glu Val Lys Pro Val Asp Asn
 1               5                  10                  15

Phe Asp Trp Ser Gln Tyr His Gly Lys Trp Trp Glu Val Ala Lys Tyr
            20                  25                  30

Pro Asn Pro Glu Glu Gln Glu Gly Lys Cys Gly Trp Ala Glu Tyr Thr
        35                  40                  45

Pro Glu Gly Lys Ser Val Lys Val Ser Asn Tyr His Val Ile Thr Thr
    50                  55                  60

Ala Glu Asn Phe Ile Glu Gly Thr Ala Tyr Pro Val Gly Asp Ser Lys
 65                  70                  75                  80

Ile Gly Lys Ile Tyr His Ser Leu Thr Trp Arg Gly Ile Thr Lys Glu
                 85                  90                  95

Asn Val Phe Asn Val Leu Ser Thr Asp Asn Lys Asn Tyr Ile Ile Gly
            100                 105                 110

Tyr Tyr Cys Ser Tyr Arg Glu Trp Phe Lys Gly His Phe Asp Phe Val
        115                 120                 125

Trp Val Leu Ser Arg Ser Met Val Leu Thr Gly Glu Ala Lys Thr Ala
    130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170
```

<210> SEQ ID NO 66
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 66

Asp Val Tyr His Asp Gly Ala Cys Pro Glu Val Lys Pro Val Asp Asn
1               5                   10                  15

Phe Asp Trp Ser Gln Tyr His Gly Lys Trp Trp Glu Val Ala Lys Tyr
            20                  25                  30

Pro Asn Thr Ser Glu His Ser Gly Lys Cys Gly Trp Ala Glu Tyr Thr
            35                  40                  45

Pro Glu Gly Lys Ser Val Lys Val Ser Asn Tyr His Val Ile Lys Lys
        50                  55                  60

Lys Glu Arg Phe Ile Glu Gly Thr Ala Tyr Ser Ala Gly Asp Ser Lys
65              70                  75                  80

Ile Gly Lys Ile Tyr His Ser Leu Thr Ser Val Gly Lys Thr Lys Glu
                85                  90                  95

Asn Val Phe Asn Val Leu Ser Thr Asp Asn Lys Asn Tyr Ile Ile Gly
                100                 105                 110

Tyr Tyr Cys Ser Tyr Lys Glu Lys Thr Lys Gly His Gly Asp Phe Val
            115                 120                 125

Trp Val Leu Ser Arg Ser Met Val Leu Thr Gly Glu Ala Lys Thr Ala
130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

<210> SEQ ID NO 67
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 67

Asp Val Tyr His Asp Gly Ala Cys Pro Glu Val Lys Pro Val Asp Asn
1               5                   10                  15

Phe Asp Trp Ser Gln Tyr His Gly Lys Trp Trp Glu Val Ala Lys Tyr
            20                  25                  30

Pro Asn Ala Lys Glu Ser Pro Gly Lys Cys Gly Trp Ala Glu Tyr Thr
            35                  40                  45

Pro Glu Gly Lys Ser Val Lys Val Ser Asn Tyr His Val Ile Gln Arg
        50                  55                  60

Leu Glu Gly Phe Ile Glu Gly Thr Ala Tyr Pro Val Gly Asp Ser Lys
65              70                  75                  80

Ile Gly Lys Ile Tyr His Ser Leu Thr Thr Trp Gly Leu Thr Lys Glu
                85                  90                  95

Asn Val Phe Asn Val Leu Ser Thr Asp Asn Lys Asn Tyr Ile Ile Gly
                100                 105                 110

Tyr Tyr Cys Gly Tyr Val Glu Lys Ser Lys Gly His Pro Asp Phe Val
            115                 120                 125

Trp Val Leu Ser Arg Ser Met Val Leu Thr Gly Glu Ala Lys Thr Ala
130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

```
<210> SEQ ID NO 68
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 68

Asp Val Tyr His Asp Gly Ala Cys Pro Glu Val Lys Pro Val Asp Asn
 1               5                  10                  15

Phe Asp Trp Ser Gln Tyr His Gly Lys Trp Trp Glu Val Ala Lys Tyr
                20                  25                  30

Pro Asn Met Thr Glu Val Lys Gly Lys Cys Gly Trp Ala Glu Tyr Thr
            35                  40                  45

Pro Glu Gly Lys Ser Val Lys Val Ser Asn Tyr His Val Ile Arg Glu
        50                  55                  60

Lys Glu Trp Phe Ile Glu Gly Thr Ala Tyr Pro Val Gly Asp Ser Lys
65                  70                  75                  80

Ile Gly Lys Ile Tyr His Ser Leu Thr Ile Ser Gly Leu Thr Lys Glu
                85                  90                  95

Asn Val Phe Asn Val Leu Ser Thr Asp Asp Lys Asn Tyr Ile Ile Gly
            100                 105                 110

Tyr Tyr Cys Lys Tyr Met Glu Leu Trp Lys Gly His Arg Asp Phe Val
        115                 120                 125

Trp Val Leu Ser Arg Ser Met Val Leu Thr Gly Glu Ala Lys Thr Ala
    130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

<210> SEQ ID NO 69
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 69

Asp Val Tyr His Asp Gly Ala Cys Pro Glu Val Lys Pro Val Asp Asn
 1               5                  10                  15

Phe Asp Trp Ser Gln Tyr His Gly Lys Trp Trp Glu Val Ala Lys Tyr
                20                  25                  30

Pro Asn Ile Ala Glu Leu Gly Gly Lys Cys Gly Trp Ala Glu Tyr Thr
            35                  40                  45

Pro Glu Gly Lys Ser Val Lys Val Ser Asn Tyr His Val Ile Asn Trp
        50                  55                  60

Asn Glu Met Phe Ile Glu Gly Thr Ala Tyr Pro Val Gly Asp Ser Lys
65                  70                  75                  80

Ile Gly Lys Ile Ser His Ser Leu Thr Lys Val Gly Gln Thr Lys Glu
                85                  90                  95

Asn Val Phe Asn Val Leu Ser Thr Asp Asn Lys Asn Tyr Ile Ile Gly
            100                 105                 110

Tyr Tyr Cys Gln Tyr Ser Glu Arg Ala Lys Gly His Leu Asp Phe Val
        115                 120                 125

Trp Val Leu Ser Arg Ser Met Val Leu Thr Gly Glu Ala Lys Thr Ala
```

```
            130                 135                 140
Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170
```

<210> SEQ ID NO 70
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 70

```
Asp Val Tyr His Asp Gly Ala Cys Pro Glu Val Lys Pro Val Asp Asn
1               5                   10                  15

Phe Asp Trp Ser Gln Tyr His Gly Lys Trp Trp Glu Val Ala Lys Tyr
            20                  25                  30

Pro Asn Lys Arg Glu Gly Arg Gly Lys Cys Gly Trp Ala Glu Tyr Thr
        35                  40                  45

Pro Glu Gly Lys Ser Val Lys Val Ser Asn Tyr His Val Ile Thr Gly
    50                  55                  60

Asn Glu Ile Phe Ile Glu Gly Thr Ala Tyr Pro Val Gly Asp Ser Lys
65                  70                  75                  80

Ile Gly Lys Ile Tyr Tyr Ser Leu Thr Lys Thr Gly Ser Thr Lys Glu
                85                  90                  95

Asn Val Phe Asn Val Leu Ser Thr Asp Asn Lys Asn Tyr Ile Ile Gly
            100                 105                 110

Tyr Tyr Cys Val Tyr Leu Glu Tyr Ser Lys Gly His Arg Asp Phe Val
        115                 120                 125

Trp Val Leu Ser Arg Ser Met Val Leu Thr Gly Glu Ala Lys Thr Ala
    130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170
```

<210> SEQ ID NO 71
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 71

```
Asp Val Tyr His Asp Gly Ala Cys Pro Glu Val Lys Pro Val Asp Asn
1               5                   10                  15

Phe Asp Trp Ser Gln Tyr His Gly Lys Trp Trp Glu Val Ala Lys Tyr
            20                  25                  30

Pro Asn Gly Asn Glu Leu Arg Gly Lys Cys Gly Trp Ala Glu Tyr Thr
        35                  40                  45

Pro Glu Gly Lys Ser Val Lys Val Ser Asn Tyr His Val Ile Asn Thr
    50                  55                  60

Ser Glu Gly Phe Ile Glu Gly Thr Ala Tyr Pro Val Gly Asp Ser Lys
65                  70                  75                  80

Ile Gly Lys Ile Tyr His Ser Leu Thr Asn Thr Gly Met Thr Lys Glu
```

-continued

```
                85                  90                  95
Asn Val Phe Asn Val Leu Ser Thr Asp Asn Lys Asn Tyr Ile Ile Gly
            100                 105                 110

Tyr Tyr Cys Ser Trp Glu Val Ser Lys Gly His His Asp Phe Val Trp
        115                 120                 125

Val Leu Ser Arg Ser Met Val Leu Thr Gly Glu Ala Lys Thr Ala Val
    130                 135                 140

Glu Asn Tyr Leu Ile Gly Ser Pro Val Val Asp Ser Gln Lys Leu Val
145                 150                 155                 160

Tyr Ser Asp Phe Ser Glu Ala Ala Cys Lys Val Asn Asn Ser
                165                 170

<210> SEQ ID NO 72
<211> LENGTH: 174
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 72

Asp Val Tyr His Asp Gly Ala Cys Pro Glu Val Lys Pro Val Asp Asn
1               5                   10                  15

Phe Asp Trp Ser Gln Tyr His Gly Lys Trp Trp Glu Val Ala Lys Tyr
            20                  25                  30

Pro Asn Arg Ala Glu Ile Gly Gly Lys Cys Gly Trp Ala Glu Tyr Thr
        35                  40                  45

Pro Glu Gly Lys Ser Val Lys Val Ser Asn Tyr His Val Ile Lys Gln
    50                  55                  60

Trp Glu Lys Phe Ile Glu Gly Thr Ala Tyr Pro Val Gly Asp Ser Lys
65                  70                  75                  80

Ile Gly Lys Ile Tyr His Ser Leu Thr Gly Thr Gly Ser Thr Lys Glu
                85                  90                  95

Asn Val Phe Asn Val Leu Ser Thr Asp Asn Lys Asn Tyr Ile Ile Gly
            100                 105                 110

Tyr Tyr Cys Asn Tyr His Glu Ser Arg Lys Gly His Arg Asp Phe Val
        115                 120                 125

Trp Val Leu Ser Arg Ser Met Val Leu Thr Gly Glu Ala Lys Thr Ala
    130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 73

His His His His His His
1               5
```

US 7,691,970 B2

MUTEINS OF A BILIN-BINDING PROTEIN WITH AFFINITY FOR A GIVEN TARGET

CROSS-REFERENCE TO RELATED APPLICATIONS

This application is a National Stage application of PCT/EP2003/009403, filed Aug. 25, 2003.

BACKGROUND OF THE INVENTION

The present invention relates to novel muteins derived from a bilin-binding protein (BBP) that binds a given target, for example a macromolecular target, with detectable affinity. In particular, the invention relates to a mutein of the bilin-binding protein of Pieris brassicae. The invention also refers to a corresponding nucleic acid molecule encoding such a mutein and to a method for its generation. The invention further refers to a method for producing such a mutein. Finally, the invention is directed to a pharmaceutical composition comprising such a lipocalin mutein as well as to various use of the mutein.

BRIEF SUMMARY OF THE INVENTION

The members of the lipocalin protein family (Pervaiz, S., and Brew, K. (1987) FASEB J. 1, 209-214) are typically small, secreted proteins which are characterized by a range of different molecular-recognition properties: their ability to bind various, principally hydrophobic molecules (such as retinoids, fatty acids, cholesterols, prostaglandins, biliverdins, pheromones, tastants, and odorants), their binding to specific cell-surface receptors and their formation of macromolecular complexes. Although they have, in the past, been classified primarily as transport proteins, it is now clear that the lipocalins fulfill a variety of physiological functions. These include roles in retinol transport, olfaction, pheromone signaling, and the synthesis of prostaglandins. The lipocalins have also been implicated in the regulation of the immune response and the mediation of cell homoeostasis (reviewed, for example, in Flower, D. R. (1996) Biochem. J. 318, 1-143 and in Flower, D. R. et al. (2000) Biochim. Biophys. Acta 1482, 9-24).

Proteins, which selectively bind to their corresponding targets by way of non-covalent interaction, play a crucial role as reagents in biotechnology, medicine, bioanalytics as well as in the biological and life sciences in general. Antibodies, i.e. immunoglobulins, are a prominent example of this class of proteins. Despite the manifold needs for such proteins in conjunction with recognition, binding and/or separation of ligands/targets, almost exclusively immunoglobulins are currently used. The application of other proteins with defined ligand-binding characteristics, for example the lectins, has remained restricted to special cases.

Rather recently, members of the lipocalin family have become subject of research concerning proteins having defined ligand-binding properties. The PCT publication WO 99/16873 discloses the class of ANTICALINS®; i.e. polypeptides of the lipocalin family, which exhibit, like antibodies, specific binding characteristics for a given ligand (cf. also Beste et al. (1999) Proc. Natl. Acad. Sci. USA 96, 1898-1903). ANTICALINS® are obtainable starting from polypeptides of the lipocalin family which are mutated in four segments that correspond to the sequence positions of the linear polypeptide sequence comprising amino acid positions 28 to 45, 58 to 69, 86 to 99 and 114 to 129 of the Bilin-binding protein (BBP) of Pieris brassicae.

The initial research on generating ANTICALINS® with novel ligand specificities focused on low molecular weight compounds such as fluorescein (cf., for example, WO 99/16873 or Beste et al., supra) or digoxigenin (cf., for example, PCT publication WO 00/75308 as well as Schlehuber et al. (J. Mol. Biol. (2000) 297, 1105-1120). For the generation of these hapten-binding ANTICALINS®, the bilin-binding protein of Pieris brassicae was subjected to mutagenesis at a set of 16 amino acid residues (sequence positions 34 to 37, 58, 60, 69, 88, 90, 93, 95, 97, 114, 116, 125, and 127).

Due to their potential to have antibody-like functions in recognizing prescribed ligands combined with their small size and advantageous biophysical properties, lipocalins have been regarded as attractive candidates for the design of such muteins, which should be valuable molecular tools in diagnostic as well as therapeutic applications. For examples, ANTICALINS® could be suitable candidates for binding macromolecular disease targets such as macromolecular antigens (target molecules) on the surface of tumor cells in cancer therapy.

Based on the generation of muteins of the bilin-binding protein of Pieris brassicae by mutating the above-mentioned 16 sequence positions, it was suggested that by adjusting the lipocalin library in an appropriate manner an extended area of surface complementarity and thus binding of macromolecular antigens may be realized in a manner as it is typical for the recognition of protein antigens by antibodies (Skerra, A (2000), Biochimica et Biophysica Acta 1482, 337-350). In accordance with this suggestion, apolipoprotein D was subjected to mutagenesis at 24 sequence positions in order to obtain muteins having detectable affinity for hemoglobin (International Patent Application WO 03/029471). Such muteins could indeed be obtained in WO 03/029471. However, with a dissociation constant of 2.2 µM, the binding affinity of these muteins was only in the micromolar range, and thus not sufficient for the use of these muteins in many applications in the biomedical field such as the binding to cell surface receptors or other disease targets.

Thus, it is an object of the present invention to provide novel lipocalin muteins having improved binding affinity for macromolecules.

DETAILED DESCRIPTION OF THE INVENTION

This object is accomplished amongst others by a mutein having the features of the independent claims as well as the method of its generation.

Such a mutein is a lipocalin mutein derived from a bilin-binding protein comprising at least one mutated amino acid residue at any of the sequence positions corresponding to the sequence positions 38, 39, 63, 64, 65, 67, 91, 118, 120, and 121 of the linear polypeptide sequence of the bilin-binding protein of Pieris brassicae, wherein said bilin-binding protein has at least 40% sequence homology with the bilin-binding protein of Pieris brassicae, and wherein the mutein binds a given target with detectable affinity.

In some embodiments the mutein of the invention does not bind the natural ligand such as bilin and biliverdin in case of the bilin-binding protein of Pieris brassicae.

In one embodiment, the lipocalin mutein further comprise at least one mutated amino acid residue at any of the sequence positions corresponding to the sequence positions 35, 36, 90, 93, 116, and 125 of the linear polypeptide sequence of the bilin-binding protein of Pieris brassicae.

In another embodiment the lipocalin mutein is derived from a polypeptide of a bilin-binding protein, comprising at least seven mutated amino acid residues at any of the sequence positions corresponding to the sequence positions 35, 36, 38, 39, 63, 64, 65, 67, 90, 91, 93, 116, 118, 120, 121, and 125 of the linear polypeptide sequence of the bilin-binding protein of *Pieris brassicae*. wherein said bilin-binding protein has at least 40% sequence homology with the bilin-binding protein of *Pieris brassicae*. Such a mutein also binds a given target with detectable affinity.

The invention is based on the surprising finding that lipocalin muteins with an improved binding affinity for a given protein epitope can be obtained by mutagenesis, in particular by random mutagenesis, of a maximum of only 16 amino acid residues within the four peptide loops encompassing the natural lipocalin binding pocket. The inventive muteins bind to their respective targets with nanomolar affinities. The respective dissociation constants were determined to be in a range up to 30-100 nM (cf. Examples).

The term "mutagenesis" as used herein means that the experimental conditions are chosen such that the amino acid naturally occurring at a given sequence position of a chosen bilin-binding protein can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of (the respective segment) of the wild-type protein. The term "random mutagenesis" refers to that no predetermined single amino acid (mutation) is present at a certain sequence position but that at least two amino acids can be incorporated into a selected sequence position during mutagenesis with a certain probability.

Such experimental conditions can, for example, be achieved by incorporating codons with a degenerate base composition into the sequence of the respective lipocalin employed. For example, use of the codon NNK or NNS (wherein N=adenine, guanine or cytosine or thymine; K=guanine or thymine; S=adenine or cytosine) allows incorporation of all 20 amino acids plus the amber stop codon during mutagenesis, whereas the codon VVS limits the number of possibly incorporated amino acids to 12, since it excludes the amino acids Cys, Ile, Leu, Met, Phe, Trp, Tyr, Val from being incorporated into the selected position of the polypeptide sequence; use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. In this respect it is noted that codons for other amino acids (than the regular 20 naturally occurring amino acids) such as selenocystein or pyrrolysine can also be incorporated into a nucleic acid of a mutein. It is also possible to use as described by Wang, L., et al., *Science,* 292:498-500, 2001 or Wang, L., Schultz, P. G., *Chem. Comm.,* 1:1-11, 2002 "artificial" codons such as UAG which are usually recognized as stop codons in order to introduce other unusual amino acids, for example O-methyl-L-tyrosine or p-aminophenylalanine.

The term "bilin-binding protein" as used herein is not limited to the bilin-binding protein of *Pieris brassicae* (SWISS-PROT Data Bank Accession Numbers P09464) but is meant to include all polypeptides having the structurally conserved lipocalin fold and a sequence homology with respect to the amino acid sequence of the bilin-binding protein of *Pieris brassicae* of at least 40%. The term lipocalin fold is used in its regular meaning as used, e.g., in Flower, D. R. (1996), supra, to describe the typical three-dimensional lipocalin structure with a conformationally conserved β-barrel as a central motif made of a cylindrically closed β-sheet of eight antiparallel strands, wherein the open end of the barrel the β-strands are connected by four loops in a pairwise manner so that the binding pocket is formed. The term "homology" as used herein in its usual meaning and includes identical amino acids as well as amino acids which are regarded to be conservative substitutions (for example, exchange of a glutamate residue by a aspartate residue) at equivalent positions in the linear amino acid sequence of two proteins that are compared with each other.

The percentage of homology is determined herein using the program BLASTP, version blastp 2.2.5 (Nov. 16, 2002; cf. Altschul, S. F. et al. (1997) *Nucleic Acids Res.* 25, 3389-3402). The percentage of homology is based on the alignment of the entire polypeptide sequences (cutoff value set to $10^{-3}$) including the propeptide sequences, using the bilin binding protein of *Pieris brassicae* as reference in a pairwise comparison. It is calculated as the percentage of numbers of "positives" (homologues amino acids) indicated as result in the BLASTP program output divided by the total number of amino acids selected by the program for the alignment. It is noted in this connection that this total number of selected amino acids can differ from the length of the bilin binding protein (189 amino acids including the propeptide) as it is seen in the following.

The term "bilin-binding protein" includes structural homologues, already identified or yet to be isolated, from other species which have an amino acid sequence homology of more than 40%. Examples of such proteins are insecticyanin A and B of the tobacco hawkmoth *Manducta sexta* (SWISS-PROT Data Bank Accession Numbers P00305 and Q00630, respectively) which have a sequence homology of 56.6% (98 positives/173 positions including the propeptide), and 57.2% (99 positives/173 positions including the propeptide), respectively, as determined with the program BLASTP as explained above. Such a structural homologue of the bilin-binding protein can be derived from any species, i.e. from prokaryotic as well as from eukaryotic organisms. In case of eukaryotic organisms, the structural homologue can be derived from invertebrates such as arthropods (e.g. butterflies, cockroaches, grasshoppers, lobster) as well as vertebrates such as mammals (e.g., human, monkey, cat or mouse).

In case a protein other than the bilin-binding protein of *Pieris brassicae* is used in the present invention, the definition of the mutated sequence positions given for the BBP of *Pieris brassicae* can be assigned to the other lipocalin with the help of published sequence alignments or alignments methods which are available to the skilled artisan. A sequence alignment can, for example, be carried out as explained in WO 99/16873 (cf. FIG. 3 therein), using the published alignment of Peitsch and Boguski (*New Biologist* (1990) 2, 197-206). If the three-dimensional structure of the lipocalin is available, as it is the case for insecticyanin, for instance, structural superpositions can also be used for the determination of those sequence positions that are to be subjected to mutagenesis in the present invention.

The structural homologue of the bilin binding protein can also be a mutein protein of the bilin-binding protein of *Pieris brassicae* itself in which amino acid substitutions are introduced at positions other than the positions in the four loops segments that are selected in the present invention. For example, such a mutein can be a protein in which positions at the solvent exposed surface of the β-barrel are mutated compared to the wild type sequence of the BBP of *Pieris brassicae* in order to increase the solubility or the stability of the protein.

In general, the term "bilin-binding protein” includes all proteins that have a sequence homology of more than 40%, 50%, 55%, 60%, 70% 80%, 85%, 90% or 95% in relation to the wild-type BBP of *Pieris brassicae.*

In one preferred embodiment of the invention the mutein as disclosed herein is derived from the bilin-binding protein of *Pieris brassicae*. In another preferred embodiment the mutein is derived from insecticyanin of *Manducta Sexta.*

Not all of the sequence positions corresponding to sequences positions 38, 39, 63, 64, 65, 67, 91, 118, 120, and 121 of the linear polypeptide sequence of the bilin-binding protein of *Pieris brassicae*, must be subjected to mutagenesis or mutate. In some embodiments, only 5 or 6 of these positions comprise a mutated amino acid residue compared to the respective wild type sequence.

In some embodiments the mutein of the invention comprises mutations at least any 7, 8, or at least any 10 to 12 of the sequence positions corresponding to amino acid positions 35, 36, 38, 39, 63, 64, 65, 67, 90, 91, 93, 116, 118, 120, 121, and 125 of the linear polypeptide sequence of the bilin-binding protein of *Pieris brassicae*. In other embodiments, the mutein comprises mutations at any 14 or any 15 of the selected sequence positions. It is also possible that a mutation occurs at all of the 16 sequence positions corresponding to amino acid positions 35, 36, 38, 39, 63, 64, 65, 67, 90, 91, 93, 116, 118, 120, 121, and 125 of the linear polypeptide sequence of the bilin-binding protein of *Pieris brassicae.*

In a preferred embodiment, at least one of the sequence positions defined above is subjected to complete randomization, i.e. all 20 natural amino acids as well as unusual amino acids such as selenocysteine, pyrrolysine, O-methyl-L-tyrosine or p-aminophenylalanine may potentially be present at this position after mutagenesis (cf. above).

By subjecting the lipocalin to mutagenesis for example, at the at least 5, 6 or 7 sequence positions as defined above, BBP muteins of the invention are obtained that can bind a given macromolecular target. Such target includes proteinaceous molecules, nucleic acids, and carbohydrates. In case of a proteinaceous target the lipocalin mutein of the invention can bind to a protein, a protein domain, and or a peptide. The protein can be any globular soluble protein or a receptor protein, for example, a trans-membrane protein involved in cell signaling, a component of the immune systems such as an MHC molecule or cell surface receptor that is indicative of a specific disease. The mutein may also be able to bind only fragments of a protein. For example, a mutein can bind to a domain of a cell surface receptor, when it is part of the receptor anchored in the cell membrane as well as to the same domain in solution, if this domain can be produced as a soluble protein as well. In this respect, it is also noted that the invention is by no means limited to muteins that only bind such macromolecular targets. But it is also possible to obtain muteins of BBP by means of mutagenesis which show specific binding affinity to ligands of low(er) molecular weight. Such a ligand can be a chemical compound in free or conjugated form, which exhibits features of an immunological hapten.

In some embodiments BBP muteins of the invention are preferred that bind to a target selected from the group consisting of CD47, ferritin, CD154, CD4, a fragment or a homologue thereof, wherein the fragment or the homologue has at least 80% sequence homology.

In some embodiments BBP muteins as disclosed herein that bind:

(a) CD47, wherein the nucleic acid molecule is selected from the group consisting of SEQ ID NO: 16, SEQ ID NO: 17, and SEQ ID NO: 18, (b) ferritin, wherein the nucleic acid molecule is selected from the group consisting of SEQ ID NO: 19, SEQ ID NO: 20, SEQ ID NO: 21, SEQ ID NO: 22, SEQ ID NO: 23, and SEQ ID NO: 24, (c) CD154, wherein the nucleic acid molecule is selected from the group consisting of SEQ ID NO: 28, SEQ ID NO: 29, SEQ ID NO: 30, SEQ ID NO: 31, and SEQ ID NO: 32, and (d) CD4, wherein the nucleic acid molecule is selected from the group consisting of SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

The lipocalin muteins of the invention may comprise the wild-type (natural) amino acid sequence at any non-mutated position, for example outside the mutated segments. On the other hand, the BBP muteins disclosed herein may also contain amino acid mutations apart from those sequence positions that are subjected to mutagenesis. Such mutations are often tolerated or can even prove to be advantageous, for example if they contribute to an improved folding efficiency, protein stability or ligand binding affinity of the mutein. Such mutations can be accomplished very easily on DNA level using established standard methods (cf., for example, Sambrook, J. et al. (1989) *Molecular Cloning: A Laboratory Manual,* 2nd Ed., Cold Spring Harbor Laboratory Press, Cold Spring Harbor, N.Y.). Possible alterations of the amino acid sequence are insertions or deletions as well as amino acid substitutions. Such substitutions may be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. One the other hand, it is also possible to introduce non-conservative alterations in the amino acid sequence.

Such modifications of the amino acid sequence include directed mutagenesis of single amino acid positions in order to simplify sub-cloning of the mutein gene or its parts by incorporating cleavage sites for certain restriction enzymes. Furthermore, mutations can specifically be introduced in order to improve certain characteristics of the mutein.

The BBP muteins of the invention are able to bind the desired target with detectable affinity, i.e. with an affinity constant of preferably at least $10^5$ $M^{-1}$, $10^6$ $M^{-1}$ or $10^7$ $M^{-1}$. Affinities lower than $10^5$ $M^{-1}$ are generally no longer measurable with common methods such as ELISA and therefore of secondary importance. Preferred are lipocalin muteins, which bind the desired target with an affinity of at least $10^6$ $M^{-1}$, corresponding to a dissociation constant of the complex of 1 μM. The binding affinity of a mutein to the desired target can be measured by a multitude of methods such as fluorescence titration, competition ELISA or surface plasmon resonance.

It is clear to the skilled person that complex formation is dependent on many factors such as concentration of the binding partners, the presence of competitors, ionic strength of the buffer system etc. Selection and enrichment is generally performed under conditions allowing the isolation of lipocalin muteins having an affinity constant of at least $10^5$ $M^{-1}$ to the target. However, the washing and elution steps can be carried out under varying stringency. A selection with respect to the kinetic characteristics is possible as well. For example, the selection can be performed under conditions, which favor complex formation of the target with muteins that show a slow dissociation from the target, or in other words a low $k_{off}$ rate.

A BBP mutein of the invention may be used for complex formation with a given target. The target (ligand) may be any macromolecule in free or conjugated form and may be selected from the group consisting of proteinaceous molecules, nucleic acids, and polysaccharides, with proteinaceous targets being preferred. As explained above, proteinaceous targets may be selected from the group consisting of proteins, protein domains, and peptides. Particularly suitable target molecules are proteins located at the cellular surface such as CD4, CD47 or CD154.

For some applications, it is useful to employ the inventive muteins in a labeled form. Accordingly, the invention is also directed to muteins which are conjugated to a label selected from the group consisting of enzyme labels, radioactive labels, colored label, fluorescent labels, chromogenic labels, luminescent labels, haptens, digoxigenin, biotin, metal complexes, metals, and colloidal gold. The mutein may also be conjugated to an organic molecule. The term "organic molecule" as used herein preferably denotes an organic molecule comprising at least two carbon atoms, but preferably not more than seven rotatable carbon bonds, having a molecular weight in the range between 100 and 2000 Dalton, preferably 1000 Dalton, and optionally including one or two metal atoms.

In general, it is possible to label the lipocalin mutein with any appropriate chemical substance or enzyme, which directly or indirectly generates a detectable compound or signal in a chemical, physical or enzymatic reaction. An example for a physical reaction is the emission of fluorescence upon irradiation or the emission of X-rays when using a radioactive label. Alkaline phosphatase, horseradish peroxidase, and β-galactosidase are examples of enzyme labels, which catalyze the formation of chromogenic reaction products. In general, all labels commonly used for antibodies (except those exclusively used with the sugar moiety in the Fc-part of immunoglobulins) can also be used for conjugation to the muteins of the present invention. Such conjugates can be produced by methods well known in the art.

For several applications of the muteins disclosed herein it may be advantageous to use them in the form of fusion proteins. In preferred embodiments the inventive mutein is fused at its N-terminus or its C-terminus to a protein, a protein domain or a peptide such as a signal sequence and/or an affinity tag.

The fusion partner may confer new characteristics to the inventive mutein such as enzymatic activity or binding affinity for other molecules. Examples of suitable fusion proteins are alkaline phosphatase, horseradish peroxidase, gluthation-5-transferase, the albumin-binding domain of protein G, protein A, antibody fragments, oligomerization domains, lipocalin muteins of same or different binding specificity (which results in the formation of "duocalins", cf. Schlehuber, S. & Skerra, A. (2001), *Biol. Chem.* 382, 1335-1342), or toxins. Affinity tags such as the STREP-TAG® or STREP-TAG® II (strepavidin tag used for detection or purification of recombinant proteins) (Schmidt, T. G. M. et al. (1996) *J. Mol. Biol.* 255, 753-766), the myc-tag, the FLAG-tag, the His$_6$-tag (SEQ ID NO: 73) or the HA-tag or proteins such as glutathione-S-transferase allow easy detection and/or purification of recombinant proteins are further examples of preferred fusion partners. Finally, proteins with chromogenic or fluorescent properties such as the green fluorescent protein (GFP) or the yellow fluorescent protein (YFP) are suitable as well.

The term "fusion protein" as used herein also comprises lipocalin muteins according to the invention that contain a signal sequence. Signal sequences at the N-terminus of a polypeptide direct this polypeptide to a specific cellular compartment, for example the periplasm of *E. coli* or the endoplasmatic reticulum of eukaryotic cells. A large number of signal sequences is known in the art. A preferred signal sequence for secretion a polypeptide into the periplasm of *E. coli* is the OmpA-signal sequence.

The present invention also relates to nucleic acid molecules (DNA and RNA) comprising nucleotide sequences encoding a BBP mutein or a conjugate or a fusion protein thereof as described herein. Since the degeneracy of the genetic code permits substitutions of certain codons by other codons specifying the same amino acid, the invention is not limited to a specific nucleic acid molecule encoding a mutein of the invention but includes all nucleic acid molecules comprising nucleotide sequences encoding a functional BBP mutein.

In a preferred embodiment of the invention the sequence of the nucleic acid molecule is derived from the bilin-binding protein of *Pieris brassicae*. In another preferred embodiment the nucleic acid molecule is derived from insecticyanin of *Manducta Sexta*.

In another preferred embodiment the nucleic acid sequence encoding a mutein according to the invention comprises mutations in at least any 7, 8, or at least any 10 to 12, and most preferably at all 16 sequence positions that correspond to amino acid positions 35, 36, 38, 39, 63, 64, 65, 67, 90, 91, 93, 116, 118, 120, 121, and 125 of the linear polypeptide sequence of the bilin-binding protein of *Pieris brassicae*.

The invention as disclosed herein also includes nucleic acid molecules encoding BBP muteins, which comprise additional mutations outside the segments of experimental mutagenesis. Such mutations are often tolerated or can even prove to be advantageous, for example if they contribute to an improved folding efficiency, protein stability or ligand binding affinity of the mutein.

In a one preferred embodiment the nucleic acid molecule encodes an inventive BBP mutein that binds a macromolecular target selected from the group consisting of proteinaceous molecules, nucleic acids, and carbohydrates. Most suitable are nucleic acid molecules encoding a mutein that binds a proteinaceous target selected from the group consisting of proteins, protein domains, and peptides. Examples of such nucleic acid molecules are those molecules encoding an inventive mutein binding to a target selected from the group consisting of CD47, ferritin, CD154, CD4 or fragment or a homologue thereof comprising at least 80% sequence homology.

Examples of respective nucleic acid molecules encoding such a mutein are those that bind to:
  (a) CD47, wherein the nucleic acid molecule is selected from the group consisting of SEQ ID NO: 16, SEQ ID NO: 17, and SEQ ID NO: 18,
  (b) ferritin, wherein the nucleic acid molecule is selected from the group consisting of SEQ ID NO: 19, SEQ ID NO: 20, SEQ ID NO: 21, SEQ ID NO: 22, SEQ ID NO: 23, and SEQ ID NO: 24,
  (c) CD154, wherein the nucleic acid molecule is selected from the group consisting of SEQ ID NO: 28, SEQ ID NO: 29, SEQ ID NO: 30, SEQ ID NO: 31, and SEQ ID NO: 32, and
  (d) CD4, wherein the nucleic acid molecule is selected from the group consisting of SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it comprises sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3'-non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the invention can include a regulatory sequence, preferably a promoter sequence. In another preferred embodiment, a nucleic acid molecule of the invention comprises a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the invention can also be comprised in a vector or any other cloning vehicles, such as plasmids, phagemids, phage, baculovirus, cosmids or artificial chromosomes. In a preferred embodiment, the nucleic acid molecule is comprised in a phagemid. A phagemid vector denotes a vector encoding the intergenic region of a temperent phage, such as M13 or fI, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (reviewed, e.g., in Kay, B. K. et al. (1996) *Phage Display of Peptides and Proteins—A Laboratory Manual*, 1st Ed., Academic Press, New York N.Y.; Lowman, H. B. (1997) *Annu. Rev. Biophys. Biomol. Struct.* 26, 401-424; or Rodi, D. J., and Makowski, L. (1999) *Curr. Opin. Biotechnol.* 10, 87-93).

Such cloning vehicles can include, aside from the regulatory sequences described above and a nucleic acid sequence encoding a mutein of the invention, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding lipocalin muteins of the invention, and in particular a cloning vector containing the coding sequence of such a lipocalin mutein can be transformed into a host cell capable of expressing the gene. Transformation can be performed using standard techniques (Sambrook, J. et al. (1989), supra). Thus, the invention is also directed to a host cell containing a nucleic acid molecule as disclosed herein.

The transformed host cells are cultured under conditions suitable for expression of the nucleotide sequence encoding a fusion protein of the invention. Suitable host cells can be prokaryotic, such as *Escherichia coli* (*E. coli*) or *Bacillus subtilis*, or eukaryotic, such as *Saccharomyces cerevisiae*, *Pichia pastoris*, SF9 or High5 insect cells, immortalized mammalian cell lines (e.g. HeLa cells or CHO cells) or primary mammalian cells.

The invention also relates to a method for the generation of a mutein of any of claims 1 to 20, comprising:

(a) subjecting a nucleic acid molecule encoding a bilin-binding protein to mutagenesis at a nucleotide triplet coding for at least one of any of the sequence positions corresponding to the sequence positions 38, 39, 63, 64, 65, 67, 91, 116, 118, 120, and 121 of the linear polypeptide sequence of the bilin-binding protein of *Pieris brassicae*, resulting in one or more mutein nucleic acid molecule(s)

(b) expressing the one more mutein nucleic acid molecule(s) obtained in (a) in a suitable expression system, and (c) enriching the one or more mutein(s) having a detectable binding affinity for a given target by means of selection and/or isolation.

In this method the nucleic acid molecule may be subjected to mutagenesis at at least 5 or 6 nucleotide triplet coding for any of said sequence positions.

It is also possible to subject the nucleic acid molecule to mutagenesis at at least one nucleotide triplet coding for any of the sequence positions corresponding to the sequence positions 35, 36, 90, 93, 116, and 125 of the linear polypeptide sequence of the bilin-binding protein of *Pieris brassicae*.

In a further embodiment the method for the generation of a mutein comprises subjecting a nucleic acid molecule encoding a bilin-binding protein to mutagenesis at nucleotide triplets coding for at least any 7 of the sequence positions corresponding to the sequence positions 35, 36, 38, 39, 63, 64, 65, 67, 90, 91, 93, 116, 118, 120, 121, and 125 of the linear polypeptide sequence of the bilin-binding protein of *Pieris brassicae*.

In further embodiments of the method, the nucleic acid molecule can be subjected to mutagenesis at any 8 to 12 or at any of 14 or 15 of the selected sequence positions. In one preferred embodiment a nucleic acid molecule encoding a bilin binding protein is (intentionally) subjected to mutagenesis (only) at all of the 16 chosen sequence positions within the four peptide loops of the lipocalin binding site.

In the method of generation a mutein or a fusion protein thereof is obtained starting from the nucleic acid encoding a polypeptide of a bilin-binding protein, which is subjected to mutagenesis and introduced into a suitable bacterial or eukaryotic host organism by means of recombinant DNA technology (as already outlined above).

The coding sequence of, e.g., the bilin-binding protein of *Pieris brassicae* (Schmidt, F. S., and Skerra, A. (1994), supra), can serve as a starting material for mutagenesis of the peptide segments selected in the present invention. For the mutagenesis of the amino acids in the four peptide loops encompassing the natural lipocalin binding pocket, the person skilled in the art has at his disposal the various established standard methods for site-directed mutagenesis (Sambrook, J. et al., (1989), supra). A commonly used technique is the introduction of mutations by means of PCR (polymerase chain reaction) using mixtures of synthetic oligonucleotides, which bear a degenerate base composition at the desired sequence positions. The use of nucleotide building blocks with reduced base pair specificity, as for example inosine, is another option for the introduction of mutations into a chosen sequence segment. A further possibility is the so-called triplet-mutagenesis. This method uses mixtures of different nucleotide triplets each of which codes for one amino acid for the incorporation into the coding sequence.

One possible strategy for introducing mutations in the selected regions of the BBP is based on the use of four oligonucleotides, each of which is partially derived from one of the corresponding sequence segments to be mutated (cf. FIG. 3). When synthesizing these oligonucleotides, a person skilled in the art can employ mixtures of nucleic acid building blocks for the synthesis of those nucleotide triplets which correspond to the amino acid positions to be mutated so that codons encoding all natural amino acids randomly arise, which at last results in the generation of a peptide library. For example, the first oligonucleotide corresponds in its sequence—apart from the mutated positions—to the coding strand for the peptide segment to be mutated at the most N-terminal position of the lipocalin polypeptide. Accordingly, the second oligonucleotide corresponds to the non-coding strand for the second sequence segment following in the polypeptide sequence. The third oligonucleotide corresponds in turn to the coding strand for the corresponding third sequence segment. Finally, the fourth oligonucleotide corresponds to the non-coding strand for the fourth sequence segment. A polymerase chain reaction can be performed with the respective first and second oligonucleotide and separately, if necessary, with the respective third and fourth oligonucleotide.

The amplification products of both of these reactions can be combined by various known methods into a single nucleic acid comprising the sequence from the first to the fourth sequence segments, in which mutations have been introduced at the selected positions. To this end, both of the products can for example be subjected to a new polymerase chain reaction using flanking oligonucleotides as well as one or more mediator nucleic acid molecules, which contribute the sequence between the second and the third sequence segment. This procedure is schematically reproduced in FIG. 3. Regarding the choice of number and arrangement of the oligonucleotides used for the mutagenesis, the person skilled in the art has numerous alternatives at his disposal.

The nucleic acid molecules defined above can be connected by ligation with the missing 5'- and 3'-sequences of a nucleic acid encoding a lipocalin polypeptide and/or the vector, and can be cloned in a known host organism. A multitude of established procedures are available for ligation and cloning (Sambrook, J. et al. (1989), supra). For example, recognition sequences for restriction endonucleases also present in the sequence of the cloning vector can be engineered into the sequence of the synthetic oligonucleotides. Thus, after amplification of the respective PCR product and enzymatic cleavage the resulting fragment can be easily cloned using the corresponding recognition sequences.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains. Such methods can also be used for further optimization of the target affinity or specificity of a mutein. Mutations possibly occurring outside the segments of experimental mutagenesis are often tolerated or can even prove to be advantageous, for example if they contribute to an improved folding efficiency or folding stability of the mutein.

After expression of the nucleic acid sequences that were subjected to mutagenesis in an appropriate host, the clones carrying the genetic information for the plurality of the respective muteins, which bind a given target can be selected from the library obtained. Well known techniques can be employed for the selection of these clones, such as phage display (reviewed in Kay, B. K. et al. (1996), supra; Lowman, H. B. (1997), supra; or Rodi, D. J., and Makowski, L. (1999), supra), colony screening (reviewed in Pini, A. et al. (2002) Comb. Chem. High Throughput Screen. 5, 503-510), ribosome display (reviewed in Amstutz, P. et al. (2001) Curr. Opin. Biotechnol. 12, 400-405) or mRNA display (reviewed in Wilson, D. S. et al. (2001) Proc. Natl. Acad. Sci. USA 98, 3750-3755).

An embodiment of the phage display technique (reviewed in Kay, B. K. et al. (1996), supra; Lowman, H. B. (1997), supra; or Rodi, D. J., and Makowski, L. (1999), supra) using temperent M13 phage is given as an example of a selection method according to the invention. However, it is noted that other temperent phage such as f1 or lytic phage such as T7 may be employed as well. For the exemplary selection method, M13 phagemids (cf. also above) are produced which allow the expression of the mutated lipocalin nucleic acid sequence as a fusion protein with a signal sequence at the N-terminus, preferably the OmpA-signal sequence, and with the capsid protein pIII of the phage M13 or fragments thereof capable of being incorporated into the phage capsid at the C-terminus. The C-terminal fragment ΔpIII of the phage capsid protein comprising amino acids 217 to 406 of the wild-type sequence is preferably used to produce the fusion proteins. Especially preferred is a C-terminal fragment of pIII, in which the cysteine residue at position 201 is missing or is replaced by another amino acid.

The fusion protein may comprise additional components such as an affinity tag, which allows the immobilization and/or purification of the fusion protein or its parts. Furthermore, a stop codon can be located between the sequence regions encoding the lipocalin or its muteins and the phage capsid gene or fragments thereof, wherein the stop codon, preferably an amber stop codon, is at least partially translated into an amino acid during translation in a suitable suppressor strain.

For example, the vectors pBBP20 (FIG. 1) or pBBP38 (FIG. 2) can be used for the construction of a phage library encoding BBP muteins according to the invention. The nucleic acid molecules coding for the mutated peptide segments are inserted into the vector using the BstXI restriction sites. Recombinant vectors are then transformed into a suitable host strain such as E. coli XL1-Blue. The resulting library is subsequently superinfected in liquid culture with an appropriate M13-helper phage in order to produce functional phage. The recombinant phagemid displays the mutein on its surface as a fusion with the coat protein pIII or a fragment thereof, while the N-terminal signal sequence of the fusion protein is normally cleaved off. On the other hand, it also bears one or more copies of the native capsid protein pIII supplied by the helper phage and is thus capable of infecting a recipient, in general a bacterial strain carrying a F- or F'-plasmid. During or after infection gene expression of the fusion protein comprised of the BBP mutein and the capsid protein pIII can be induced, for example by addition of anhydrotetracycline. The induction conditions are chosen such that a substantial fraction of the phage displays at least one lipocalin mutein on their surface. Various methods are known for isolating the phage, such as precipitation with polyethylene glycol. Isolation typically occurs after an incubation period of 6-8 hours.

The isolated phagemids are then subjected to a selection process by incubating them with a given target, wherein the target is present in a form allowing at least a temporary immobilization of those phage displaying muteins with the desired binding activity. Several immobilization methods are known in the art. For example, the target can be conjugated with a carrier protein such as serum albumin and be bound via this carrier to a protein-binding surface such as polystyrene. Microtiter plates suitable for ELISA techniques or so-called "immunosticks" are preferred. Alternatively, conjugates of the target can also be implemented with other binding groups such as biotin. The target can then be immobilized on surfaces, which will selectively bind this group, such as microtiter plates or paramagnetic particles coated with avidin or streptavidin.

For example, the phage particles are captured by binding to the respective immobilized target. Unbound phage particles are subsequently removed by iterative washing. For the elution of bound phage, free target (ligand) molecules can be added to the samples as a competitor. Alternatively, elution can also be achieved by adding proteases or under moderately denaturing conditions, e.g. in the presence of acids, bases, detergents or chaotropic salts. A preferred method is the elution using buffers having pH 2.2, followed by neutralization of the solution. The eluted phage may then be subjected to another selection cycle. Preferably, selection is continued until at least 0.1% of the clones comprise lipocalin muteins with detectable affinity for the respective target. Depending on the complexity of the library employed 2-8 cycles are required to this end.

For the functional analysis of the selected muteins, an *E. coli* host strain is infected with the phage obtained and phage DNA is isolated using standard techniques (Sambrook, J. et al. (1989), supra). The mutated sequence fragment or the entire mutein nucleic acid sequence can be sub-cloned in any suitable expression vector such as pBBP46 (FIG. 5) or pBBP47 (FIG. 7). The recombinant muteins obtained can be purified from their host organism or from a cell lysate by various methods known in the art such as gel filtration or affinity chromatography.

However, the selection of muteins can also be performed using other methods well known in the art. Furthermore, it is possible to combine different procedures. For example, clones selected or at least enriched by phage display can subsequently be subjected to a colony-screening assay in order to directly isolate a particular lipocalin mutein with detectable binding affinity for a given target. Additionally, instead of generating a single phage library comparable methods can be applied in order to optimize a mutein with respect to its affinity or specificity for the desired target by repeated, optionally limited mutagenesis of its coding nucleic acid sequence.

The invention also relates to a method for the production of a mutein of the invention, wherein the mutein, a fragment of the mutein or a fusion protein of the mutein and another polypeptide is produced starting from the nucleic acid coding for the mutein by means of genetic engineering methods. The method can be carried out in vivo, the mutein can for example be produced in a bacterial or eucaryotic host organism and then isolated from this host organism or its culture. It is also possible to produce a protein in vitro, for example by use of an in vitro translation system.

When producing the mutein in vivo a nucleic acid encoding a mutein of the invention is introduced into a suitable bacterial or eukaryotic host organism by means of recombinant DNA technology (as already outlined above). For this purpose, the host cell is first transformed with a cloning vector comprising a nucleic acid molecule encoding a mutein of the invention using established standard methods (Sambrook, J. et al. (1989), supra). The host cell is then cultured under conditions, which allow expression of the heterologous DNA and thus the synthesis of the corresponding polypeptide. Subsequently, the polypeptide is recovered either from the cell or from the cultivation medium. Since many lipocalins such as the bilin binding protein or the insecticyanin comprise intramolecular disulfide bonds, it can be preferred to direct the polypeptide to a cell compartment having an oxidizing redox-milieu using an appropriate signal sequence. Such an oxidizing environment is provided in the periplasm of Gram-negative bacteria such as *E. coli* or in the lumen of the endoplasmatic reticulum of eukaryotic cells and usually favours the correct formation of the disulfide bonds. It is, however, also possible to generate a mutein of the invention in the cytosol of a host cell, preferably *E. coli*. In this case, the polypeptide can, for instance, be produced in form of inclusion bodies, followed by renaturation in vitro. A further option is the use of specific host strains having an oxidizing intracellular milieu, which thus allow the production of the native protein in the cytosol.

However, a mutein of the invention may not necessarily be generated or produced only by use of genetic engineering. Rather, a lipocalin mutein can also be obtained by chemical synthesis such as Merrifield solid phase polypeptide synthesis. It is for example possible that promising mutations are identified using molecular modeling and then to synthesize the wanted (designed) polypeptide in vitro and investigate the binding activity for a given target.

The invention also relates to a pharmaceutical composition comprising at least one inventive mutein or a fusion protein thereof. The composition can also comprise a pharmaceutically acceptable excipient.

The muteins according to the invention can be administered via any parenteral or non-parenteral (enteral) route that is therapeutically effective for proteinaceous drugs. Parenteral application methods comprise, for example, intracutaneous, subcutaneous, intramuscular or intravenous injection and infusion techniques, e.g. in the form of injection solutions, infusion solutions or tinctures, as well as aerosol installation and inhalation, e.g. in the form of aerosol mixtures, sprays or powders. Non-parenteral delivery modes are, for instance, orally, e.g. in the form of pills, tablets, capsules, solutions or suspensions, or rectally, e.g. in the form of suppositories. The muteins of the invention can be administered systemically or topically in formulations containing conventional non-toxic pharmaceutically acceptable excipients or carriers, additives and vehicles as desired.

In a preferred embodiment of the present invention the pharmaceutical composition is administered parenterally to a mammal, and in particular to humans, with aerosol installation being the most preferable application method due to the low molecular weight of the muteins.

Accordingly, the muteins of the present invention can be formulated into compositions using pharmaceutically acceptable ingredients as well as established methods of preparation (cf., e.g., Gennaro, A. L. and Gennaro, A. R. (2000) *Remington: The Science and Practice of Pharmacy*, 20th Ed., Lippincott Williams & Wilkins, Philadelphia, Pa.). To prepare the pharmaceutical compositions, pharmaceutically inert inorganic or organic excipients can be used. To prepare, e.g., pills, powders, gelatin capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes and microcapsules.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

As is evident from the above disclosure, a mutein of the present invention or a fusion protein or a conjugate thereof can be employed in many applications. In general, such a mutein can be used in all applications antibodies are used, except those with specifically rely on the glycosylation of the Fc part.

A mutein of the invention can also be used for the targeting of a compound to a preselected site. For such a purpose the mutein is contacted with the compound of interest in order to allow complex formation. Then the complex comprising the mutein and the compound of interest are delivered the preselected site. This use is in particular suitable, but not restricted to, for delivering a drug (selectively) to the site such an infected body part or organ which is supposed to be treated with the drug.

Another use of the inventive muteins is the binding/detection of a given target or target molecule, comprising contacting the mutein with a test sample supposed to contain said target, and detecting of the mutein/target complex by a suitable signal. A mutein can also be used for the separation of a given target, comprising contacting the mutein with a sample supposed to contain said target in order to allow contact formation, and separating the mutein/target complex from the sample. In such uses the complex comprising the mutein and the target may be immobilized on any suitable solid phase.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The muteins disclosed herein and its derivatives can thus be used in many fields similar to antibodies or fragments thereof. In addition to their use for binding to a support, allowing the target of a given mutein or a conjugate or a fusion protein of this target to be immobilized or separated, the muteins can be used for labeling with an enzyme, an antibody, a radioactive substance or any other group having biochemical activity or defined binding characteristics. By so doing, their respective targets or conjugates or fusion proteins thereof can be detected or brought in contact with them. For example, muteins of the invention can serve to detect chemical structures by means of established analytical methods (e.g. ELISA or Western Blot) or by microscopy or immunosensorics.

Here, the detection signal can either be generated directly by use of a suitable mutein conjugate or fusion protein or indirectly by immunochemical detection of the bound mutein via an antibody.

Numerous possible applications for the inventive muteins also exist in medicine. In addition to their use in diagnostics and drug delivery, a mutant polypeptide of the invention, which binds, for example, tissue- or tumor-specific cellular surface molecules can be generated. Such a mutein may, for example, be employed in conjugated form or as a fusion protein for "tumor imaging" or directly for cancer therapy.

Another related and preferred use of a mutein described herein is target validation, i.e. the analysis whether a polypeptide assumed to be involved in the development or progress of a disease or disorder is indeed somehow causative of that disease or disorder. This use for validating a protein as a pharmacological drug target takes advantage of the ability of a mutein of the present invention to specifically recognize a surface area of a protein in its native conformation, i.e. to bind to a native epitope. In this respect, it is to be noted that this ability has been reported only for a limited number of recombinant antibodies. However, the use of an inventive mutein for validation of a drug target is not limited to the detection of proteins as targets, but also includes the detection of protein domains, peptides, nucleic acid molecules, organic molecules or metal complexes.

BRIEF DESCRIPTION OF THE DRAWINGS

The invention is further illustrated by the following non-limiting examples and the attached drawings in which:

FIG. 1 shows a schematic drawing of pBBP20. This vector codes for a fusion protein of the OmpA signal sequence (ompA), a modified BBP with the four amino acid substitutions Asn1 to Asp, Asn21 to Gln, Lys135 to Met as well as Lys87 to Ser, STREP-TAG® II affinity tag (strepII) and a shortened form of the M13 coat protein pIII, comprising amino acids 217 to 406 (pIII). The entire structural gene is subject to the transcriptional control of the tetracycline promoter/operator (tet$^{p/o}$) and ends at the lipoprotein transcription terminator (t$_{lpp}$). Further elements of the vector are the origin of replication (ori), the intergenic region of the filamentous bacteriophage f1 (f1-IG), the ampicillin resistance gene coding for β-lactamase (bla) and the tetracycline repressor gene (tetR). An amber stop codon, which is partially translated into Gln in a supE amber suppressor host strain, is located between the coding region for BBP, which is equipped with the OmpA signal sequence and the STREP-TAG® II, and the coding region for the truncated phage coat protein pIII. The two BstXI-restriction sites used for the cloning of the mutated gene cassette and the HindIII restriction site at the end of the structural gene is labelled. The nucleic acid sequence of pBBP20 is shown in the European patent publication EP1017814.

FIG. 2 shows a schematic drawing of pBBP38. This vector codes for a fusion protein of the OmpA signal sequence, a modified BBP with interrupted reading frame due to an ochre stop codon and an opal stop codon at the positions of Cys42 and Gly 43, respectively, and a shortened form of the M13 coat protein pIII, comprising amino acids 217 to 406. The two stop codons Cys42 to ochre and Gly43 to opal were introduced to prevent phagemid display of wildtype BBP, possibly caused by the religation of incompletely digested phasmid vector during the preparation of the library of BBP muteins. The XbaI and HindIII restriction sites flanking the whole structural gene are labelled. All further depicted elements of the vector are identical with pBBP20. A relevant segment from the nucleic acid sequence of pBBP38 is reproduced together with the encoded amino acid sequence in the sequence listing as SEQ ID NOS: 1 (nucleic acid sequence) and SEQ ID NO: 41 (amino acid sequence). The segment begins with the XbaI restriction site and ends with the HindIII restriction site. The vector elements outside this region are identical with those of the vector pASK75, the complete nucleotide sequence of which is exhibited in the German patent publication DE 44 17 598 A1.

FIG. 3 shows the strategy for the concerted mutagenesis of 16 selected amino acid positions in the BBP by repeated application of the polymerase chain reaction (PCR). For each of the four peptide loops in which the amino acids are to be mutated, an oligodeoxynucleotide was synthesized, (SEQ ID NO: 2, SEQ ID NO: 3, SEQ ID NO: 4 and SEQ ID NO: 5), carrying random nucleotides as given in the sequence listing. Due to the composition chosen, from the altogether three possible stop codons only the amber stop codon, TAG, was allowed at the mutated codons, which is partially translated to Gln in the *E. coli* supE strains XL1-blue (Bullock et al., BioTechniques 5 (1987), 376-378) or TG1 (Sambrook et al., Molecular Cloning. A Laboratory Manual (1989), Cold Spring Harbor Press) that were used for gene expression. For certain applications, for example for gene expression in other bacterial strains or organisms, such a nonsense codon, when it arises in the structural gene for a selected BBP mutein, can be substituted by a Gln codon by the person skilled in the art, for example via site-directed mutagenesis. A nucleic acid fragment with 159 base pairs was amplified (PCR No. 1, A) with the primers SEQ ID NO: 2 and SEQ ID NO: 3 using the pBBP20 plasmid DNA containing the cloned BBP cDNA as template. In another PCR, a nucleic acid fragment with 164 base pairs was amplified (PCR No. 1, B) with the primers SEQ ID NO: 4 and SEQ ID NO: 5, also using pBBP20 as template. The mixture of both PCR products served as template in another amplification (PCR No. 2) together with the mediating primer SEQ ID NO: 6, two 5'-biotinylated flanking PCR primers SEQ ID NO: 7 and SEQ ID NO: 8, such that an assembled gene fragment of 371 base pairs was obtained. This fragment contained the mixture of all 16 mutated codons and was subsequently cloned on the vector pBBP38 using the two BstXI restriction sites. The special arrangement of these two restriction sites, which led to two non-compatible overhanging DNA ends during the restriction digest, enabled a particularly efficient ligation. The ligation efficiency could be improved by purification of the digested PCR fragment via paramagnetic streptavidin-coated beads from undigested or partially digested material. In order to introduce both BstXI restriction sites into the BBP structural gene and to eliminate a protease cleavage site the substitution of the amino acids Asn21 to Gln, Lys135 to Met as well as Lys87 to Ser, respectively, were previously accomplished during the construction of pBBP20 with respect to the original sequence.

FIG. 4 shows a schematic drawing of the expression vector pASK75-strepII-CD47. pASK75-strepII-CD47 codes for a fusion protein made of the OmpA signal sequence, a modified extracellular domain of human CD47 comprising amino acids 1 to 119 of the mature protein with the amino acid substitution Cys 15 to Ala and the STREP-TAG® II affinity tag. All further genetic elements are identical with the generic vector pASK75. A relevant segment from the nucleic acid sequence of pASK75-strepII-CD47 is reproduced together with the encoded amino acid sequence in the sequence listing as SEQ ID NOS: 9 (nucleotide sequence) and SEQ ID NO: 42 (amino acid sequence). The segment begins with the XbaI restriction site and ends with the HindIII restriction site. The vector elements outside this region are identical with the vector pASK75, the complete nucleotide sequence of which is exhibited in the German patent publication DE 44 17 598 A1.

FIG. 5 shows a schematic drawing of the expression vector pBBP46. pBBP46 codes for a fusion protein of the OmpA signal sequence and the T7 detection tag (T7) with a modified BBP according to FIG. 1, including the C-terminal STREP-TAG® II. This structural gene is followed by the dsbC structural gene (including its ribosomal binding site) from *E. coli* (Zapun et al., Biochemistry 34 (1995), 5075-5089) as a second cistron (dsbC). A relevant segment of the nucleic acid sequence of pBBP46 is reproduced together with the encoded amino acid sequence in the sequence listing as SEQ ID NO: 10. The segment begins with the XbaI restriction site and ends with the HindIII restriction site. The vector elements outside this region are identical with the vector pASK75, the complete nucleotide sequence of which is exhibited in the German patent publication DE 44 17 598 A1.

FIG. 5 shows a schematic drawing of the expression vector pBBP46. pBBP46 codes for a fusion protein of the OmpA signal sequence and the T7 detection tag (T7) with a modified BBP according to FIG. 1, including the C-terminal Strep-tag® II. This structural gene is followed by the dsbC structural gene (including its ribosomal binding site) from *E. coli* (Zapun et al., Biochemistry 34 (1995), 5075-5089) as a second cistron (dsbC). A relevant segment of the nucleic acid sequence of pBBP46 is reproduced together with the encoded amino acid sequence in the sequence listing as SEQ ID NOS: 10 (nucleotide sequence) and SEQ ID NO: 43 (amino acid sequence). The segment begins with the XbaI restriction site and ends with the HindIII restriction site. The vector elements outside this region are identical with the vector pASK75, the complete nucleotide sequence of which is exhibited in the German patent publication DE 44 17 598 A1.

FIG. 6 shows a graphical representation of the data from Example 8, in which binding measurements with BBP muteins and the intended target CD47 as well as the unrelated target BSA were performed by Enzyme-Linked Immunosorbent Assay (ELISA). Binding of BBP muteins CD47-F11 (circles), CD47-F2 (squares), CD47-A9 (triangles) and CD47-G6 (diamonds) to CD47, which was immobilized on the ELISA plate, was compared with the interaction of the muteins with immobilized BSA (open symbols) as a control. The BBP muteins bind CD47 in a concentration-dependent manner, whereas only weak binding signals to BSA were detectable.

FIG. 7 shows a schematic drawing of the expression vector pBBP47. pBBP47 codes for a fusion protein of the OmpA signal sequence with a modified BBP according to FIG. 1, followed by a T7 detection tag and the C-terminal STREP-TAG® II, in turn followed by the dsbC structural gene as separate cistron. A relevant segment of the nucleic acid sequence of pBBP47 is reproduced together with the encoded amino acid sequence in the sequence listing as SEQ ID NOS: 11 (nucleotide sequence) and SEQ ID NO: 44 (amino acid sequence). The segment begins with the XbaI restriction site and ends with the HindIII restriction site. The vector elements outside this region are identical with the vector pASK75, the complete nucleotide sequence of which is exhibited in the German patent publication DE 44 17 598 A1.

FIG. 8 shows a graphical representation of the data from Example 12, in which binding measurements with BBP muteins and the prescribed target ferritin as well as the unrelated targets transferrin and RNaseB were performed by ELISA. Binding of BBP muteins Fer-P4 (circles), Fer-O20 (diamonds), Fer-N21 (squares), Fer-I21 (triangles) and Fer-N22 (inverted triangles) to ferritin (immobilized on the ELISA plate) were compared with the interaction of the muteins with transferrin (open circle) and RNaseB (open diamonds) as control (also immobilized on the ELISA plate). The BBP muteins bind ferritin in a concentration-dependent manner, whereas no significant binding signals to the unrelated targets (open symbols) were detectable. Control binding curves are only shown for BBP mutein Fer-P4, but similar results were obtained for the other muteins.

FIG. 9 shows a schematic drawing of the phage display vector pBBP42. pBBP42 codes for a fusion protein of the OmpA signal sequence, the T7 detection tag, a modified BBP according to FIG. 2, and a shortened form of the M13 coat protein pIII, comprising amino acids 217 to 406. An amber stop codon, which is partially translated into Gln in a supE amber suppressor host strain, is located between the coding region for BBP and the coding region for the truncated phage coat protein pIII. A relevant segment of the nucleic acid sequence of pBBP42 is reproduced together with the encoded amino acid sequence in the sequence listing as SEQ ID NOS: 12 (nucleotide sequence) and SEQ ID NO: 45 (amino acid sequence). The segment begins with the XbaI restriction site and ends with the HindIII restriction site. The vector elements outside this region are identical with the vector pASK75, the complete nucleotide sequence of which is exhibited in the German patent publication DE 44 17 598 A1.

FIG. 10 shows a schematic drawing of pBBP41. This vector codes for a fusion protein of the OmpA signal sequence, a modified BBP according to FIG. 1, the STREP-TAG® II and an albumin-binding domain (abd) of protein G from *Streptococcus* (Kraulis et al., FEBS Lett. 378 (1996), 190-194). An amber stop codon has been introduced between the STREP-TAG® II and the C-terminal albumin binding domain to allow soluble expression of the BBP mutein without the ABD when employing a non-supressor *E. coli* strain. A relevant segment of the nucleic acid sequence of pBBP41 is reproduced together with the encoded amino acid sequence in the sequence listing as SEQ ID NOS: 13 (nucleotide sequence) and SEQ ID NO: 46 (amino acid sequence). The segment begins with an XbaI restriction site and ends with the HindIII restriction site. The vector elements outside this region are identical with those of the vector pASK75, the complete nucleotide sequence of which is exhibited in the German patent publication DE 44 17 598 A1.

FIG. 11 shows a graphical representation of the data from Example 17, in which binding measurements with the BBP muteins and the prescribed target CD154 as well as the unrelated target BSA were performed by ELISA. Binding of BBP muteins CD154-13-10-1 (circles), CD154-13-10-3 (squares), and CD154-13-10-4 (diamonds) to CD154, which was immobilized on the ELISA plate, was compared with the interaction of the muteins with BSA (open symbols). The BBP muteins bind CD154 in a concentration-dependent manner, whereas no significant binding signals to the unrelated target were detectable.

FIG. 12 shows schematic drawings of the expression vectors (a) pASK75-strepII-CD4V, (b) pASK75-strepII-CD4D1, and (c) pASK75-strepII-CD4VD1. (a) pASK75-strepII-CD4V codes for a fusion protein made of the OmpA signal sequence, the extracellular CD4 V-domain comprising amino acids 1-101 of the mature human CD4 coreceptor (Maddon et al., Cell 42 (1) (1985), 93-104) and the STREP-TAG® II. An Ala-codon has been inserted between the last codon of the OmpA signal sequence and the first Lys codon of the mature CD4 V-domain in order to facilitate removal of the leader peptide after translocation of nascent protein to the bacterial periplasm. (b) pASK75-strepII-CD4D1 codes for a fusion protein made of the OmpA signal sequence, the extracellular CD4 D1-domain comprising amino acids 102-184 of the human CD4 coreceptor, and the STREP-TAG® II. c) pASK75-strepII-CD4VD1 codes for a fusion protein made of the OmpA signal sequence, the extracellular CD4 V-domain and D1-domain comprising amino acids 1-184 of the human CD4 coreceptor, and the Strep-tag® II. An Ala-codon has been inserted between the last codon of the OmpA signal sequence and the first Lys-codon of the mature V-domain for the same reason as described for pASK75-strepII-CD4V. Relevant segments of the nucleic acid sequences of pASK75-strepII-CD4V, pASK75-strepII-CD4D1, and pASK75-strepII-CD4-VD1, respectively, are reproduced together with their encoded amino acid sequences in the sequences listing as SEQ ID NO: 25, SEQ ID NO: 26, and SEQ ID NO: 27. Each segment begins with the XbaI-restriction site and ends with the HindIII-restriction site. The vector elements outside this region are identical with the vector pASK75, the complete nucleotide sequence of which is exhibited in the German patent publication DE 44 17 598 A1.

FIG. 13 shows a graphical representation of the data from Example 22, in which binding measurements with the BBP mutein and the prescribed target CD4-D1 as well as the unrelated target RNaseB were performed by ELISA. Binding of the immobilized BBP mutein CD4-13-F4-10 to CD4-D1 (squares) was compared with the interaction of the mutein with RNaseB (open symbols). The BBP mutein binds CD4-D1 in a concentration-dependent manner, whereas no significant binding signals to the unrelated target RNaseB were detectable.

FIG. 14 shows a graphical representation of the data from Example 27, in which binding measurements with the BBP muteins and the prescribed target CD4-VD1 as well as the unrelated target RNaseB were performed by ELISA. Binding of the immobilized BBP muteins CD4-2C3-N22 (circles), CD4-2C3-K20 (squares), CD4-2G3-H22 (triangles), and CD4-2G3-L22 (diamonds) to CD4-VD1 was compared with the interaction of the muteins with RNaseB (open symbols).

The BBP muteins bind CD4-VD1 in a concentration-dependent manner, whereas no significant binding signals to the unrelated target RNaseB (open symbols) were detectable.

Figure 15:
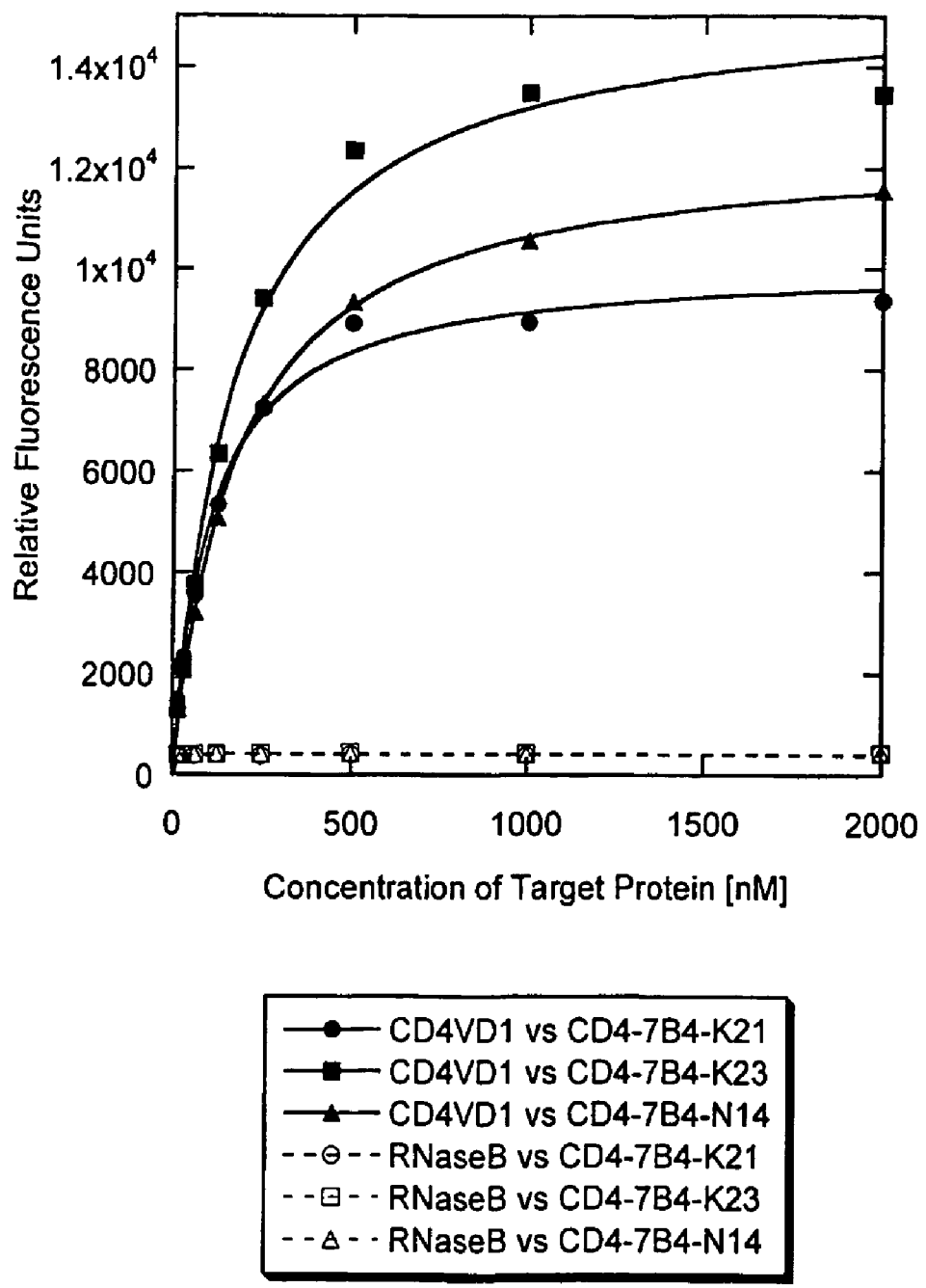
FIG. 15 depicts the binding of BBP muteins CD4-7B4-K21, CD4-7B4-K23, and CD4-7B4-N14 to CD4-VD1 in an ELISA.

FIG. 15 shows a graphical representation of the data from Example 27, in which binding measurements with the BBP muteins and the intended target CD4-VD1 as well as the unrelated control target RNaseB were performed by ELISA. Binding of the immobilized BBP muteins CD4-7B4-K21 (circles), CD4-7B4-K23 (squares), and CD4-7B4-N14 (triangles) to CD4-VD1 was compared with the interaction of the muteins with RNaseB (open symbols). The BBP muteins bind CD4-VD1 in a concentration-dependent manner, whereas no significant binding signals to the unrelated target RNaseB (open symbols) were detectable.

EXAMPLES

Example 1

Preparation of a Library with 10 Billion Independent BBP Muteins

Unless otherwise indicated, genetic engineering methods known to the person skilled in the art were used, as for example described in Sambrook et al. (Molecular Cloning. A Laboratory Manual (1989), Cold Spring Harbor Press).

Figure 3:
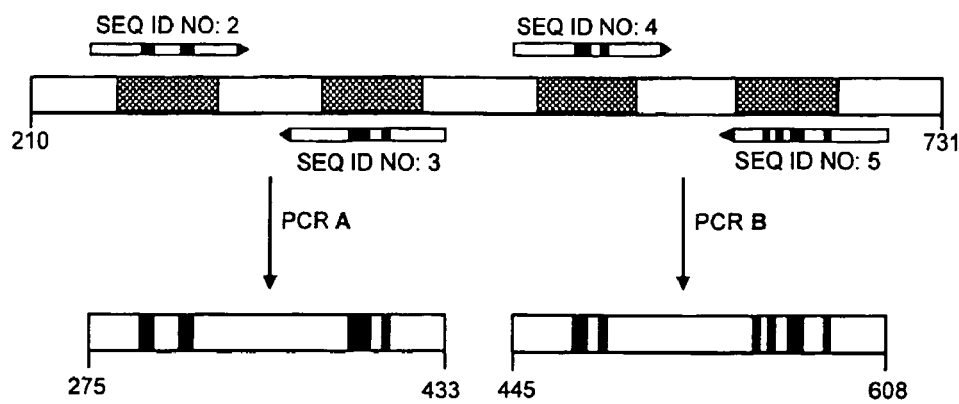
FIG. 3 schematically illustrates the preparation of the genetic library of lipocalin muteins.
Figure 3:
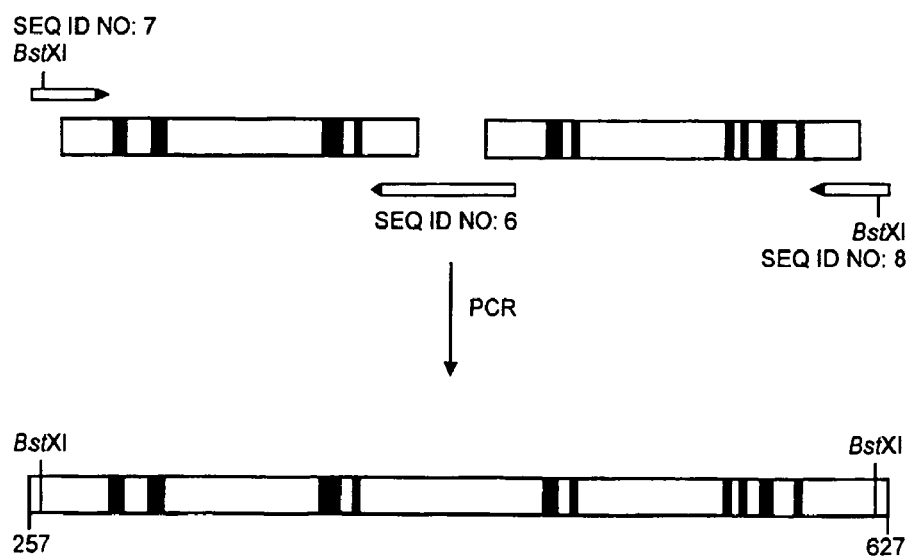
Figure 4:
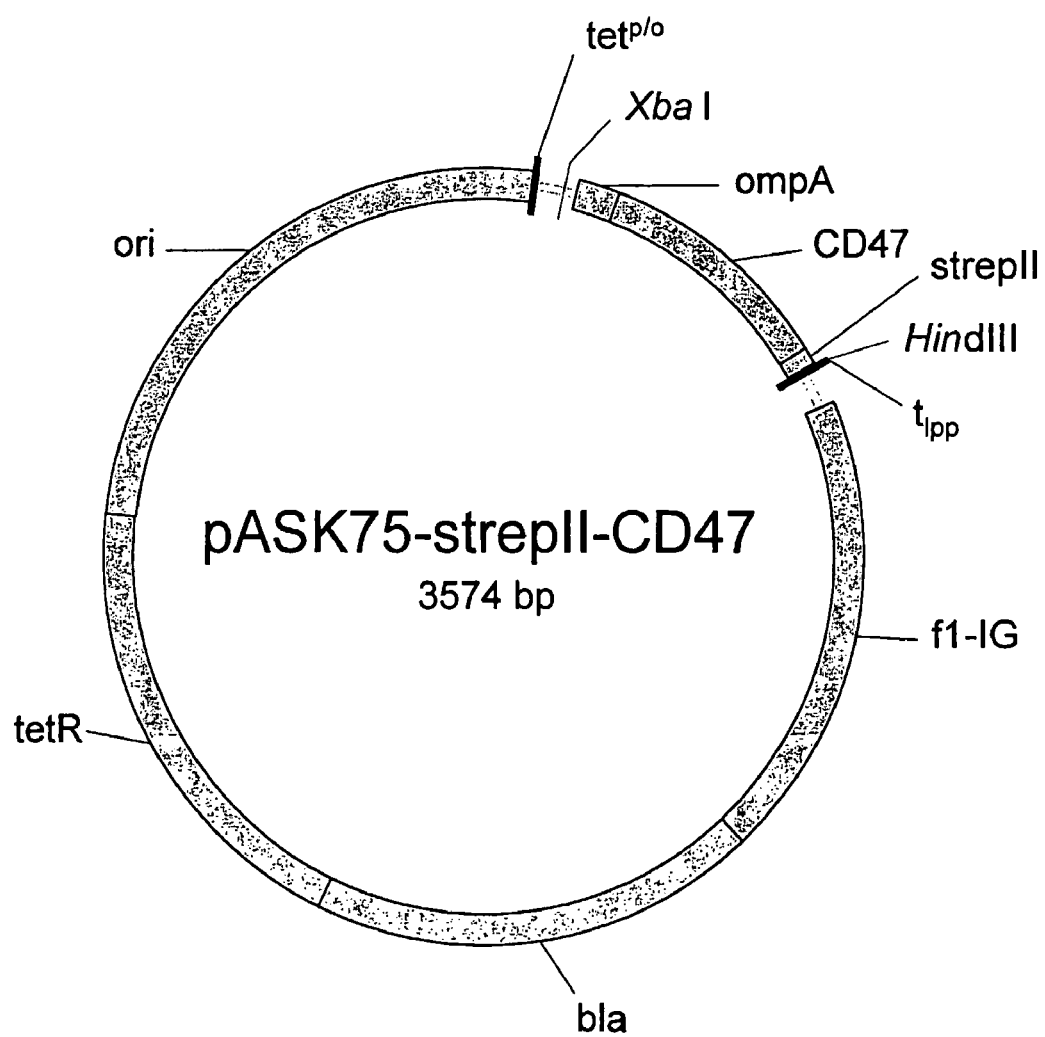
FIG. 4 schematically depicts the expression vector pASK75-strepII-CD47.

A random library of BBP with high diversity was prepared by concerted mutagenesis of in total 16 selected amino acid positions in the four peptide loops using PCR in multiple steps according to FIG. 3. The PCR reactions were carried out in a volume of 100 μl in both of the first amplification steps, wherein 10 ng pBBP20 (FIG. 1) plasmid DNA was employed as template together with 50 pmol of each pair of primers (SEQ ID NO: 2 and SEQ ID NO: 3 or SEQ ID NO: 4, and SEQ ID NO: 5, respectively), which had been synthesized according to the conventional phosphoramidite method. In addition, the reaction mixture contained 10 μl 10× Taq buffer (100 mM Tris/HCl pH 9.0, 500 mM KCl, 15 mM $MgCl_2$, 1% v/v Triton X-100) and 2 μl dNTP-Mix (10 mM dATP, dCTP, dGTP, dTTP). After bringing to volume with water, 5 u Taq DNA-polymerase (5 u/μl, Promega) were added and 20 temperature cycles of 1 minute at 94° C., 1 minute at 60° C. and 1.5 minutes at 72° C. were carried out in a thermocycler with a heated lid (Eppendorf), followed by an incubation for 5 minutes at 60° C. for final extension. The desired amplification products were isolated by preparative agarose gel electrophoresis from GTQ Agarose (Roth) using the Jetsorb DNA extraction kit (Genomed).

For the subsequent amplification step a 2000 μl mixture was prepared, wherein approximately 1000 fmol of both of these respective fragments were used as templates, in the presence of 1000 pmol of each of the assembly primers SEQ ID NO: 7, SEQ ID NO: 8 and 20 pmol of the mediating primer SEQ ID NO: 6. Both assembly primers carried a biotin group at their 5'-end, allowing subsequent purification of the PCR-product after BstXI cleavage via streptavidin-coated paramagnetic beads. Additionally 200 μl 10× Taq buffer, 40 μl dNTP-Mix (10 mM dATP, dCTP, dGTP, dTTP), 100 u Taq DNA-polymerase (5 u/μl, Promega) and 1408 μl of water were added to bring the mixture to the final volume of 2000 μl. The mixture was divided into 100 μl aliquots and PCR was performed with 20 temperature cycles of 1 minute at 94° C., 1 minute at 60° C., 1.5 minutes at 72° C., followed by a subsequent incubation for 5 minutes at 60° C. The PCR product was purified using the E.Z.N.A. Cycle-Pure Kit (PeqLab).

For the cloning of this fragment, which represented the library of the BBP muteins in nucleic acid form, it was first cut with the restriction enzyme BstXI (Promega) according to the instructions of the manufacturer and purified by preparative agarose gel electrophoresis like described above, resulting in a double stranded DNA-fragment of 335 nucleotides in size. Residual DNA-fragments which were not or incompletely digested were removed via their 5'-biotin tags by incubating their solution with streptavidin-coated paramagnetic beads (Merck), thus obtaining the doubly cut DNA fragment suitable for the subsequent ligation reaction.

To this end, 200 μl of the commercially available suspension of the paramagnetic particles in a concentration of 10 mg/ml were washed three times with 100 μl TE-buffer. The paramagnetic particles were then drained and mixed with 100 pmol of the DNA-fragment in 100 μl TE-buffer for 15 minutes at room temperature. The paramagnetic particles were collected at the wall of the Eppendorf vessel with the aid of a magnet and the supernatant containing the purified DNA fragment was recovered for further use in the following ligation reaction.

The DNA of the vector pBBP38 (FIG. 2) was cut with BstXI as described above and the larger of the two resulting fragments (3941 bp) was isolated by preparative agarose gel electrophoresis. For the ligation, 5.79 μg (26.2 pmol) of the PCR fragment and 72.82 μg (28 pmol) of the vector fragment were incubated in the presence of 765 Weiss Units of T4 DNA ligase (Promega) in a total volume of 7650 μl (50 mM Tris/HCl pH 7.8, 10 mM $MgCl_2$, 10 mM DTT, 1 mM ATP, 50 μg/ml BSA) for 64 h at 16° C. The DNA in the ligation mixture was then precipitated by adding 191 μl tRNA (yeast) of a 10 mg/ml solution in $H_2O$ (Roche), 7650 μl 5 M ammonium acetate, and 30.6 ml ethanol. Incubation at room temperature for 1 h was followed by centrifugation (30 minutes, 16000 g, 4° C.). The precipitate was washed with 5 ml ethanol (70% v/v, room temperature), centrifuged (10 minutes, 16000 g, 4° C.), and air dried until the DNA pellet appeared glossy and uncoloured. The DNA was finally dissolved in a total volume of 393 μl water to a final concentration of 200 μg/ml.

The preparation of electrocompetent cells of the *E. coli* K12 strain XL1-blue (Bullock et al., supra) was carried out according to the methods described by Tung and Chow (Trends Genet. 11 (1995), 128-129) and by Hengen (Trends Biochem. Sci. 21 (1996), 75-76). 1 l LB-medium was adjusted by addition of a stationary XL1-blue overnight culture to an optical density at 600 nm of $OD_{600}$=0.08 and was incubated at 140 rpm and 26° C. in a 2 l Erlenmeyer flask. After reaching an $OD_{600}$=0.6, the culture was cooled for 30 minutes on ice and subsequently centrifuged for 15 minutes at 4000 g and 4° C. The cell sediment was washed twice each with 500 ml ice-cold 10% w/v glycerol and was finally resuspended in 2 ml of ice-cold GYT-medium (10% w/v glycerol, 0.125% w/v yeast extract, 0.25% w/v tryptone). The cells were subsequently aliquoted (200 μl), shock-frozen in liquid nitrogen and stored at −80° C.

The Micro Pulser system (BioRad) was used in conjunction with the cuvettes from the same vendor (electrode separation 2 mm) for the electroporation. All steps were carried out at room temperature employing pre-chilled cuvettes at a temperature of −20° C. Each 10 μl of the DNA solution (2 μg) from above was mixed with 100 μl of the cell suspension, incubated for 1 minute on ice, and transferred to the pre-chilled cuvette. Then the electroporation was performed (5 ms, 12.5 kV/cm) and the suspension was immediately diluted in 2 ml of SOC-medium followed by shaking for 60 minutes at 37° C. and 140 rpm. Afterwards, the culture was diluted in 4 l 2×YT-medium containing 100 μg/ml ampicillin (2YT/

Amp) resulting in an $OD_{550}$ of 0.26. By employing in total 78.61 μg of the ligated DNA, $1 \cdot 10^{10}$ transformants were obtained in this manner using altogether 40 electroporation runs.

The culture containing the cells which were transformed with the phasmid vectors corresponding to pBBP38, but coding for the library of the BBP muteins as fusion proteins, was incubated at 37° C. and 140 rpm until the $OD_{550}$ reached ca. 0.76. 1 l of this culture was transferred to a sterile Erlenmeyer flask and incubated at 37° C. and 140 rpm until an $OD_{550}$ of 2.0 (ca. $1.2 \cdot 10^{12}$ bacterial clones) was reached. The culture was centrifuged (15 minutes, 5000 g, 4° C.) and the cell pellet was resuspended carefully in 12 ml of 2×YT at ambient temperature containing 20% v/v glycerol. Afterwards, the suspension was equally distributed to 12 cryotubes at a volume of 1.25 ml, shock-frozen in liquid nitrogen and finally stored at −80° C.

For the production of phagemids displaying the BBP muteins on their surface, 3 of the cryotube vials described above containing in total ca. $3 \cdot 10^{11}$ transformed bacterial clones were thawed on ice and the suspensions were used to inoculate 3 l of 2×YT with an initial $OD_{550}$ of 0.16. The culture was shaken at 37° C. and 140 rpm until the $OD_{550}$ reached 0.6. After infection with VCS-M13 helperphage (Stratagene) at a multiplicity of infection (moi) of approximately 10 the culture was shaken for additional 45 minutes at 37° C. at 100 rpm. Then the incubator temperature was lowered to 26° C. and 2 ml of a 35 mg/ml stock solution of kanamycin was added per liter of culture to reach a final concentration of 70 μg/ml. After 10 minutes, anhydrotetracycline (ACROS Organics) was added at 25 μg/l (37.5 μl of a 200 μg/ml stock solution in dimethylformamide, DMF) in order to induce gene expression. Incubation continued for another 12 hours at 26° C., 160 rpm.

The cells were sedimented by centrifugation (30 minutes, 18000 g, 4° C.) and the supernatant containing the phagemid particles was sterile-filtered (0.45 μm). Afterwards, the culture was mixed with ¼ volume (375 ml) ice-cold 20% w/v PEG 8000, 15% w/v NaCl and incubated on ice for one hour. After centrifugation (30 min, 18000 g, 4° C.) the precipitated phagemid particles were dissolved in 90 ml of ice cold BBS/E (20 mM borate pH 8.0, 160 mM NaCl, 1 mM EDTA) containing 50 mM benzamidine (Sigma). The solution was incubated on ice for 60 minutes and was distributed into two SS34 centrifugation tubes. After centrifugation of undissolved components (10 min, 18000 g, 4° C.) the supernatants were transferred to a new centrifugation tube. The phagemid particles were reprecipitated by mixing with ¼ volume 20% w/v PEG 8000, 15% w/v NaCl and incubation for 60 minutes on ice, divided in aliquots of 2 ml with a titer of ca. $5 \cdot 10^{12}$ colony forming units (cfu) per ml, and stored at −80° C.

Example 2

Production and Purification of the Extracellular Domain of CD47

For the production of CD47 as a target protein for the isolation of CD47-specific BBP muteins, cells of the *E. coli* strain JM83 (Yanisch-Perron et al., Gene 33 (1985), 103-119) were transformed with the expression plasmid pASK75-strepII-CD47 (FIG. 5) harbouring the cDNA coding for the extracellular domain of CD47 (AS 1-119 of the mature protein) with a single mutation coding for an alanine instead of a cysteine at position 15 (for the CD47 cDNA, see Lindberg et al., J. Cell Biol. 123 (2) (1993), 485-496). 100 ml of LB-medium containing 100 μg/ml ampicillin (LB/Amp) was inoculated with a single colony of the JM83 transformant carrying the plasmid described above, and incubated overnight at 37° C., 160 rpm. 2 l of LB/Amp-medium in a 5 l-Erlenmeyer flask were then inoculated with 40 ml of this preculture and were shaken at 26° C., 160 rpm to an $OD_{550}$=0.4. Then the temperature was lowered to 22° C. and when an $OD_{550}$=0.5 was reached, production of the recombinant protein was induced by adding 200 μg/l anhydrotetracycline (200 μl of a 2 mg/ml stock solution in DMF) followed by shaking for 3-4 further hours at 22° C. and 160 rpm.

The cells from one flask were centrifuged (10 minutes, 5500 g, 4° C.) and, after decanting the supernatant, were resuspended in 20 ml of periplasmic release buffer (100 mM Tris/HCl pH 8.0, 500 mM sucrose, 1 mM EDTA) followed by cooling on ice for 30 minutes. Subsequently the spheroplasts were removed in two successive centrifugation steps (25 minutes, 5300 g, 4° C. and 10 minutes, 27000 g, 4° C.). The supernatant comprising the periplasmic protein extract was dialyzed against SA-buffer (100 mM Tris/HCl pH 8.0, 150 mM NaCl, 1 mM EDTA), sterile-filtered, and subjected to chromatographic purification.

The purification took place by means of the STREP-TAG® II-affinity tag (Skerra and Schmidt, Methods Enzymol. 326 (2000), 271-304), introduced at the C-terminus of the CD47 protein, employing Streptactin Superflow material (IBA). A chromatographic column with a bed volume of 8 ml was filled with this affinity matrix and equilibrated with 20 ml SA-buffer at 4° C. at a flow rate of 60 ml/h. Chromatography was monitored by measuring the absorption at 280 nm of the eluate in a flow-through photometer. After the application of the periplasmic protein extract, the column was washed with SA-buffer until the base line was reached and the bound CD47 was subsequently eluted with ca. 15 ml of a solution of 2.5 mM D-desthiobiotin (IBA) in SA-buffer collecting fractions of the eluate. The fractions containing purified CD47 were checked via SDS-polyacrylamide gel electrophoresis (Fling und Gregerson, Anal. Biochem. 155 (1986), 83-88), subsequently combined and dialysed against an appropriate buffer if needed. The protein yield was approximately 370 μg per 1 l culture.

Example 3

Phagemid Presentation and Selection of BBP Muteins Against the Extracellular Domain of Human CD47 Employing Polystyrol Sticks A 2 ml aliquot of the stored phagemids from Example 1 containing $10^{13}$ phagemids was centrifuged (30 minutes, 21460 g, 4° C.), the supernatant was removed, and the sedimented phagemid particles were dissolved in 1 ml PBS (4 mM $KH_2PO_4$, 16 mM $Na_2HPO_4$, 115 mM NaCl, pH 7.4). After incubation for 30 minutes on ice the solution was centrifuged (5 minutes, 18500 g, 4° C.) to remove residual aggregates.

Immuno-sticks (NUNC) were used for the affinity enrichment of the recombinant phagemids displaying the BBP mutein fusion proteins and were therefore coated overnight at 4° C. with 800 μl of the extracellular domain of human CD47 (CD47) (100 μg/ml) in SA-buffer as a target protein. Unoccupied binding sites on the surface of the Immuno-Stick were saturated by incubation with 1.2 ml 2% w/v BSA in PBST (PBS with 0.1% v/v Tween 20) for 2 hours at room temperature. Afterwards, the Immuno-stick was briefly washed three times with 1.2 ml PBST and subsequently incubated with a mixture of 500 μl of the phagemid solution (ca. $5 \cdot 10^{12}$ cfu)

and of 250 µl of PBS containing 6% w/v BSA and 0.3% v/v Tween 20 for 1 hour at room temperature.

For the removal of unbound phagemids, washing was performed eight times, each time with 950 µl PBST for 2 minutes. Adsorbed phagemids were finally eluted by treating the Immuno-stick for 10 minutes with 950 µl 0.1 M glycine/HCl pH 2.2, followed by immediate neutralisation of the pH of the elution fraction by mixing it with 150 µl 0.5 M Tris.

For the amplification, this phagemid solution (1.1 ml, containing between $10^6$ and $10^8$ cfu, depending on the selection cycle) was shortly warmed to 37° C., mixed with 3 ml of an exponentially growing culture of E. coli XL1-blue ($OD_{550}$=0.5), and incubated for 30 minutes at 37° C., 140 rpm. The cells infected with the phagemids were subsequently sedimented (2 minutes, 4420 g, 4° C.), resuspended in 600 µl of the culture medium, and plated out onto three agar plates with LB/Amp-medium (LB/Amp agar; 145 mm diameter).

After incubation for 14 hours at 32° C., the cells were scraped from the agar plates, each with addition of 10 ml 2×YT/Amp, were transferred to a sterile Erlenmeyer-flask, and were shaken for 30 minutes at 37° C., 140 rpm for complete suspension. For the repeated production and affinity enrichment of phagemid particles 50 ml of 2×YT/Amp were inoculated to an $OD_{550}$ of ca. 0.08 with an appropriate volume of this suspension and incubated at 37° C., 160 rpm until $OD_{550}$ reached 0.5.

After infection with VCS-M13 helper phage (Stratagene) at a moi of approximately 10 the culture was shaken for additional 45 minutes at 37° C., 140 rpm. Kanamycin (70 µg/ml) was subsequently added, the incubator temperature was lowered to 26° C. and, after 10 minutes, anhydrotetracycline was added at 25 µg/l (6.2 µl of a 0.2 mg/ml stock solution in DMF) in order to induce gene expression. Incubation continued for another 12-15 hours at 26° C., 140 rpm.

The cells were sedimented by centrifugation (15 minutes, 12100 g, 4° C.) and the supernatant containing the phagemid particles was sterile-filtered (0.45 µm), mixed with ¼ volume (12.5 ml) 20% w/v PEG 8000, 15% w/v NaCl, and incubated on ice for 1 hour. After centrifugation (20 minutes, 18000 g, 4° C.) the precipitated phagemid particles were dissolved in 2 ml of cold BBS/E. The solution was distributed to two 1.5 ml reaction vessels and incubated on ice for 30 minutes. After centrifugation of undissolved components (5 minutes, 21460 g, 4° C.) each supernatant was transferred to a new reaction vessel.

Mixture with ¼ volume 20% w/v PEG 8000, 15% w/v NaCl and incubation for 30 to 60 minutes on ice served to reprecipitate the phagemid particles. After centrifugation (20 minutes, 21460 g, 4° C.) the supernatant was removed and the precipitated phagemid particles were dissolved and combined in a total of 1 ml PBS. After incubation for 30 minutes on ice the solution was centrifuged (5 minutes, 21460 g, 4° C.) in order to remove residual aggregates and the complete supernatant containing between $10^{11}$ and $5·10^{12}$ phagemids was directly used for the next round of affinity enrichment. Five further selection cycles with the target CD47 were carried out in this way.

Example 4

Figure 5:
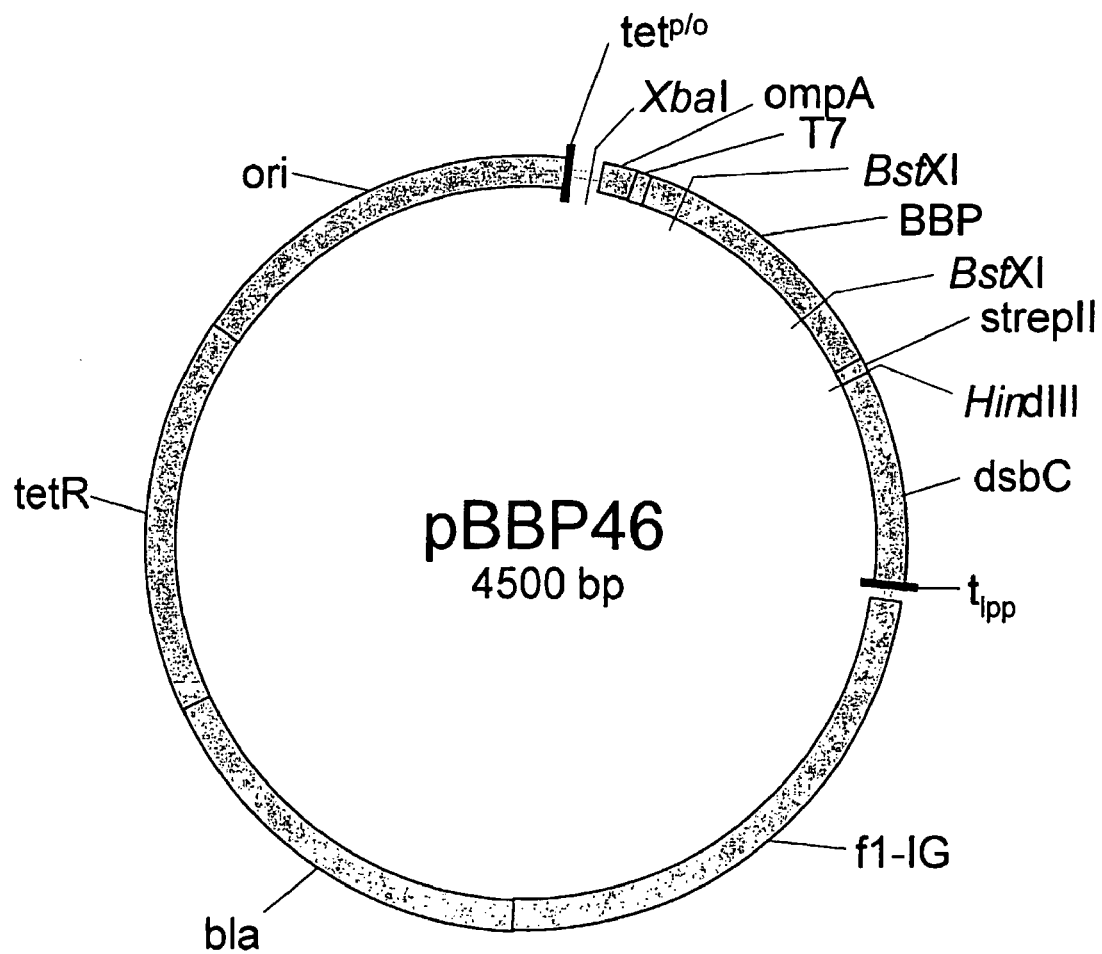
FIG. 5 schematically depicts the expression vector pBBP46.

Identification of CD47-Binding BBP Muteins by Use of a High-Throughput ELISA Screening Method For the analytical production of the BBP muteins equipped with an N-terminal T7 detection tag (Novagen) as well as a C-terminal STREP-TAG® II affinity tag and their characterization by high-throughput ELISA screening, the gene cassette between the two BstXI cleavage sites was subcloned from the vector pBBP38 on pBBP46 (FIG. 5).

For this purpose the plasmid DNA was isolated from the mixture of the E. coli clones obtained by infection with the phagemids from Example 3 eluted as a result of the last selection cycle, using the Plasmid Miniprep Spin kit (Genomed). The DNA was cut with the restriction enzyme BstXI and the smaller of the two fragments (335 bp) was purified by preparative agarose-gel electrophoresis as described in Example 1. The DNA of the vector pBBP46 was likewise cut with BstXI and the larger of the two fragments (4165 bp) was isolated in the same way.

For the ligation, 50 fmol each of the two DNA-fragments were mixed with 3 Weiss Units T4 DNA ligase (Promega) in a total volume of 20 µl (30 mM Tris/HCl pH 7.8, 10 mM $MgCl_2$, 10 mM DTT, 1 mM ATP), followed by incubation for 2 h at 22° C. E. coli TG1-F⁻ (E. coli K12 TG1, which had lost its episome) was transformed with 5 µl of this ligation mixture according to the $CaCl_2$-method (Sambrook et al., supra) and plated on LB/Amp agar plates (22 cm×22 cm).

Single E. coli colonies obtained after the transformation harbouring the pBBP46 plasmids coding for the BBP muteins were picked from these agar plates into 70 µl per well 2×YT/Amp in flat bottom 384 well plates (Greiner) by means of an automated colony picker (Genetix) and grown overnight at 37° C. at 700 rpm on a benchtop shaker (Bühler) in a humidified incubator (MMM Medcenter) at 60% relative humidity (rH). The cultures were diluted 1:100 into 100 µl 2×YT/Amp in round bottom 96 well plates (Nunc) by means of a 96 pin replicating head (Genetix) and grown for ca. 1 h at 37° C. and 60% rH, followed by an incubation for 3 h at 22° C. and 60% rH, both at 700 rpm, until the $OD_{550}$ reached approximately 0.6. The 384 well plates were kept as "master" plates at −80° C. after adding 25 µl 60% v/v glycerol to each well.

Recombinant BBP muteins were produced in the 96 well plates by adding 20 µl per well of 1.2 µg/ml anhydrotetracycline in 2×YT (obtained by diluting a 2 mg/ml stock solution 1:1667 in 2×YT; final concentration 0.2 µg/ml) to the bacterial cultures and incubation overnight at 22° C. and 700 rpm at 60% rH. Afterwards, 40 µl of lysis buffer (400 mM Na-borate pH 8.0, 320 mM NaCl, 4 mM EDTA, 0.3% w/v lysozyme) was added to each well and the plate was incubated for 1 h at 22° C. and 700 rpm at 60% rH. To minimize non-specific binding interactions in the subsequent ELISA experiment, obtained crude cell extracts were supplemented with 40 µl/well PBS containing 10% w/v BSA and 0.05% v/v Tween 20 (final concentration 2% BSA) for 1 h at 22° C. and 700 rpm at 60% rH.

For the detection of binding, the crude cell extracts containing the BBP muteins were tested for their reactivity with the prescribed target protein CD47 and the unrelated control protein aldolase (Roche), respectively, in ELISA experiments. Therefore, wells of black Fluotrac 600 ELISA plates (Greiner; 384 well) were coated overnight with 20 µl of a solution of recombinant CD47 (produced as described in Example 2) or the control protein at 4° C., each at a concentration of 20 µg/ml in PBS. Plates were washed five times with 100 µl PBS containing 0.05% v/v Tween 20 (PBST/0.05) per well with an automated ELISA plate washer (Molecular Devices) leaving a residual volume of 10 µl of the washing buffer in each well after the last washing step. Residual binding sites were blocked by incubation with 100 µl PBST/0.05 containing 2% w/vBSA for 2 h at room temperature. Afterwards, plates were again washed five times as described above.

For complex formation between the BBP muteins and the immobilized proteins, the wells were incubated with 10 μl of the cell extract described above for 1 hour at room temperature. Subsequently, plates were washed again five times and 10 μl of an anti-T7 monoclonal antibody-HRP-conjugate (Amersham), diluted 1:5000 in PBST/0.05 containing 0.5% w/v non-fat dry milk powder (Vitalia), was added to each well and incubated for 1 hour at room temperature. Plates were again washed five times and 10 μl of the fluorogenic HRP-substrate QuantaBlu™ (Pierce, diluted as described by the manufacturer) was added to detect bound BBP muteins by means of the attached anti-T7 monoclonal antibody-HRP-conjugate. After 60 minutes at room temperature fluorescence was excited at a wavelength of 320 nm (±12.5 nm) and measured at 430 nm (±17.5 nm) in a GENiosPlus plate reader (Tecan).

22 of 736 analyzed BBP muteins showed a binding signal on the prescribed target protein (CD47) which exceeded the binding signal on the unrelated control protein (aldolase) at least by a factor of three (signal-to-control ratio of at least 3) and were subsequently subjected to a secondary high-throughput ELISA screening experiment in order to study the binding specificity of these muteins in greater detail. Therefore, these clones were transferred from the 384 well master plates described above onto LB/Amp agar, and grown overnight at 37° C. 100 μl 2×YT/Amp in round bottom 96 well plates (Nunc) was inoculated with single colonies from these agar plates and grown overnight at 37° C. at 700 rpm and 60% rH. The cultures were diluted 1:100 into 100 μl 2×YT/Amp in round bottom 96 well plates (Nunc) and production of recombinant BBP muteins as well as preparation of the bacterial lysates was performed as described above.

For the detection of target-specificity of the BBP muteins, wells of black Fluotrac 600 ELISA plates (Greiner; 384 well) were coated overnight at 4° C. with 20 μl of a solution of recombinant CD47 or, as a control, with BSA (Roth), transferrin (Roche), aldolase (Roche), ovalbumin (Sigma), recombinant CD4 VD1 (produced as described in Example 18) as well as a conjugate of RNaseA (Fluka) and digoxigenin, each at a concentration of 20 μg/ml in PBS.

This conjugate was prepared by reacting RNaseA at a twofold molar ratio of digoxigenin-3-O-methylcarbonyl-ε-amidocaproic acid-N-hydroxy-succinimide ester (DIG-NHS; Roche) according to the instructions of the manufacturer. Excess reactant was removed from the RNaseA-conjugate by means of size exclusion chromatography using a HiTrap column (Amersham) according to the instructions of the manufacturer employing PBS as running buffer.

After overnight incubation, the plates were washed as described above and blocked by the addition of 100 μl/well PBST/0.05 containing 2% w/v BSA at the conditions described above, followed again by washing of the plates. 10 μl of the blocked bacterial lysates of the 22 BBP muteins mentioned above were transferred to each of the wells coated with either CD47 or the unrelated control proteins and incubated for 1 h at ambient temperature. Bound BBP muteins were detected with anti-T7 monoclonal antibody-HRP-conjugate and the fluorogenic HRP-substrate QuantaBlu™ as described above.

10 BBP muteins revealing the highest binding signals on the prescribed target CD47 versus the control proteins were selected for sequence analysis. Therefore, 4 ml LB/Amp were inoculated with 40 μl of the glycerol stock from the respective well of the 384 well master plate and cultured for subsequent isolation of the plasmid DNA as described at the beginning of this example. The DNA sequence of the BBP gene cassette was elucidated by using the oligodeoxynucleotide SEQ ID NO: 14 as primer on an automated Genetic Analyzer system (Applied Biosystems) according to the instructions of the manufacturer employing the Big Dye Terminator Cycle Sequencing Kit (Applied Biosystems).

Three of the sequenced clones carried a functional insert and were named CD47-F2, CD47-A9 and CD47-F11. The nucleotide sequences of these clones were translated into the amino acid sequence and those amino acids deviating from BBP are given in Table 1. The sequencing revealed amber stop codons, which were suppressed in the employed *E. coli* strains XL1-blue and TG1-F⁻ and translated into Gln, at different positions in all of the selected variants. The nucleotide and amino acid sequences of CD47-F2, CD47-A9 and CD47-F11 are also given as SEQ ID NOS: 15 (nucleotide sequence) and SEQ ID NO: 47 (amino acid sequence), SEQ ID NOS: 16 (nucleotide sequence) and SEQ ID NO: 48 (amino acid sequence) and SEQ ID NOS: 17 (nucleotide sequence) and SEQ ID NO: 49 (amino acid sequence) in the sequence listing.

The clones CD47-F2, CD47-A9 and CD47-F11 were chosen for the determination of their binding affinity for CD47 as described in Example 8.

TABLE 1

Sequence characteristics of selected BBP muteins with specificity for CD47

| Pos. | BBP | CD47-F2 | CD47-F11 | CD47-A9 |
|---|---|---|---|---|
| 35 | Ser | Gln* | Gln* | Val |
| 36 | Val | Glu | Gly | Gln* |
| 38 | Lys | Leu | Pro | Trp |
| 39 | Tyr | Arg | Pro | Thr |
| 63 | His | Arg | Ser | Ser |
| 64 | Gly | Ala | Arg | Phe |
| 65 | Lys | Gln | Tyr | Lys |
| 67 | Tyr | Ser | Arg | Arg |
| 69° | Ile | Ile | Ile | ΔΔΔ |
| 72° | Thr | Ser | Thr | Thr |
| 79° | Ser | Ser | Ser | Pro |
| 90 | Tyr | Tyr | Val | Leu |
| 91 | Gly | Phe | Gly | Arg |
| 93 | Val | Leu | Tyr | Trp |
| 116 | Lys | Ala | Ser | Thr |
| 118 | Asp | Arg | Leu | Arg |
| 120 | Asp | Leu | Tyr | Trp |
| 121 | Lys | Leu | Leu | Ala |
| 125 | Gln | Gly | Leu | Phe |

°These amino acid substitutions arose from accidental mutations outside the randomized positions.
ΔThis amino acid deletion arose due to an accidental mutation outside the randomized positions.
*These glutamine residues were encoded by amber stop codons.

Example 5

Selection of BBP Muteins Against the Extracellular Domain of Human CD47 Employing Polystyrol Multiwell Plates A 2 ml aliquot of the precipitated phagemids from Example 1 (about $10^{13}$ cfu) was centrifuged (20 minutes, 21460 g, 4° C.), the supernatant was removed, and the sedimented phagemid particles were dissolved in 2 ml PBS. After incubation for 30 minutes on ice the solution was centrifuged (5 minutes, 21460 g, 4° C.) to remove residual aggregates and the supernatant was directly used for the affinity enrichment.

High binding polystyrol microtiter plates (Greiner) were used for the affinity enrichment of the recombinant phagemids carrying the BBP mutein fusion proteins. Five wells were coated overnight at ambient temperature with 300 µl each of recombinant CD47 at a concentration of 100 µg/ml in SA-buffer, which was produced as described in Example 2.

Unoccupied binding sites on the surface of the wells were saturated by incubation with 350 µl/well 2% w/v BSA in PBST for 2 hours at room temperature under shaking at 600 rpm on a Titramax 1000 shaker (Heidolph). Afterwards, the wells were washed three times by incubation for 2 min with 350 µl PBST per well at room temperature and 600 rpm and subsequent removal of the buffer. Afterwards, each well was incubated with a mixture of 200 µl of the phagemid solution (ca. $1·10^{12}$ cfu per well; $5·10^{12}$ in total) and of 100 µl of PBS containing 6% w/v BSA and 0.3% v/v Tween 20 for 1 hour at room temperature.

For the removal of unbound phagemids, washing was performed eight times as described above, each time with 350 µl PBST per well for 2 minutes. Adsorbed phagemids were finally eluted by a 10 minute treatment of the microtiter plate with 300 µl of 0.1 M glycine/HCl pH 2.2 per respective well, followed by immediate neutralisation of the pH of each elution fraction by mixing it with 47 µl 0.5 M Tris.

For the amplification, the combined phagemid solution (ca. 1.8 ml, containing between $10^5$ and $10^8$ cfu, depending on the selection cycle) was shortly warmed to 37° C., mixed with 5 ml of an exponentially growing culture of *E. coli* XL1-blue ($OD_{550}$=0.5), and incubated for 30 minutes at 37° C., 140 rpm. The cells infected with the phagemids were subsequently sedimented (2 minutes, 4420 g, 4° C.), resuspended in 600 µl of the culture medium, and plated out onto three agar plates with LB-medium containing 100 µg/ml ampicillin (145 mm diameter).

After incubation for 14 hours at 32° C., the cells were scraped from the agar plates and the repeated production of phagemid particles for subsequent enrichment cycles was performed as described under Example 3 with the exception that the phagemid containing culture was sedimented by centrifugation for 30 min at 5000 g and 4° C. (instead of 15 minutes at 12100 g and 4° C.) prior to sterile-filtration (0.45 µm).

Four further selection rounds were carried out in this way employing the complete preparation of amplified phagemids from the respective previous enrichment cycle containing between $10^{11}$ and $5·10^{12}$ phagemids with the exception that beginning with the third round only three wells of a high binding polystryrol microliter plate were coated with CD47 and that as a result only ca. 1 ml of combined phagemid solution was obtained after the elution step.

For subsequent screening of the selected muteins by high-throughput phage-ELISA screening, the combined phagemid solution of the fifth enrichment cycle was shortly warmed to 37° C., mixed with 5 ml of an exponentially growing culture of *E. coli* XL1-blue ($OD_{550}$=0.5), and incubated for 30 minutes at 37° C., 140 rpm. The cells infected with the phagemids were sedimented (2 minutes, 4420 g, 4° C.), resuspended in 600 µl of the culture medium, and 200 µl of a 1:10 dilution of this culture in LB-medium was plated out onto large LB/Amp agar plates (22 cm×22 cm).

Example 6

Figure 2:
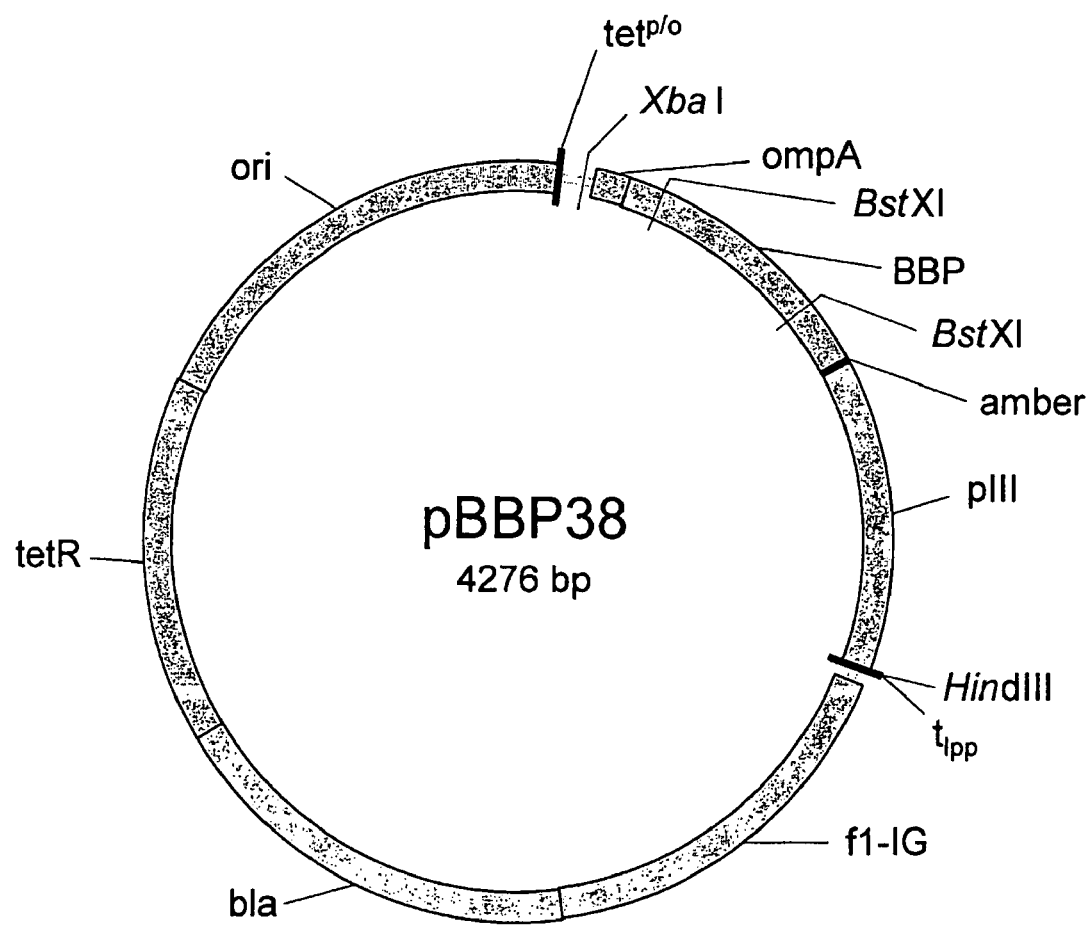
FIG. 2 schematically depicts the phasmid vector pBBP38.

Identification of CD47-Binding BBP Muteins by Use of a "High-Throughput Phage-ELISA Screening"-Method Single clones harbouring the pBBP38 plasmids (FIG. 2) coding for the BBP muteins were used for the analytical production of phagemid particles displaying the BBP muteins on their surface and their characterization by high-throughput phage-ELISA screening. Therefore, single colonies were picked from the large LB/Amp agar plates described in Example 5 into 50 µl 2×YT/Amp per well in flat bottom 384 well plates (Greiner) and grown overnight at 37° C. and 700 rpm, 60% rH, as described in Example 4. These plates were kept as "master" plates at −80° C. after adding glycerol to a final concentration of 15% v/v.

The cultures were diluted ca. 1:100 into 90 µl 2×YT/Amp per well in round bottom 96 well plates (Nunc) by means of a 96 pin replicating head (Genetix) for small-scale phage production. The obtained 96 well "daughter plates" were grown for ca. 4 h at 37° C. and 60% rH until individual cultures reached an $OD_{550}$ of at least 0.5. For infection, bacterial cultures were then incubated for 45 minutes at 37° C. without shaking together with 20 µl VCS-M13 helperphage ($2.5·10^{10}$ pfu/ml) per well.

Phagemids displaying recombinant BBP muteins were produced by adding 20 µl per well of kanamycin (525 µg/ml in 2×YT, obtained by dilution of a 35 mg/ml stock solution; final concentration 70 µg/ml) and 20 µl per well anhydrotetracycline (188 ng/ml in 2×YT, obtained by dilution of a 0.2 mg/ml stock solution in DMF; final concentration 25 ng/ml) to the infected bacterial cultures and overnight incubation at 26° C. and 700 rpm, 60% rH. After centrifugation of the 96 well "daughter" plates (15 minutes, 3500 g, 4° C.), 120 µl of the phagemid containing supernatants were transferred to fresh round bottom 96 well plates (Nunc). To minimize non-specific binding interactions in the subsequent ELISA experiment, 120 µl PBS containing 4% w/v skimmed milk powder (Marvel) and 0.2% v/v Tween 20 was added to the phagemid solution in each respective well and incubated for 2 h at room temperature.

For the detection of binding phagemids displaying the BBP muteins were tested for their reactivity with the prescribed target protein CD47 and the unrelated control protein aldolase, respectively, in phage-ELISA experiments. Therefore, wells of black Fluotrac 600 ELISA plates (Greiner; 384 well) were coated overnight at 4° C. with 20 µl of a solution of recombinant CD47 (produced as described in Example 2) or aldolase (Roche), each at a concentration of 5 µg/ml in PBS. Plates were washed 3 times with 100 µl PBST/0.05 with an ELISA plate washer and residual binding sites were blocked by incubation with 100 µl PBS containing 2% w/v skimmed milk powder and 0.1% v/v Tween 20 (M/PBST) for 1 hour at room temperature. Afterwards, plates were again washed 3 times with 100 µl PBST/0.05 leaving a residual volume of 10 µl of the washing buffer.

For complex formation between the BBP muteins displayed on the phagemids and the immobilized proteins, plates were incubated with 20 µl of the phagemid solution from above (ca. $2·10^8$ cfu) for 1 hour at room temperature. Subsequently, plates were washed five times with 100 µl PBST/0.05. Afterwards, 20 µl of an anti-M13 monoclonal antibody-HRP-conjugate (Amersham), diluted 1:5000 in M/PBST, was added to each well and incubated for 1 hour at room temperature. Plates were washed five times with 100 µl PBST/0.05 and 20 µl of the fluorogenic HRP-substrate QuantaBlu™ (Pierce, diluted as described by the manufacturer) was added to detect bound BBP muteins by means of the attached phagemids. After incubation for 45 minutes at room temperature fluorescence was excited at a wavelength of 320 nm (±12.5 nm) and measured at 430 nm (±17.5 nm) in a GENios-Plus plate reader.

Five out of the 736 tested *E. coli* clones produced phagemids which gave rise to intense binding signals on CD47 with low cross-reactivity on the unrelated control protein aldolase and were selected for more detailed characterisation. Therefore, 100 µl LB/Amp in round bottom 96 well plates (Nunc) were inoculated with the respective cultures from the 384 well master plates by means of a 96-pin picking head (Genetix) and grown overnight at 37° C. at 60% rH, 700 rpm. Subsequently 4 ml LB/Amp was inoculated with 5 µl of the obtained cultures, incubated overnight at 37° C. and 160 rpm and used for subsequent isolation of the plasmid DNA as described under Example 4.

The BBP gene cassette was subjected to sequence analysis using the oligodeoxynucleotide SEQ ID NO: 14 as primer as described in Example 4. The clone showing the highest binding signals exhibited a sequence according to the applied mutagenesis strategy and was named CD47-G6, while the others revealed frame shift mutations encoded by the random oligodeoxynucleotides, which were employed for the production of the library of BBP muteins, and where not considered any further. The nucleotide sequence of CD47-G6 was translated into the amino acid sequence and those amino acids deviating from BBP are given in Table 2. The nucleotide and ammo acid sequences of the mutein CD47-G6 is also given as SEQ ID NOS: 18 (nucleotide sequence) and SEQ ID NO: 50 (amino acid sequence).

BBP mutein CD47-G6 was subjected to analysis of its binding affinity for CD47 as described in Example 8.

TABLE 2

Sequence characteristics of selected anti-CD47 mutein

| Pos. | BBP | CD47-G6 |
|---|---|---|
| 35 | Ser | Arg |
| 36 | Val | Arg |
| 38 | Lys | Lys |
| 39 | Tyr | Phe |
| 63 | His | Arg |
| 64 | Gly | Trp |
| 65 | Lys | Gly |
| 67 | Tyr | Arg |
| 69° | Ile | Ile |
| 72° | Thr | Ser |
| 79° | Ser | Ser |
| 90 | Tyr | Leu |
| 91 | Gly | Pro |
| 93 | Val | Tyr |
| 116 | Lys | Lys |
| 118 | Asp | Leu |
| 120 | Asp | Arg |
| 121 | Lys | Leu |
| 125 | Gln | Ala |

°These amino acid substitutions arose from accidental mutations outside the randomized positions.

Example 7

Production of the BBP Muteins

For the preparative production of the mutein CD47-G6 obtained from Example 6 the mutagenized coding region between the two BstXI cleavage sites was subcloned from the vector pBBP38 on the expression plasmid pBBP46 as described under Example 4. The obtained plasmid thus encoded a fusion protein of the mutein with the OmpA signal sequence and the T7-tag at the N-terminus as well as the STREP-TAG® II at the C-terminus. The muteins CD47-F2, CD47-A9 and CD47-F11 obtained from Example 4 were already encoded on the expression vector pBBP46 and thus directly suited for subsequent preparative production and affinity testing.

Single colonies of *E. coli*-TG1F⁻ transformed with the pBBP46 plasmids coding either for the BBP mutein CD47-G6, CD47-F2, CD47-A9 or CD47-F11 were used for inoculating each 100 ml of LB/Amp-medium, followed by incubation overnight at 37° C., 160 rpm. 2 l of LB/Amp-medium in a 5 l-Erlenmeyer flask were inoculated with 40 ml of this preculture and were shaken at 26° C., 160 rpm to an $OD_{550}$=0.4. Then the temperature was lowered to 22° C. and production of the recombinant protein was induced at an $OD_{550}$ of 0.5 by adding 200 µg/l anhydrotetracycline (200 µl of a 2 mg/ml stock solution in DMF) followed by shaking for 3 further hours at 22° C., 160 rpm. Harvesting of the bacterial cells as well as purification of the recombinant proteins was performed as described under Example 2. The protein yield was approximately 30-100 µg per 1 l culture.

Example 8

Measurement of the Affinity of the BBP Muteins for CD47 in ELISA

For the detection of binding in an ELISA the wells of a black Fluotrac 600 microtiter plate (Greiner; 384 well) were filled each with 20 µl of a solution of the intended recombinant protein target CD47 (produced as described in Example 2) or the unrelated control protein BSA both at a concentration of 50 µg/ml in PBS and were incubated for 1 h at ambient temperature. After washing five times with 100 µl PBST/0.05 per well employing an automated ELISA plate washer, the wells were filled with 100 µl PBST/0.05 3% w/v non-fat dry milk powder (Vitalia), in order to saturate unspecific binding sites and incubated for one hour at room temperature. After blocking, the microtiter plate was washed two times with 100 µl PBST/0.05 as described above.

Then a dilution series of the muteins in SA-buffer from Example 7 was prepared in PBST starting from 2000 nM concentration and incubated for 1 h at room temperature. Subsequently, plates were washed again five times like above and 20 µl of an anti-T7 monoclonal antibody-HRP-conjugate, diluted 1:1000 in PBST, was added to each well and incubated for 1 hour at room temperature. Plates were again washed five times and 20 µl of the fluorogenic HRP-substrate QUANT-ABLU™ (Fluorogenic peroxidase substrate used for peroxidase detection) (diluted as described by the manufacturer) was added to detect bound BBP muteins by means of the attached anti-T7 monoclonal antibody-HRP-conjugate. After 10 minutes at room temperature fluorescence was excited at a wavelength of 320 nm (±12.5 nm) and measured at 430 nm (±17.5 nm) in a GENiosPlus plate reader.

The curve was fitted by non-linear least squares regression with the help of the computer program Kaleidagraph (Synergy software) according to the equation $[P \cdot L]=([P]_t[L]_t)/(K_D+[P]_t)$. Thereby $[P]_t$ is the total concentration of immobilized target (in relative fluorescence units), $[L]_t$ is the concentration of the applied BBP mutein, respectively, $[P \cdot L]$ is the concentration of the formed complex (in relative fluorescence units, rFU), and $K_D$ is the apparent dissociation constant.

Figure 6:
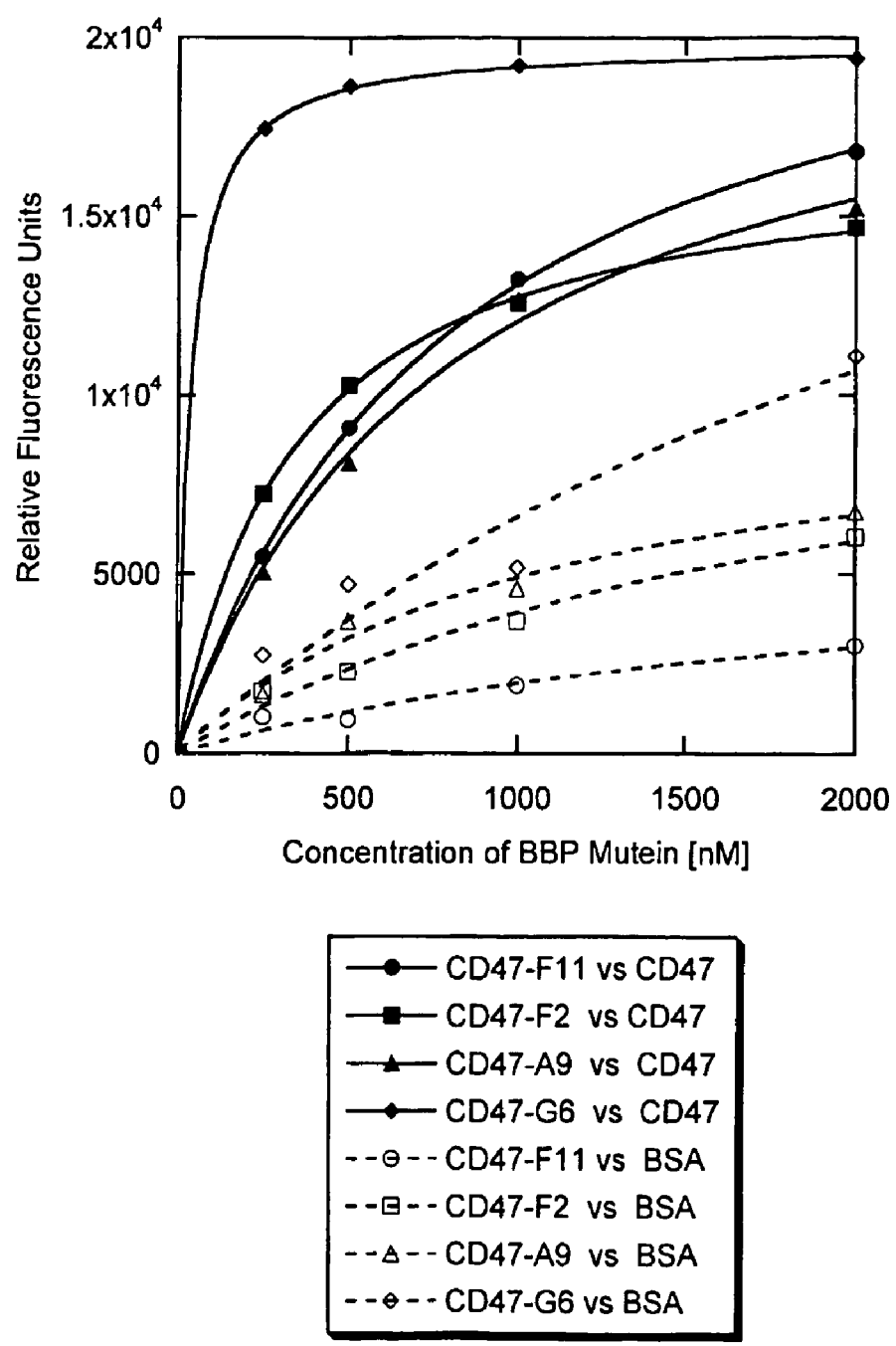
FIG. 6 depicts the binding of BBP muteins CD47-F11, CD47-F2, CD47-A9 and CD47-G6 to CD47 in an ELISA.

The resulting binding curves are depicted in FIG. 6. The values obtained for the apparent dissociation constants of the complexes between the BBP muteins and the prescribed target protein CD47 as well as for the complexes between the BBP muteins and the control protein BSA are summarized in Table 3.

TABLE 3

Affinity binding constants between the BBP muteins and CD47

| BBP mutein | $K_D$ [nM] CD47 | $K_D$ [nM] BSA |
|---|---|---|
| CD47-F11 | 806 ± 30.6 | 2265 ± 1715 |
| CD47-F2 | 339 ± 17.2 | 2058 ± 831 |
| CD47-A9 | 789 ± 127 | 1115 ± 399 |
| CD47-G6 | 33 ± 1.9 | —* |

*No measurable binding activity

Example 9

Selection of BBP Muteins Against Ferritin Employing Polystyrol Multiwell Plates

A 2 ml aliquot of the stored phagemids from Example 1 containing $10^{13}$ phagemids was centrifuged (20 minutes, 21460 g, 4° C.), the supernatant was removed, and the sedimented phagemid particles were dissolved in 2 ml PBS. After incubation for 30 minutes on ice the solution was centrifuged (5 minutes, 21460 g, 4° C.) to remove residual aggregates. The supernatant (ca. $5·10^{12}$ cfu/ml) was transferred to a new reaction vessel and was directly used for affinity enrichment.

High binding polystyrol microtiter plates (Greiner) were used for the affinity enrichment of the recombinant phagemids carrying the BBP mutein fusion proteins. Five wells were coated overnight at 4° C. with each 300 µl of type I horse ferritin (Sigma) at a concentration of 100 µg/ml in PBS.

Unoccupied binding sites on the surface of the wells were saturated by incubation with 350 µl/well 2% w/v BSA in PBST for 2 hours at room temperature and shaking at 600 rpm on a Titramax 1000 shaker. Afterwards, the wells were briefly washed three times by incubation for 2 min with 350 µl PBST/well at room temperature and 600 rpm and subsequent removal of the buffer. Subsequently, each well was incubated with a mixture of 200 µL of the phagemid solution (ca. $1·10^{12}$ cfu per well; $5·10^{12}$ cfu in total) and of 100 µL of PBS containing 6% w/v BSA and 0.3% v/v Tween 20 for 1 hour at room temperature.

For the removal of unbound phagemids, washing was performed eight times as described above, each time with 350 µl PBST per well for 2 minutes. Adsorbed phagemids were finally eluted by a 10 minute treatment of the microtiter plate with 300 µl 0.1 M glycine/HCl pH 2.2 per respective well, followed by immediate neutralisation of the pH of each elution fraction by mixing it with 47 µl 0.5 M Tris.

For the amplification, the combined phagemid solution (containing between $10^5$ and $10^8$ cfu, depending on the selection cycle) was shortly warmed to 37° C., mixed with 5 ml of an exponentially growing culture of E. coli XL1-blue ($OD_{550}$=0.5), and incubated for 30 minutes at 37° C., 140 rpm. The cells infected with the phagemids were subsequently sedimented (2 minutes, 4420 g, 4° C.), resuspended in 600 µl of the culture medium, and plated out onto three LB/Amp agar plates (145 mm diameter).

After incubation for 14 hours at 32° C., the cells were scraped from the agar plates and for the repeated production and affinity enrichment of phagemid particles 25 ml of 2×YT/Amp were inoculated to an $OD_{550}$ of ca. 0.08 with an appropriate volume of this suspension and incubated at 37° C., 160 rpm until $OD_{550}$ reached 0.5.

After infection with VCS-M13 helper phage (Stratagene) at a moi of approximately 10 the culture was shaken for additional 45 minutes at 37° C., 140 rpm. Kanamycin (70 µg/ml) was subsequently added, the incubator temperature was lowered to 26° C. and, after 10 minutes, anhydrotetracycline was added at 25 µg/l (3.1 µl of a 0.2 mg/ml stock solution in DMF) in order to induce gene expression. Incubation continued for another 12-15 hours at 26° C., 140 rpm.

The cells were sedimented by centrifugation (15 minutes, 12100 g, 4° C.) and the supernatant containing the phagemid particles was sterile-filtered (0.22 µm), mixed with ¼ volume (6.3 ml) 20% w/v PEG 8000, 15% w/v NaCl, and incubated on ice for 30-60 minutes. After centrifugation (20 minutes, 18000 g, 4° C.) the precipitated phagemid particles were dissolved in 2 ml of cold BBS/E. The solution was distributed to two 1.5 ml reaction vessels and incubated on ice for 30 minutes. After centrifugation of undissolved components (5 minutes, 21460 g, 4° C.) each supernatant was transferred to a new reaction vessel.

Mixture with ¼ volume 20% w/v PEG 8000, 15% w/v NaCl and incubation for 30 to 60 minutes on ice served to reprecipitate the phagemid particles. After centrifugation (20 minutes, 21460 g, 4° C.) the supernatant was removed and the precipitated phagemid particles were dissolved and combined in a total of 1 ml PBS. After incubation for 30 minutes on ice the solution was centrifuged (5 minutes, 21460 g, 4° C.) in order to remove residual aggregates and the supernatant containing between $10^{11}$ and $5·10^{12}$ cfu/ml was directly used for the next round of affinity enrichment.

Three further selection rounds against ferritin were carried out in this way employing the preparation of amplified phagemids from the respective previous enrichment cycle with the exception that only three wells were coated with the target protein beginning with the second enrichment cycle and that as a result only ca. 1 ml of combined phagemid solution was obtained after the elution step.

Example 10

Figure 7:
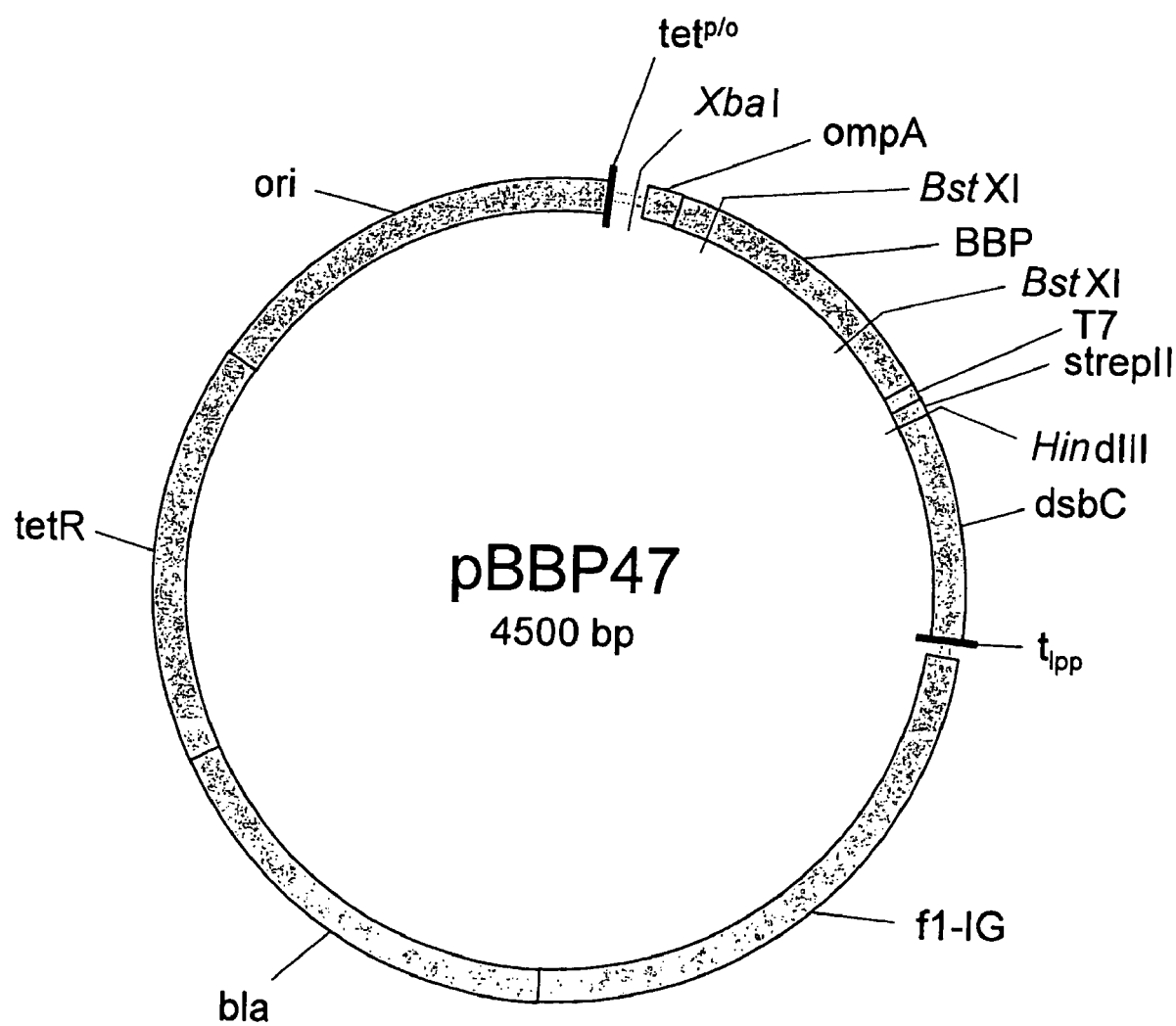
FIG. 7 schematically depicts the expression vector pBBP47.

Identification of Ferritin-Binding BBP Muteins by Use of High-Throughput ELISA Screening For the analytical production of the BBP muteins as fusion proteins with a C-terminal twin tag construction consisting of a T7-tag (Novagene) followed by a STREP-TAG® II and their characterization by high-throughput ELISA screening, the gene cassette between the two BstXI cleavage sites was subcloned from the vector pBBP38 on pBBP47 (FIG. 7).

For this purpose the plasmid DNA was isolated from the mixture of the E. coli clones obtained by infection with the phagemids from Example 9 which were eluted as a result of the last selection cycle, using the Plasmid Miniprep Spin kit (Genomed). The DNA was cut with the restriction enzyme BstXI and the smaller of the two fragments (335 bp) was purified by preparative agarose-gel electrophoresis as described in Example 1. The DNA of the vector pBBP47 was cut with BstXI and the larger of the two fragments (4165 bp) was isolated in the same way. 50 fmol of both fragments were used in a ligation reaction and subsequent transformation of E. coli TG1-F⁻ as described in Example 4.

Single E. coli colonies obtained after the transformation harbouring the pBBP47 plasmids coding for the BBP muteins were picked from LB/Amp agar plates (22 cm×22 cm) into 70 µl 2×YT/Amp per well in flat bottom 384 well plates (Greiner) by means of an automated colony picker and used for the production of recombinant BBP muteins as described in Example 4. To minimize non-specific binding interactions in the subsequent ELISA experiment, obtained crude cell extracts were supplemented with 40 µl/well PBS containing 10% w/v BSA and 0.05% v/v Tween 20 (final concentration 2% BSA) for 1 h at 22° C. and 700 rpm at 60% rH.

For the detection of binding, these cell extracts were tested for their reactivity on the prescribed target type I horse ferritin as well as the unrelated control protein aldolase in ELISA experiments. Therefore, wells of black Fluotrac 600 ELISA plates (Greiner; 384 well) were coated overnight with 20 µl of a solution of ferritin (Sigma) or aldolase (Roche) at 4° C., each at a concentration of 20 µg/ml in PBS. Plates were washed five times with 100 µl PBST/0.05 per well with an automated ELISA plate washer (Molecular Devices) leaving a residual volume of 10 µl of the washing buffer in each well after the last washing step. Residual binding sites were blocked by incubation with 100 µl PBST/0.05 containing 2% w/v BSA for 2 h at room temperature. Afterwards, plates were again washed five times as described above.

For complex formation between the BBP muteins and the immobilized proteins, the wells were incubated with 10 µl of the blocked cell extract from above for 1 hour at room temperature. Subsequently, plates were washed again five times and 10 µl of an anti-T7 monoclonal antibody-HRP-conjugate (Amersham), diluted 1:5000 in PBST/0.05 containing 0.5% w/v non-fat dry milk powder (Vitalia), was added to each well and incubated for 1 hour at room temperature. Plates were washed five times and 10 µl of the fluorogenic HRP-substrate QUANTABLU™ (Pierce, diluted as described by the manufacturer) was added to detect bound BBP muteins by means of the attached anti-T7 monoclonal antibody-HRP-conjugate. After 60 minutes at room temperature fluorescence was excited at a wavelength of 320 nm (±12.5 nm) and measured at 430 nm (±17.5 nm) in a GENiosPlus plate reader (Tecan).

14 of 368 analyzed BBP muteins showed a signal-to-control ratio of five or better compared to the control protein aldolase and were selected for more detailed binding analyses in a secondary high-throughput ELISA screening experiment. Therefore, these clones were transferred from the flat bottom 384 well plates described above onto LB/Amp agar, and grown overnight at 37° C. 100 µl 2×YT/Amp in round bottom 96 well plates (Nunc) was inoculated with single colonies from these agar plates and grown overnight at 37° C. at 700 rpm and 60% rH. The cultures were diluted 1:100 into 100 µl 2×YT/Amp again in round bottom 96 well plates (Nunc) and production of recombinant BBP muteins as well as preparation of the bacterial lysates was performed as described in Example 4.

For the detection of target-specificity of the BBP muteins, wells of black Fluotrac 600 ELISA plates (Greiner; 384 well) were coated overnight at 4° C. with 20 µl of a solution of ferritin or, as a control, with BSA, transferrin (Roche), aldolase, ovalbumin (Sigma), streptactin (IBA), human serum albumin (Sigma) as well as a conjugate of RNaseA and digoxigenin (produced as described in Example 4), each at a concentration of 20 µg/ml in PBS. Afterwards, the plates were washed and blocked as described in Example 4. 10 µl of the blocked bacterial lysates of the 14 BBP muteins described above were transferred to each of the wells coated with either ferritin or the unrelated control proteins and incubated for 1 h at ambient temperature. After washing, bound BBP muteins were detected with anti-T7 monoclonal antibody-HRP-conjugate and the fluorogenic HRP-substrate QUANTABLU™ as described in Example 4.

Eight of fourteen BBP muteins giving rise to the best signal-to-control ratios on the prescribed target ferritin versus the control proteins were selected and their nucleotide sequence of the BBP gene cassette was determined using the oligodeoxynucleotide SEQ ID NO: 14 as primer as described in Example 4. The eight sequenced clones exhibited only six different sequences, which were named Fer-N22, Fer-I21, Fer-D24, Fer-N21, Fer-P4 and Fer-O20. The nucleotide sequences of these clones were translated into the amino acid sequence and those amino acids deviating from BBP are given in Table 4. The nucleotide and amino acid sequences of Fer-N22, Fer-I21, Fer-D24, Fer-N21, Fer-P4 and Fer-O20 are also given as SEQ ID NOS: 19 (nucleotide sequence) and SEQ ID NO: 51 (amino acid sequence)., SEQ ID NOS: 20 (nucleotide sequence) and SEQ ID NO: 52 (amino acid sequence)., SEQ ID NOS: 21 (nucleotide sequence) and SEQ ID NO: 53 (amino acid sequence)., SEQ ID NOS: 22 (nucleotide sequence) and SEQ ID NO: 54 (amino acid sequence)., SEQ ID NOS: 23 (nucleotide sequence) and SEQ ID NO: 55 (amino acid sequence), and SEQ ID NOS: 24 (nucleotide sequence) and SEQ ID NO: 56 (amino acid sequence)., respectively.

TABLE 4

Sequence characteristics of selected anti-Ferritin muteins

| Pos. | BBP | Fer-N22 | Fer-I21 | Fer-D24 | Fer-N21 | Fer-P4 | Fer-O20 |
|---|---|---|---|---|---|---|---|
| 32° | Tyr | Tyr | Tyr | Tyr | Tyr | Tyr | Cys |
| 34° | Asn | Asn | Asn | Ser | Ser | Ser | Ser |
| 35 | Ser | Gly | Gln | Lys | Asn | Lys | Gly |
| 36 | Val | Gly | Lys | Lys | Arg | Gly | Lys |
| 37° | Glu | Glu | Glu | Gly | Gly | Gly | Gly |
| 38 | Lys | Ser | Lys | Lys | Ser | Glu | Arg |
| 39 | Tyr | Pro | Trp | Gln | Lys | Lys | Ala |
| 58° | Asn | Asn | Asn | Arg | Arg | Arg | Arg |
| 60° | His | His | His | Asp | Asp | Asp | Asp |
| 63 | His | Lys | Lys | Pro | Pro | Leu | Pro |
| 64 | Gly | Lys | Arg | Cys | Arg | Ser | Ala |
| 65 | Lys | Arg | Pro | Leu | Leu | Ser | Pro |
| 67 | Tyr | Arg | Arg | Ser | Ala | Pro | Leu |
| 69° | Ile | Ile | Ile | Met | Met | Met | Met |
| 79° | Ser | Ser | Ser | Ser | Ser | Ser | Pro |
| 85° | Tyr | Cys | Tyr | Tyr | Tyr | Tyr | Tyr |
| 88° | Leu | Leu | Leu | Arg | Arg | Arg | Arg |
| 90 | Tyr | Trp | Arg | Lys | Ser | Lys | Asn |
| 91 | Gly | Ser | Leu | Pro | Lys | Lys | Lys |
| 93 | Val | Leu | Lys | Arg | Lys | Glu | Leu |
| 96° | Glu | Glu | Glu | Lys | Lys | Lys | Lys |
| 97° | Asn | Asn | Asn | Thr | Thr | Thr | Thr |
| 102° | Leu | Leu | Leu | Pro | Leu | Leu | Leu |
| 116 | Lys | Lys | Leu | Val | Ile | Gly | Lys |
| 118 | Asp | Lys | Pro | Pro | Asn | Cys | Gly |
| 120 | Asp | Arg | Gly | Gly | Arg | Cys | Asp |
| 121 | Lys | Lys | Trp | Arg | Tyr | Arg | Gln |
| 125 | Gln | Gly | Lys | Arg | Tyr | Ala | Lys |
| 127° | Phe | Phe | Phe | His | His | His | His |

°These amino acid substitutions arose from accidental mutations outside the randomized positions.

Example 11

Production of the BBP Muteins

Single colonies of *E. coli*-TG1F⁻ transformed with the pBBP47 plasmids coding either for the BBP muteins Fer-N22, Fer-I21, Fer-D24, Fer-N21, Fer-P4 and Fer-O20 instead of wildtype BBP obtained from Example 10 were used for preparative production of the recombinant proteins according to Example 7. The protein yield for each of the BBP muteins was approximately 30-100 µg per 1 l culture.

Example 12

Measurement of the Affinity of the BBP Muteins for Ferritin in ELISA

For the determination of binding affinity of the selected BBP muteins from Example 11 for the prescribed protein target ferritin as well as the unrelated control proteins transferrin and RNaseB (Sigma) in an ELISA the wells of black Fluotrac 600 ELISA plates (Greiner; 384 well) were coated with 20 μl of a 50 μg/ml solution of the respective protein in PBS for one hour at room temperature. Afterwards, the wells were washed and blocked as described in Example 8.

Then, a dilution series of the BBP muteins from Example 11 in SA-buffer was prepared in PBST starting from 1000 nM concentration and incubated for 1 h at room temperature. Subsequently, plates were washed again five times, anti-T7 monoclonal antibody-HRP-conjugate was added and incubated for 1 hour at room temperature followed by washing and addition of fluorogenic HRP-substrate QUANTABLU™ as described in Example 8. After 10 minutes at room temperature fluorescence was excited at a wavelength of 320 nm (±12.5 nm) and measured at 430 nm (±17.5 nm) in a GENios-Plus plate reader.

Figure 8:
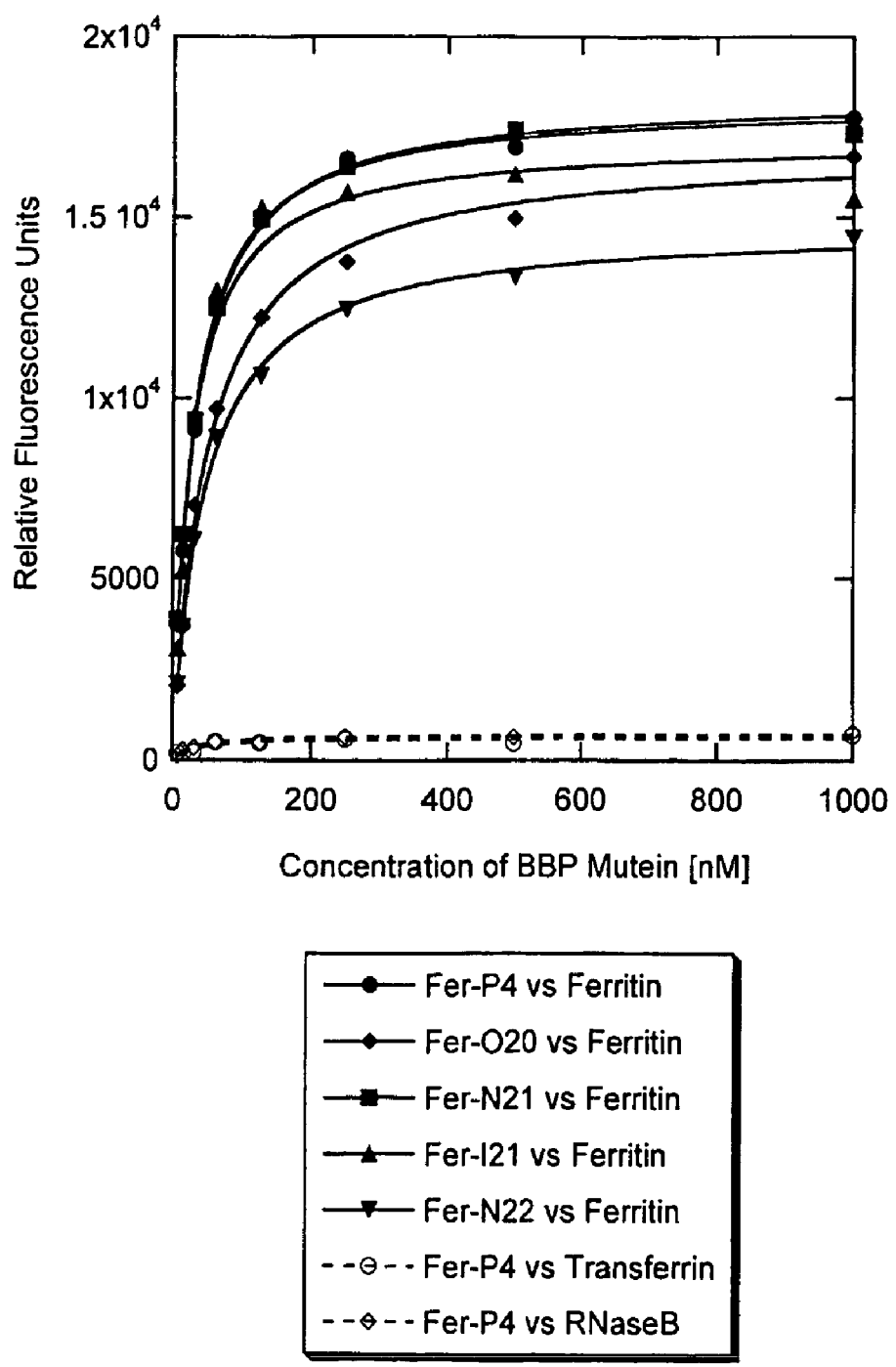
FIG. 8 depicts the binding of BBP muteins Fer-N22, Fer-I21, Fer-N21, Fer-P4 and Fer-O20 to ferritin in an ELISA.

The resulting binding curves were fitted by non-linear least squares regression as described in Example 8 and are depicted in FIG. 8. The values obtained for the apparent dissociation constants of the complexes between the BBP muteins and the prescribed target ferritin are summarized in Table 5.

TABLE 5

Affinity binding constants between the BBP muteins and ferritin

| BBP mutein | $K_D$[nM]ferritin | $K_D$[nM]transferrin | $K_D$[nM] RNaseB |
|---|---|---|---|
| Fer-P4 | 31 ± 3.5 | —* | —* |
| Fer-O20 | 49 ± 3.8 | —* | —* |
| Fer-N21 | 29 ± 0.9 | —* | —* |
| Fer-I21 | 26 ± 4.0 | —* | —* |
| Fer-N22 | 45 ± 2.0 | —* | —* |

*No detectable binding activity

Example 13

Figure 1:
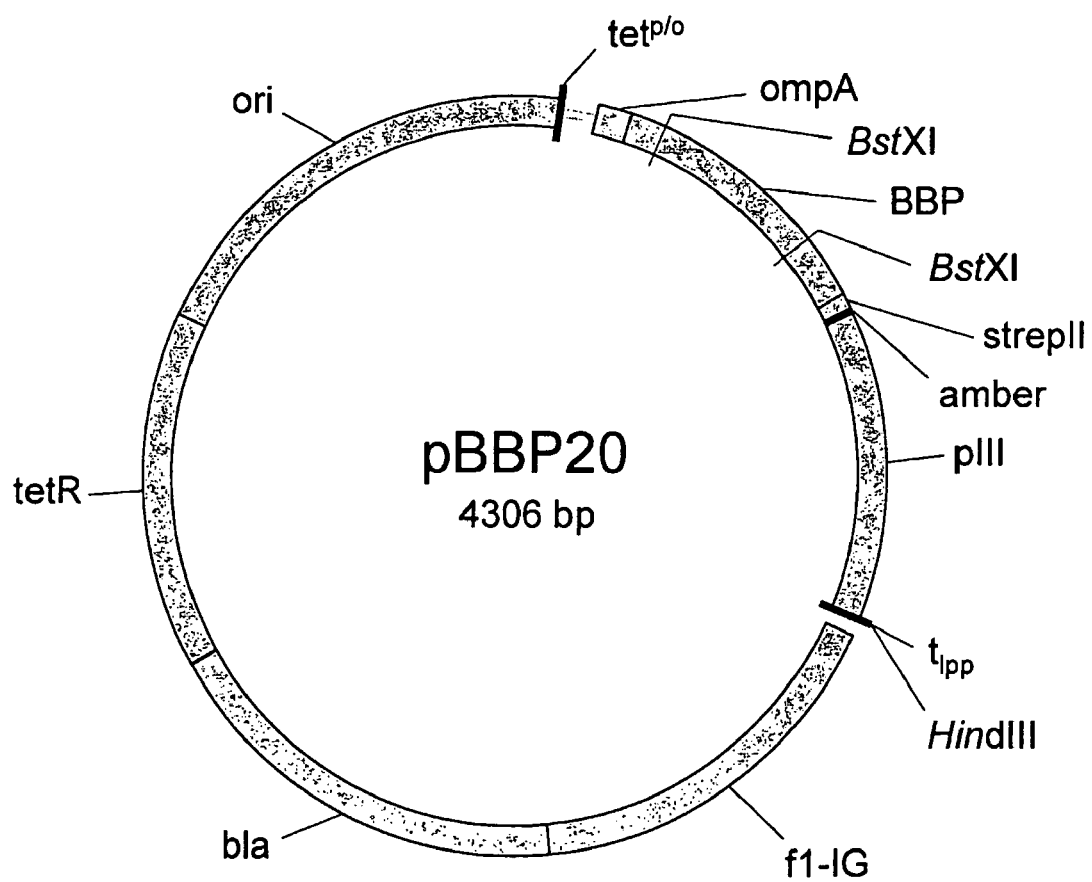
FIG. 1 schematically depicts the phasmid vector pBBP20.

Preparation of a Library with 10 Billion Independent BBP Muteins with N-Terminal T7-Tag A random library with high diversity consisting of BBP muteins equipped with an N-terminal T7 tag was prepared by concerted mutagenesis of in total 16 selected amino acid positions in the four peptide loops using PCR in multiple steps according to FIG. 3. The PCR reactions were carried out in a volume of 100 μl in both of the first amplification steps, wherein 10 ng pBBP20 (FIG. 1) plasmid DNA was employed as template together with 50 pmol of each pair of primers (SEQ ID NO: 2 and SEQ ID NO: 3 or SEQ ID NO: 4, and SEQ ID NO: 5, respectively), which had been synthesized according to the conventional phosphoramidite method. In addition, the reaction mixture contained 10 μl 10× Taq buffer (100 mM Tris/HCl pH 9.0, 500 mM KCl, 15 mM MgCl$_2$, 1% v/v Triton X-100) and 2 μl dNTP-Mix (10 mM dATP, dCTP, dGTP, dTTP). After bringing to volume with water, 5 u Taq DNA-polymerase (5 u/μl, Promega) were added and 20 temperature cycles of 1 minute at 94° C., 1 minute at 60° C. and 1.5 minutes at 72° C. were carried out in a thermocycler with a heated lid (Eppendorf), followed by an incubation for 5 minutes at 60° C. for final extension. The desired amplification products were isolated by preparative agarose gel electrophoresis from GTQ Agarose (Roth) using the Jetsorb DNA extraction kit (Genomed).

For the subsequent amplification step a 2000 μl mixture was prepared, wherein approximately 1000 fmol of both of these respective fragments were used as templates, in the presence of 1000 pmol of each of the assembly primers SEQ ID NO: 7, SEQ ID NO: 8 and 20 pmol of the mediating primer SEQ ID NO: 6. Both assembly primers carried a biotin group at their 5'-end, allowing subsequent purification of the PCR-product after BstXI cleavage via streptavidin-coated paramagnetic beads. Additionally 200 μl 10× Taq buffer, 40 μl dNTP-Mix (10 mM dATP, dCTP, dGTP, dTTP), 100 u Taq DNA-polymerase (5 u/μl, Promega) and 1525 μl of water were added to bring the mixture to the final volume of 2000 μl. The mixture was divided into 100 μl aliquots and PCR was performed with 20 temperature cycles of 1 minutes at 94° C., 1 minute at 60° C., 1.5 minutes at 72° C., followed by a subsequent incubation for 5 minutes at 60° C. The PCR product was purified using the E.Z.N.A. Cycle-Pure Kit (PeqLab).

For the cloning of this fragment, which represented the library of the N-terminally tagged BBP muteins in nucleic acid form, it was first cut with the restriction enzyme BstXI (Promega) according to the instructions of the manufacturer and purified by preparative agarose gel electrophoresis like described above, resulting in a double stranded DNA-fragment of 335 nucleotides in size. Residual DNA-fragments which were not or incompletely digested were removed via their 5'-biotin tags by incubating their solution with streptavidin-coated paramagnetic beads (Merck), thus obtaining the doubly cut DNA fragment suitable for the subsequent ligation reaction.

To this end, 200 μl of the commercially available suspension of the paramagnetic particles in a concentration of 10 mg/ml were washed three times with 100 μl TE-buffer. The paramagnetic particles were then drained and mixed with 100 pmol of the DNA-fragment in 100 μl TE-buffer for 15 minutes at room temperature. The paramagnetic particles were collected at the wall of the Eppendorf vessel with the aid of a magnet and the supernatant containing the purified DNA fragment was recovered for further use in the following ligation reaction.

Figure 9:
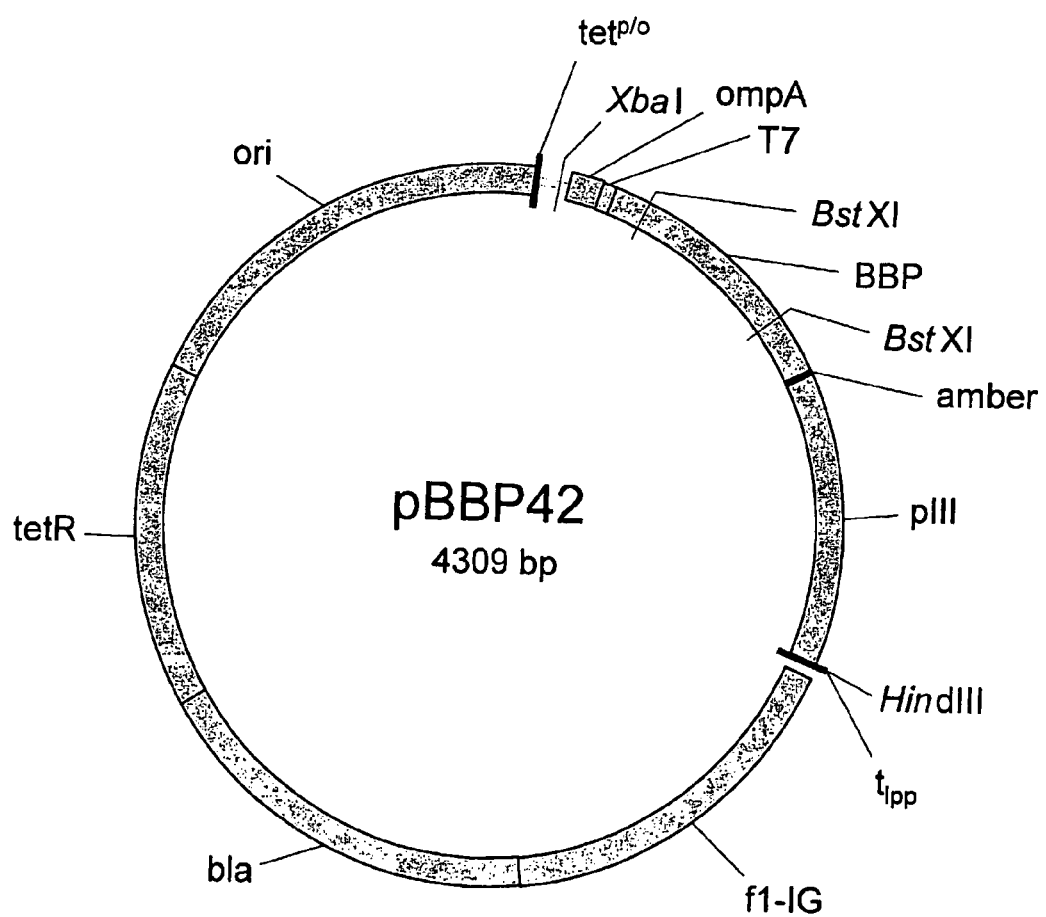
FIG. 9 schematically depicts the phasmid vector pBBP42.

The DNA of the vector pBBP42 (FIG. 9) was cut with BstXI as described above and the larger of the two resulting fragments (3974 bp) was isolated by preparative agarose gel electrophoresis. For the ligation, 6.85 μg (31 pmol) of the PCR fragment and 81.3 μg (31 pmol) of the vector fragment were incubated in the presence of 891 Weiss Units of T4 DNA ligase (Promega) in a total volume of 8920 μl (50 mM Tris/HCl pH 7.8, 10 mM MgCl$_2$, 10 mM DTT, 1 mM ATP, 50 μg/ml BSA) for 48 h at 16° C. The DNA in the ligation mixture was then precipitated by adding 223 μl tRNA (yeast) of a 10 mg/ml solution in H$_2$O (Roche), 8900 μl 5 M ammonium acetate, and 36 ml ethanol. Incubation at room temperature for 1 h was followed by centrifugation (30 minutes, 16000 g, 4° C.). The precipitate was washed with 12 ml ethanol (70% v/v, room temperature), centrifuged (10 minutes, 16000 g, 4° C.), and air dried until the DNA pellet appeared glossy and uncoloured. The DNA was finally dissolved in a total volume of 446 μl water to a final concentration of 200 μg/ml.

The preparation of electrocompetent cells of the *E. coli* K12 strain XL1-blue (Bullock et al., supra) was carried out as described in Example 1. The Micro Pulser system (BioRad) was used in conjunction with the cuvettes from the same vendor (electrode separation 2 mm) for the electroporation. All steps were carried out at room temperature employing pre-chilled cuvettes at a temperature of −20° C. Each 10 μl of the DNA solution (2 μg) from above was mixed with 100 μl of the cell suspension, incubated for 1 minute on ice, and transferred to the pre-chilled cuvette. Then the electroporation was performed (5 ms, 12.5 kV/cm) and the suspension was immediately diluted in 2 ml of SOC-medium followed by shaking for 60 minutes at 37° C. and 140 rpm. Afterwards, the culture was diluted in 5 l 2×YT-medium containing 100 µg/ml ampicillin (2YT/Amp) resulting in an $OD_{550}$ of 0.09. By employing in total 88.15 µg of the ligated DNA, $1.5 \cdot 10^{10}$ transformants were obtained in this manner using altogether 42 electroporation runs.

The culture containing the cells which were transformed with the phasmid vectors corresponding to pBBP42, but coding for the library of the BBP muteins as fusion proteins, was incubated at 37° C. and 140 rpm until the $OD_{550}$ caused by the replicating cells was raised to ca. 0.7. 3 l of this culture was transferred to a sterile Erlenmeyer flask and infected with VCS-M13 helperphage (Stratagene) at a multiplicity of infection (moi) of approximately 10 and the culture was shaken for additional 45 minutes at 37° C. at 100 rpm. Then the incubator temperature was lowered to 26° C. and 2 ml of a 35 mg/ml stock solution of kanamycin was added per liter of culture to reach a final concentration of 70 µg/ml. After 10 minutes, anhydrotetracycline (ACROS Organics) was added at 25 µg/l (37.5 µl of a 200 µg/ml stock solution in dimethylformamide, DMF) in order to induce gene expression. Incubation continued for another 11 hours at 26° C., 160 rpm.

The cells were sedimented by centrifugation (30 minutes, 18000 g, 4° C.) and the supernatant containing the phagemid particles was sterile-filtered (0.45 µm). Afterwards, the culture was mixed with ¼ volume (375 ml) ice-cold 20% w/v PEG 8000, 15% w/v NaCl and incubated on ice for two hours. After centrifugation (30 min, 18000 g, 4° C.) the precipitated phagemid particles were dissolved in 60 ml of ice cold BBS/E (20 mM borate pH 8.0, 160 mM NaCl, 1 mM EDTA) containing 50 mM benzamidine (Sigma). The solution was incubated on ice for 60 minutes and was distributed into two SS34 centrifugation tubes. After centrifugation of undissolved components (10 min, 18000 g, 4° C.) the supernatants were transferred to a new centrifugation tube. The phagemid particles were reprecipitated by mixing with ¼ volume 20% w/v PEG 8000, 15% w/v NaCl and incubation for 60 minutes on ice, divided in aliquots of 2 ml with a titer of ca. $4 \cdot 10^{12}$ colony forming units (cfu) per ml, and stored at −80° C.

Example 14

Selection of BBP Muteins Against the Extracellular Domain of Human CD154 Employing Polystyrol Multiwell Plates A 2 ml aliquot of the precipitated phagemids from Example 13 was centrifuged (20 minutes, 21460 g, 4° C.), the supernatant was removed, and the sedimented phagemid particles were dissolved in 750 µl PBS containing 50 mM benzamidine. After incubation for 30 minutes on ice the solution was centrifuged (5 minutes, 21460 g, 4° C.) to remove residual aggregates and for blocking of non-specific binding sites on the phagemid surface the supernatant was mixed with the same volume PBST containing 5% w/v skimmed milk powder (Marvel) and incubated at room temperature for 30 min.

High binding polystyrol microtiter plates (Greiner) were used for the affinity enrichment of the recombinant phagemids carrying the BBP mutein fusion proteins. Five wells were coated overnight at 4° C. with each 300 µl of the extracellular domain of human CD154 (DPC Biermann) at a concentration of 50 µg/ml in PBS. Unoccupied binding sites on the surface of the wells were saturated by incubation with 350 µl per well 5% w/v skimmed milk powder in PBS for 2 hours at room temperature under shaking at 600 rpm on a Titramax 1000 shaker (Heidolph) followed by three brief washes by incubation with 350 µl PBST per well for 2 min at room temperature, 600 rpm and subsequent removal of the buffer. Afterwards, each well was incubated with 300 µl of the blocked phagemid solution from above (ca. $1.6 \cdot 10^{12}$ cfu per well; $8 \cdot 10^{12}$ cfu in total) for 2 hours at room temperature.

For the removal of unbound phagemids, washing was performed eight times as described above, each time with 350 µl PBST per well for 2 minutes. Adsorbed phagemids were finally eluted by a 10 minute treatment of the microtiter plate with 300 µl 0.1 M glycine/HCl pH 2.2 per respective well, followed by immediate neutralisation of the pH of each elution fraction by mixing it with 47 µl 0.5 M Tris.

For the amplification, the combined phagemid solution (containing between $10^5$ and $10^8$ cfu, depending on the selection cycle) was shortly warmed to 37° C., mixed with 5 ml of an exponentially growing culture of E. coli XL1-blue ($OD_{550}$=0.5), and incubated for 30 minutes at 37° C., 140 rpm. The cells infected with the phagemids were subsequently sedimented (2 minutes, 4420 g, 4° C.), resuspended in 600 µl of the culture medium, and plated out onto three LB/Amp agar plates (145 mm diameter).

After incubation for 14 hours at 32° C., the cells were scraped from the agar plates and for the repeated production and affinity enrichment of phagemid particles 25 ml of 2×YT/Amp were inoculated to an $OD_{550}$ of ca. 0.08 with an appropriate volume of this suspension and incubated at 37° C., 160 rpm until $OD_{550}$ reached 0.5.

After infection with VCS-M13 helper phage (Stratagene) at a moi of approximately 10 the culture was shaken for additional 45 minutes at 37° C., 140 rpm. Kanamycin (70 µl/ml) was subsequently added, the incubator temperature was lowered to 26° C. and, after 10 minutes, anhydrotetracycline was added at 25 µg/l (3.1 µl of a 0.2 mg/ml stock solution in DMF) in order to induce gene expression. Incubation continued for another 12-15 hours at 26° C., 140 rpm.

The cells were sedimented by centrifugation (15 minutes, 12100 g, 4° C.) and the supernatant containing the phagemid particles was sterile-filtered (0.45 µm), mixed with ¼ volume (6.3 ml) 20% w/v PEG 8000, 15% w/v NaCl, and incubated on ice for 30-60 minutes. After centrifugation (20 minutes, 18000 g, 4° C.) the precipitated phagemid particles were dissolved in 2 ml of cold BBS/E. The solution was distributed to two 1.5 ml reaction vessels and incubated on ice for 30 minutes. After centrifugation of undissolved components (5 minutes, 21460 g, 4° C.) each supernatant was transferred to a new reaction vessel.

Mixture with ¼ volume 20% w/v PEG 8000, 15% w/v NaCl and incubation for 30 to 60 minutes on ice served to reprecipitate the phagemid particles. After centrifugation (20 minutes, 21460 g, 4° C.) the supernatant was removed and the precipitated phagemid particles were dissolved and combined in a total of 1 ml PBS containing 50 mM benzamidine. After incubation for 30 minutes on ice the solution was centrifuged (5 minutes, 21460 g, 4° C.) in order to remove residual aggregates. For blocking of non-specific binding sites on the phagemid surface the supernatant was subsequently mixed with 1 ml PBST containing 5% w/v skimmed milk powder (Marvel) and incubated for 30 minutes at room temperature prior to utilization in the subsequent selection round.

Three further selection cycles against CD154 were carried out in this way employing the amplified and blocked phagemids from the respective previous enrichment cycle containing between $5 \cdot 10^{10}$ and $2 \cdot 10^{12}$ cfu/ml with the exception that beginning with the second enrichment cycle only three wells of a high binding microtiter plate were coated with CD154 and that incubation of the phagemids with the immobilized target protein was allowed for 1 h instead of 2 h at ambient temperature.

Example 15

Figure 10:
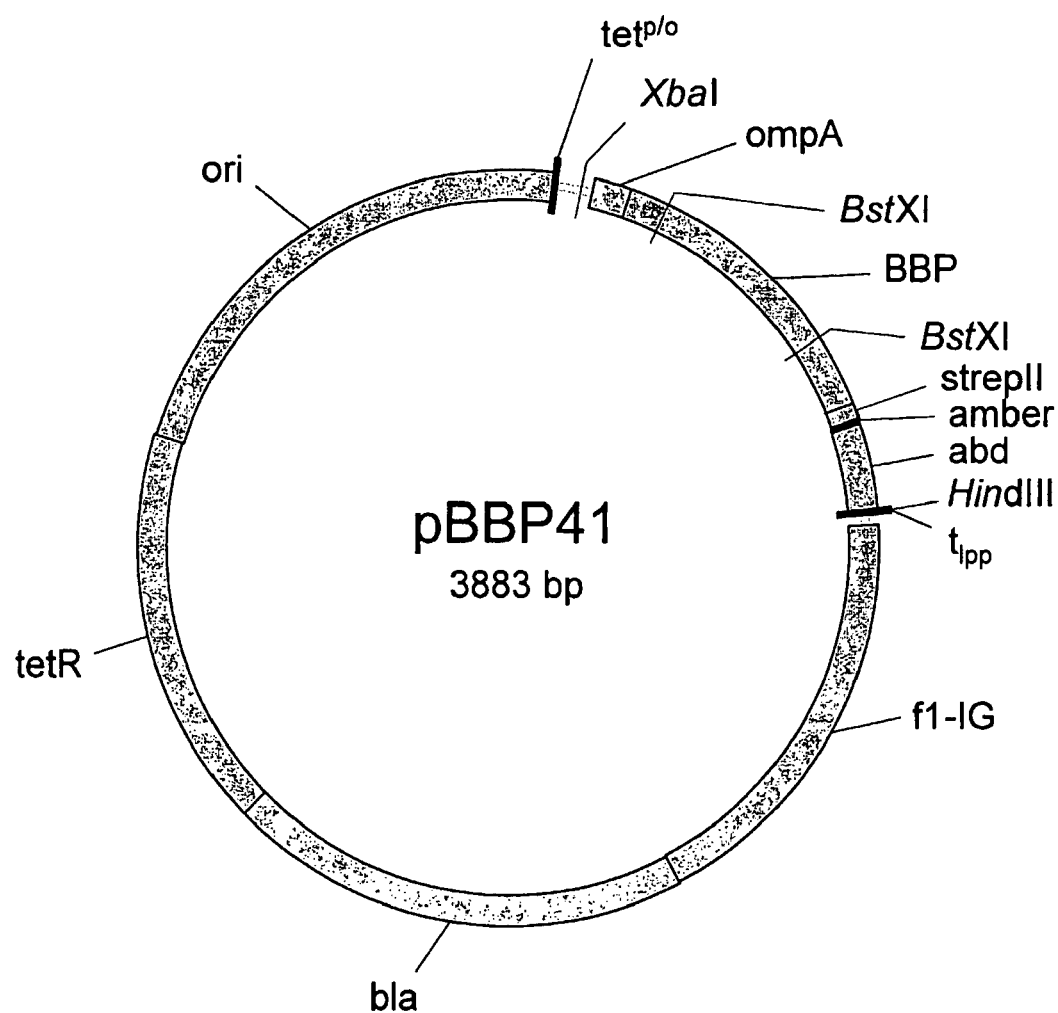
FIG. 10 schematically depicts the phasmid vector pBBP41.
Figure 11:
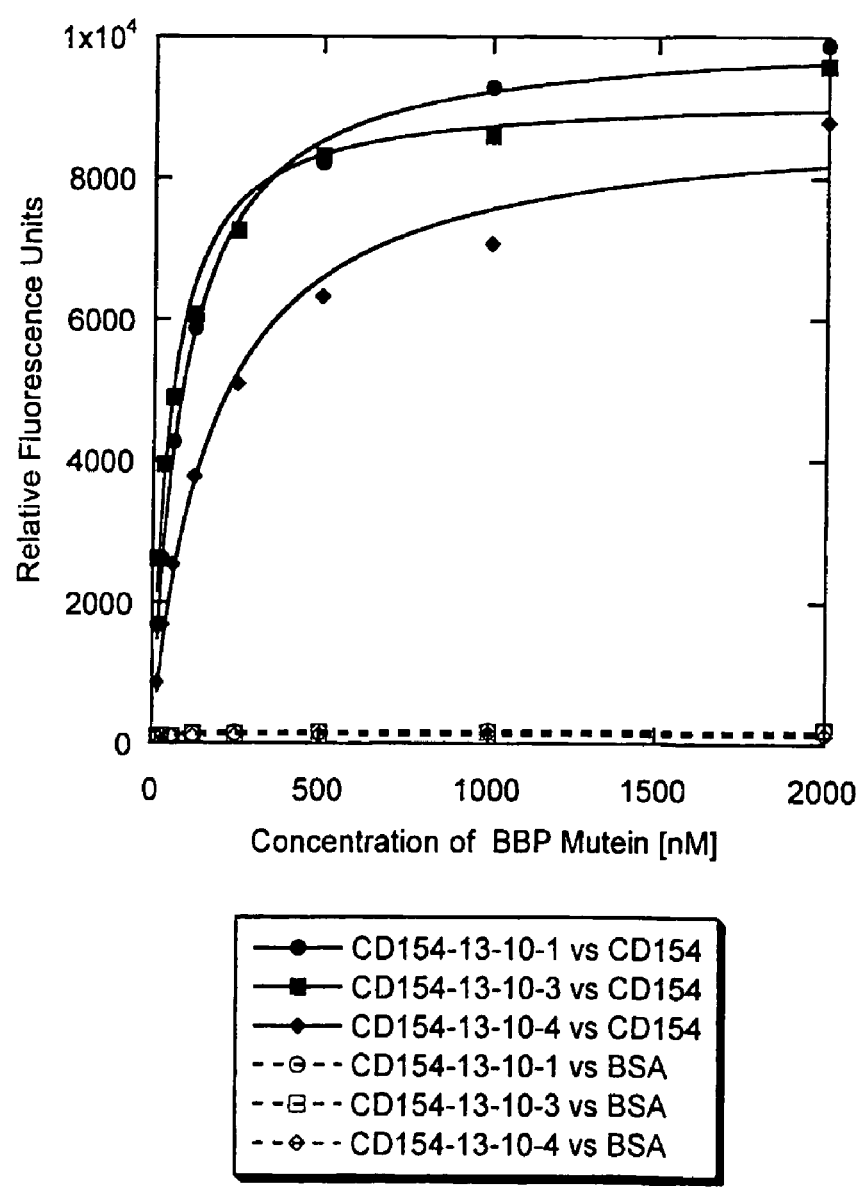
FIG. 11 depicts the binding of BBP muteins CD154-13-10-1, CD154-13-10-3, CD154-13-10-4 to CD154 in an ELISA.
Figure 12:
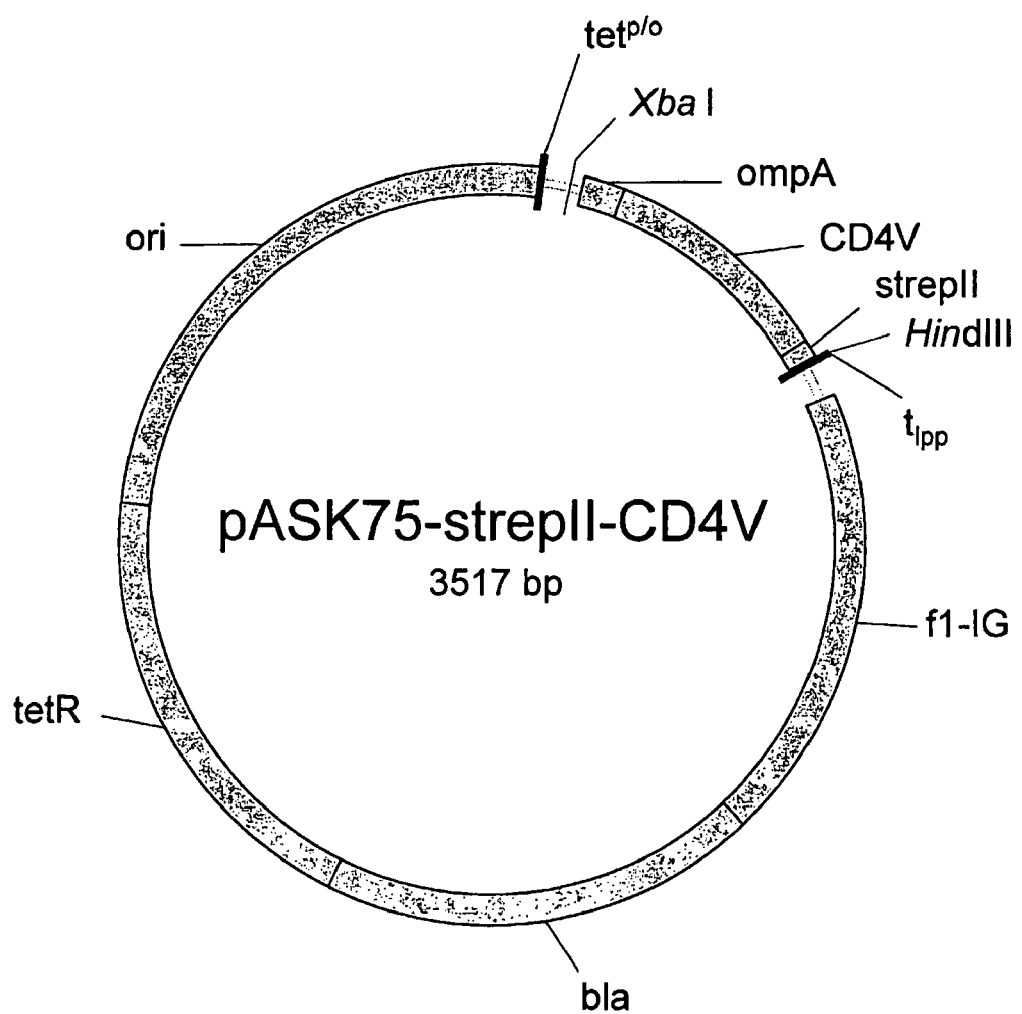
FIG. 12 schematically depicts the expression vectors (a) pASK75-strepII-CD4V, (b) pASK75-strepII-CD4D1 and Cc) pASK75-strepII-CD4VD1.
Figure 12:
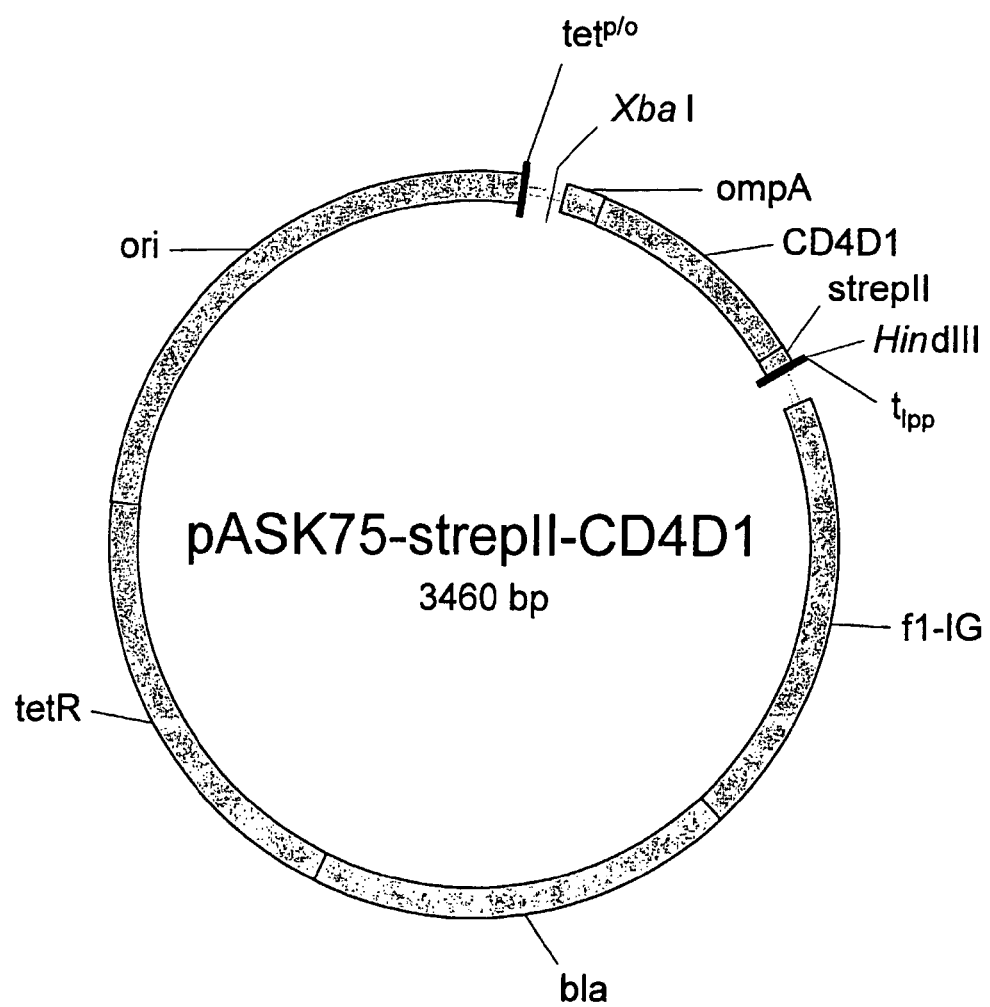
Figure 12:
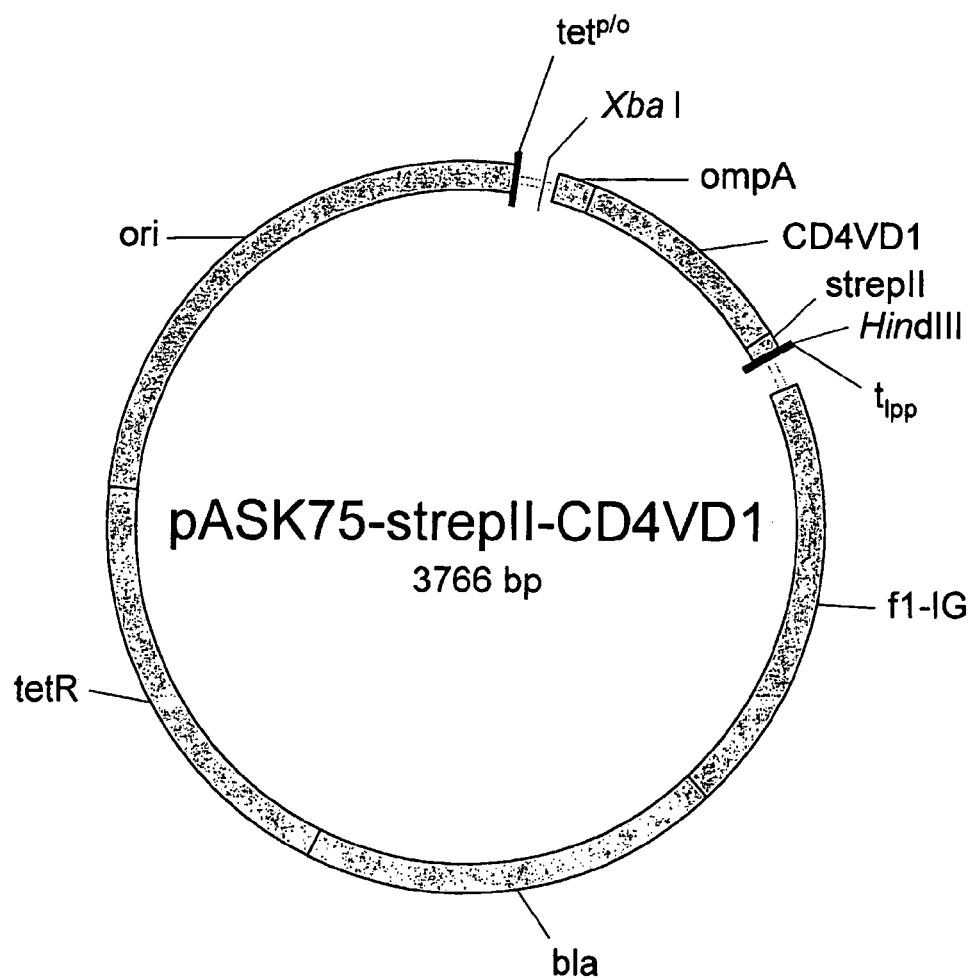

Identification of CD154-Binding BBP Muteins by Use of the Colony Screening Method For the analytical production of the BBP muteins as fusion proteins with the STREP-TAG® II and the albumin-binding domain (ABD) and their characterization by colony screening, the gene cassette between the two BstXI cleavage sites was subcloned from the phagemid vector pBBP42 on pBBP41 (FIG. 10).

For this purpose the phasmid DNA was isolated from the mixture of the E. coli clones obtained by infection with the phagemids from Example 14, eluted after the fourth selection cycle, using the Plasmid Miniprep Spin kit (Genomed). The DNA was cut with the restriction enzyme BstXI and the smaller of the two fragments (335 bp) was purified by preparative agarose gel electrophoresis as described in Example 1. The DNA of the vector pBBP41 was likewise cut with BstXI and the larger one of the two fragments (3548 bp) was isolated in the same way.

For the ligation, 50 fmol of the isolated small DNA-fragment was mixed with 50 fmol of the large DNA-fragment and incubated with 3 Weiss Units of T4 DNA ligase (Promega) in a total volume of 20 µl (30 mM Tris/HCl pH 7.8, 10 mM MgCl$_2$, 10 mM DTT, 1 mM ATP), followed by incubation overnight at 16° C. E. coli TG1-F$^-$ was transformed with 4 µl of this ligation mixture according to the CaCl$_2$-method, yielding 1.0 ml of a cell suspension which was subsequently stored at −80° C. after adding ¼ volume 80% v/v glycerol.

A hydrophilic PVDF membrane (Millipore, type GVWP, pore size 0.22 µm), labelled at one position and cut to size, was laid onto an LB/Amp agar plate. An appropriate volume of the glycerol stock of the transformation batch described above was uniformly plated onto this membrane in order to yield ca. 400-500 transformants. The agar plate was incubated for 7.5 hours at 37° C. until the colonies had reached a size of approximately 0.5 mm.

In the meantime, a hydrophobic membrane (Millipore, Immobilon P, pore size 0.45 µm), also cut to size, was moistened with water according to the instructions of the manufacturer. It was subsequently agitated for 4 hours at room temperature in 10 ml of a solution of 10 mg/ml human serum albumin (HSA, Sigma) in PBS. Remaining binding sites on the membrane were saturated by incubation with 15 ml PBST/0.05 containing 3% w/v BSA for 2 hours at room temperature. The membrane was washed twice for 10 minutes with 20 ml PBS and immersed afterwards for 10 minutes in 10 ml LB/Amp medium, to which 200 µg/l anhydrotetracycline was added. It was subsequently marked at one position and laid onto a culture plate with LB/Amp agar, which additionally contained 200 µg/l anhydrotetracycline. The hydrophilic membrane from above, on which the colonies were grown, was laid onto the hydrophobic membrane in such a way that both marks superimposed. The culture plate was incubated with the stack of both membranes at 22° C. for 15 hours. During this phase the respective BBP muteins were secreted from the colonies on the upper membrane and were immobilized via their albumin-binding domain on the HSA at the lower membrane.

After this, the upper membrane with the colonies was transferred to a fresh LB/Amp agar plate and stored at 4° C. The hydrophobic membrane was removed and washed three times for 5 minutes each with 20 ml PBST. For analysis of the binding activity of the immobilized BBP muteins, the hydrophobic membrane was incubated for 1 hour in 5 ml of a solution of a conjugate (100 nM) of CD154 and digoxigenin in PBS. The conjugate was prepared by reacting CD154 (DPC Biermann) at a twofold molar ratio of DIG-NHS (Roche) according to the instructions of the manufacturer. Excess reactant was removed from the CD154-conjugate by means of size exclusion chromatography as described in Example 4.

After incubation with the conjugate, the membrane was washed three times with PBST, followed by incubation for 1 hour with 5 ml anti-digoxigenin Fab-alkaline-phosphatase conjugate (Roche) diluted 1:1000 in PBST to detect bound CD154 by means of the attached digoxigenin groups. The membrane was washed twice with PBST and twice with PBS, each for 5 minutes, and agitated for 10 minutes in AP-buffer (0.1 M Tris/HCl pH 8.8, 0.1 M NaCl, 5 mM MgCl$_2$). For the chromogenic reaction, the membrane was incubated in 10 ml AP-buffer, to which 30 µl 5-bromo-4-chloro-3-indolyl phosphate 4-toluidine salt (Roth, dissolved at 50 µg/ml in DMF) and 5 µl nitro blue tetrazolium (Roth, 75 µg/ml in 70% v/v DMF) were added, until distinct colour signals could be recognized at the positions of some of the colonies.

Five of the colonies giving rise to the most intense colour spots on the hydrophobic membrane were cultured from the hydrophilic membrane. Their plasmid DNA was isolated and the BBP gene cassette was subjected to sequence analysis by means of an automated Genetic Analyzer system according to the instructions of the manufacturer using the oligodeoxynucleotide SEQ ID NO: 14 as primer as described in Example 4. The five sequenced clones carried functional inserts with different nucleotide sequences and were named CD154-13-10-1, CD154-13-10-2, CD154-13-10-3, CD154-13-10-4 and CD154-13-10-5.

The nucleotide sequences of the clones were translated into their amino acid sequence and those amino acid residues which deviate from the original BBP protein are given in Table 6. The sequencing revealed an amber stop codon, which was suppressed in the employed E. coli strains and translated into Gln, at position 93 in two of the selected variants. The nucleotide and amino acid sequences of the CD154 muteins CD154-13-10-1, CD154-13-10-2, CD154-13-10-1, CD154-13-10-4 and CD154-13-10-5 are also given in the sequence listing as SEQ ID NOS: 28 (nucleotide sequence) and SEQ ID NO: 60 (amino acid sequence), SEQ ID NOS: 29 (nucleotide sequence) and SEQ ID NO: 61 (amino acid sequence), SEQ ID NOS: 30 (nucleotide sequence) and SEQ ID NO: 62 (amino acid sequence), SEQ ID NOS: 31 (nucleotide sequence) and SEQ ID NO: 63 (amino acid sequence) and SEQ ID NOS: 32 (nucleotide sequence) and SEQ ID NO: 64 (amino acid sequence).

TABLE 6

Sequence characteristics of selected BBP muteins with specificity for CD154

| Pos. | BBP | CD154-13-10-1 | CD154-13-10-2 | CD154-13-10-3 | CD154-13-10-4 | CD154-13-10-5 |
|---|---|---|---|---|---|---|
| 35 | Ser | Gln | Gly | Trp | Ser | Val |
| 36 | Val | Ile | Thr | Leu | His | Thr |
| 38 | Lys | Gln | Glu | Leu | Thr | Ile |
| 39 | Tyr | Gly | Ser | Glu | Gly | Pro |
| 63 | His | Tyr | Thr | Met | Thr | Met |
| 64 | Gly | Ala | Gln | Gln | Pro | Ser |
| 65 | Lys | Ser | Gly | Gln | His | Phe |
| 67 | Tyr | Asp | Lys | Leu | Arg | Pro |

TABLE 6-continued

Sequence characteristics of selected BBP muteins with specificity for CD154

| Pos. | BBP | CD154-13-10-1 | CD154-13-10-2 | CD154-13-10-3 | CD154-13-10-4 | CD154-13-10-5 |
|---|---|---|---|---|---|---|
| 90 | Tyr | Ser | Arg | Val | Trp | Ser |
| 91 | Gly | Ser | Pro | Pro | Ile | Tyr |
| 93 | Val | Val | Leu | Gln* | Thr | Gln* |
| 116 | Lys | Gly | Asp | Phe | Ser | Glu |
| 118 | Asp | Arg | Met | Pro | Ser | Met |
| 120 | Asp | Ala | Cys | Asp | Ala | Ser |
| 121 | Lys | Pro | Lys | Ala | Gly | Ser |
| 125 | Gln | Met | Glu | Val | Gln | Lys |

*These glutamine residues were encoded by amber stop codons.

Example 16

Production of the BBP Muteins

The muteins CD154-13-10-1, CD154-13-10-3 and CD154-13-10-4 were selected for more detailed binding analyses and produced in preparative scale. CD154-13-10-1 and CD154-13-10-4 obtained from Example 15 were encoded on the vector pBBP41 with an amber stop codon between the STREP-TAG® II and the albumin binding domain. Therefore, these constructs were directly suited for subsequent preparative production and affinity testing after transformation of the non-supressor strain E. coli JM83 with the respective plasmids.

For the preparative production of the mutein CD154-13-10-3 also obtained from Example 15 the mutagenized coding region between the two BstXI cleavage sites was subcloned from the vector pBBP41 on the expression plasmid pBBP46 as described under Example 4. Due to an internal amber stop codon this BBP mutein was produced in E. coli-TG1F⁻ which was transformed with the resulting plasmid.

Single colonies of E. coli JM83 transformed with the pBBP41 plasmid coding for the BBP muteins CD154-13-10-1 and CD154-13-10-4 as well as single colonies of E. coli-TG1F⁻ transformed with the pBBP46 plasmids coding for the BBP mutein CD154-10-3 were used for inoculating each 100 ml of LB/Amp-medium, followed by incubation overnight at 37° C., 160 rpm. 2 l of LB/Amp-medium in a 5 l-Erlenmeyer flask were inoculated with 40 ml of this preculture and were shaken at 26° C., 160 rpm to an $OD_{550}$=0.4. Then the temperature was lowered to 22° C. and production of the recombinant protein was induced at an $OD_{550}$ of 0.5 by adding 200 µg/l anhydrotetracycline followed by shaking for 3 further hours at 22° C. at 160 rpm.

Harvesting of the bacterial cells and purification of the recombinant proteins was performed as described under Example 2. The protein yield for each of the BBP muteins was approximately 30-100 µg per 1 l culture.

Example 17

Measurement of the Affinity of the BBP Muteins for CD154 in ELISA

For the determination of affinity constants of the BBP muteins from Example 16 for the prescribed protein target CD154 in an ELISA the wells of a black Fluotrac 600 microtiter plate (Greiner; 384 well) were filled each with 20 µl of a solution of CD154 (DPC Biermann) or the unrelated control protein BSA at a concentration of 10 µg/ml in PBS and were incubated for 1 h at ambient temperature. After washing five times with 100 µl PBST/0.05 per well employing an automated ELISA plate washer, the wells were filled with 100 µl PBST containing 3% w/v non-fat dry milk powder (Vitalia), in order to saturate unspecific binding sites and incubated for one hour at room temperature. After blocking, the microtiter plate was washed two times with 100 µl PBST/0.05 as described above.

Then a dilution series of the muteins from Example 16 in SA-buffer was prepared in PBST starting from 2000 nM concentration and incubated for 1 h at room temperature. Subsequently, plates were washed again five times like above and 20 µl of an anti STREP-TAG® II monoclonal antibody-HRP-conjugate (IBA), diluted 1:1000 in PBST was added to each well and incubated for 1 hour at room temperature. Plates were again washed five times as described above and 20 µl of the fluorogenic HRP-substrate QUANTABLU™ (diluted as described by the manufacturer) was added to detect bound BBP muteins by means of the attached anti STREP-TAG® II monoclonal antibody-HRP-conjugate. After 10 minutes at room temperature fluorescence was excited at a wavelength of 320 nm (±12.5 nm) and measured at 430 nm (±17.5 nm) in a GENiosPlus plate reader.

The resulting binding curves were fitted by non-linear least squares regression as described in Example 8 and are depicted in FIG. 11. The values obtained for the apparent dissociation constants of the complexes between the BBP muteins and the prescribed target CD154 are summarized in Table 7.

TABLE 7

| Affinity binding constants between the BBP muteins and CD154 | | |
|---|---|---|
| BBP mutein | $K_D$ [nM] CD154 | $K_D$ [nM] BSA |
| CD154-13-10-1 | 89 ± 5.4 | —* |
| CD154-13-10-3 | 51 ± 7.2 | —* |
| CD154-13-10-4 | 174 ± 25 | —* |

*No detectable binding activity

Example 18

Production and Purification of the Extracellular Domains of the Human CD4 Coreceptor For the production of different extracellular domains of the human CD4 coreceptor as target proteins for the isolation of CD4-specific BBP muteins, cells of the *E. coli* strain JM83 were transformed with the expression plasmids pASK75-strepII-CD4V, pASK75-strepII-CD4D1 or pASK75-strepII-CD4VD1 (FIG. 12), respectively, harbouring the cDNAs coding for the extracellular CD4 V-domain (CD4-V), CD4 D1-domain (CD4-D1), or a fusion construct made of the CD4 V-domain and the CD4 D1-domain (CD4-VD1). For the cDNA of CD4 as well as the nomenclature of the respective domains, see Maddon et al., Cell 42 (1) (1985), 93-104.

100 ml of LB/Amp was inoculated with a single colony of the JM83 transformant carrying the respective plasmid, and incubated overnight at 37° C., 160 rpm. 2 l of LB/Amp-medium in a 5 l-Erlenmeyer flask were then inoculated with 40 ml of this preculture and were shaken at 26° C., 160 rpm. For the expression of the CD4 V-domain or CD4 D1-domain the temperature of the expression culture was lowered to 22° C. at an $OD_{550}$=0.4 and subsequently production of the recombinant protein was induced at an $OD_{550}$=0.5 by adding 200 µg/l anhydrotetracycline followed by shaking for 3-4 further hours at 22° C. and 160 rpm. For the expression of the fusion protein CD4-VD1 the temperature was lowered to 22° C. at an $OD_{550}$=0.5 and production of the recombinant protein was induced by adding 200 μg/l anhydrotetracycline followed by shaking for 6 further hours at 22° C. and 160 rpm.

Harvesting of the bacterial cells and purification of the recombinant proteins was performed as described under Example 2. The protein yield was approximately 40 μg per 1 l culture for expression of the CD4 V-domain, 300-400 μg for the CD4 D1-domain and 130 μg for the fusion protein CD4-VD1.

Example 19

Selection of BBP Muteins Against the Domain CD4-D1 of the Human CD4 Coreceptor Employing Polystyrol Multiwell Plates A 2 ml aliquot of the precipitated phagemids from Example 13 was centrifuged (20 minutes, 21460 g, 4° C.), the supernatant was removed, and the sedimented phagemid particles were dissolved in 750 μl PBS containing 50 mM benzamidine. After incubation for 30 minutes on ice the solution was centrifuged (5 minutes, 21460 g, 4° C.) to remove residual aggregates and for blocking of non-specific binding sites on the phagemid surface the supernatant was mixed with 750 μl PBST containing 5% w/v skimmed milk powder (Marvel) and incubated at room temperature for 30 minutes.

High binding polystyrol microtiter plates (Greiner) were used for the affinity enrichment of the recombinant phagemids carrying the BBP mutein fusion proteins. Five wells were coated overnight at 4° C. with each 300 μl of the CD4 D1-domain produced as described in Example 18 at a concentration of 50 μg/ml in PBS. Unoccupied binding sites on the surface of the wells were saturated by incubation with 350 μl per well 5% w/v skimmed milk powder in PBS for 2 hours at room temperature under shaking at 600 rpm on a Titramax 1000 shaker followed by three brief washes by incubation with 350 μl PBST per well for 2 min at room temperature, 600 rpm and subsequent removal of the buffer. Afterwards, each well was incubated with 300 μl of the blocked phagemid solution from above (ca. $1.6 \cdot 10^{12}$ cfu per well; $8 \cdot 10^{12}$ cfu in total) for 2 hours at room temperature.

For the removal of unbound phagemids, washing was performed eight times as described above, each time with 350 μl PBST per well for 2 minutes. Adsorbed phagemids were finally eluted by 10 minute treatment of the microtiter plate with 300 μl 0.1 M glycine/HCl pH 2.2 per respective well, followed by immediate neutralisation of the pH of each elution fraction by mixing it with 50 μl 0.5 M Tris.

For the amplification, the combined phagemid solution (containing between $10^5$ and $10^8$ cfu, depending on the selection cycle) was shortly warmed to 37° C., mixed with 5 ml of an exponentially growing culture of *E. coli* XL1-blue ($OD_{550}$=0.5), and incubated for 30 minutes at 37° C., 140 rpm. The cells infected with the phagemids were subsequently sedimented (2 minutes, 4420 g, 4° C.), resuspended in 600 μl of the culture medium, and plated out onto three LB/Amp agar plates (145 mm diameter).

After incubation for 14 hours at 32° C., the cells were scraped from the agar plates and for the repeated production and affinity enrichment of phagemid particles 25 ml of 2×YT/Amp were inoculated to an $OD_{550}$ of ca. 0.08 with an appropriate volume of this suspension and incubated at 37° C., 160 rpm until $OD_{550}$ reached 0.5.

After infection with VCS-M13 helper phage (Stratagene) at a moi of approximately 10 the culture was shaken for additional 45 minutes at 37° C., 140 rpm. Kanamycin (70 μg/ml) was subsequently added, the incubator temperature was lowered to 26° C. and, after 10 minutes, anhydrotetracycline was added at 25 μg/l (3.1 μl of a 0.2 mg/ml stock solution in DMF) in order to induce gene expression. Incubation continued for another 12-15 hours at 26° C., 140 rpm.

The cells were sedimented by centrifugation (15 minutes, 12100 g, 4° C.) and the supernatant containing the phagemid particles was sterile-filtered (0.45 μm), mixed with ¼ volume (6.3 ml) 20% w/v PEG 8000, 15% w/v NaCl, and incubated on ice for 30-60 minutes. After centrifugation (20 minutes, 18000 g, 4° C.) the precipitated phagemid particles were dissolved in 2 ml of cold BBS/E. The solution was distributed to two 1.5 ml reaction vessels and incubated on ice for 30 minutes. After centrifugation of undissolved components (5 minutes, 21460 g, 4° C.) each supernatant was transferred to a new reaction vessel.

Mixture with ¼ volume 20% w/v PEG 8000, 15% w/v NaCl and incubation for 30 to 60 minutes on ice served to reprecipitate the phagemid particles. After centrifugation (20 minutes, 21460 g, 4° C.) the supernatant was removed and the precipitated phagemid particles were dissolved and combined in a total of 1 ml PBS containing 50 mM benzamidine. After incubation for 30 minutes on ice the solution was centrifuged (5 minutes, 21460 g, 4° C.) in order to remove residual aggregates. For blocking of non-specific binding sites on the phagemid surface the supernatant was subsequently mixed with 1 ml PBST containing 5% w/v skimmed milk powder (Marvel) and incubated for 30 minutes at room temperature prior to utilization in the subsequent selection round.

Three further selection cycles against the CD4 D1-domain were carried out in this way employing the amplified and blocked phagemids from the respective previous enrichment cycle containing between $5 \cdot 10^{10}$ and $2 \cdot 10^{12}$ cfu/ml with the exception that beginning with the second enrichment cycle only three wells of a high binding microtiter plate were coated with CD4-D1 and that incubation of the phagemids with the immobilized target protein was allowed for 1 h instead of 2 h at ambient temperature.

Example 20

Identification of CD4-D1 Binding BBP Muteins by Use of the "Colony Screening" Method For the analytical production of the BBP muteins as fusion proteins with the STREP-TAG® II and the albumin binding domain and their characterization by colony screening, the gene cassette between the two BstXI cleavage sites was subcloned from the phagemid vector pBBP42 on pBBP41 as described in Example 15. The ligation mixture was used for transformation of *E. coli* TG1-F yielding 1.0 ml of a cell suspension which was subsequently stored at −80° C. after adding ¼ volume 80% v/v glycerol.

A hydrophilic PVDF membrane (Millipore, type GVWP, pore size 0.22 μm), labelled at one position and cut to size, was laid onto an LB/Amp agar plate. An appropriate volume of the glycerol stock of the transformation batch described above was uniformly plated onto this membrane in order to yield ca. 400-500 transformants. The agar plate was incubated for 7.5 hours at 37° C. until the colonies had reached a size of approximately 0.5 mm.

In the meantime, a hydrophobic membrane (Millipore, Immobilon P, pore size 0.45 μm), also cut to size, was moistened with water according to the instructions of the manufacturer. It was subsequently agitated for 4 hours at room temperature in 10 ml of a solution of 10 mg/ml human serum albumin (HSA, Sigma) in PBS. Remaining binding sites on the membrane were saturated by incubation with 15 ml PBST/0.05 containing 3% w/v BSA for 2 hours at room temperature. The membrane was washed twice for 10 minutes with 20 ml PBS and immersed afterwards for 10 minutes in 10 ml LB/Amp medium, to which 200 µg/l anhydrotetracycline was added. It was subsequently marked at one position and laid onto a culture plate with LB/Amp agar, which additionally contained 200 µg/l anhydrotetracycline. The hydrophilic membrane from above, on which the colonies were grown, was laid onto the hydrophobic membrane in such a way that both marks superimposed. The culture plate was incubated with the stack of both membranes at 22° C. for 15 hours. During this phase the respective BBP muteins were secreted from the colonies on the upper membrane and were immobilized via their albumin-binding domain on the HSA at the lower membrane.

After this, the upper membrane with the colonies was transferred to a fresh LB/Amp agar plate and stored at 4° C. The hydrophobic membrane was removed and washed three times for 5 minutes each with 20 ml PBST. For analysis of the binding activity of the immobilized BBP muteins, the hydrophobic membrane was incubated for 1 hour in 5 ml of a solution of a conjugate (100 nM) of CD4-D1 and digoxigenin in PBS. The conjugate was prepared by reacting CD4-D1 (produced as described in Example 18) at a twofold molar ratio of DIG-NHS (Roche) according to the instructions of the manufacturer. Excess reactant was removed from the CD4-D1-conjugate by means of size exclusion chromatography as described in Example 4.

After incubation with the conjugate, the membrane was washed three times with PBST, followed by incubation for 1 hour with 5 ml anti-digoxigenin Fab-alkaline-phosphatase conjugate (Roche) diluted 1:1000 in PBST to detect bound CD4-D1 by means of the attached digoxigenin groups. The membrane was washed twice with PBST and twice with PBS, each for 5 minutes, and agitated for 10 minutes in AP-buffer (0.1 M Tris/HCl pH 8.8, 0.1 M NaCl, 5 mM $MgCl_2$). For the chromogenic reaction, the membrane was incubated in 10 ml AP-buffer, to which 30 µl 5-bromo-4-chloro-3-indolyl phosphate 4-toluidine salt (Roth, dissolved at 50 µg/ml in DMF) and 5 µl nitro blue tetrazolium (Roth, 75 µg/ml in 70% v/v DMF) were added, until distinct colour signals could be recognized at the positions of some of the colonies.

10 colonies giving rise to the most intense colour spots on the hydrophobic membrane were cultured from the hydrophilic membrane. Their plasmid DNA was isolated and the BBP gene cassette was subjected to sequence analysis by means of an automated Genetic Analyzer system according to the instructions of the manufacturer using the oligodeoxynucleotide SEQ ID NO: 14 as primer as described in Example 4. One of the clones carried a functional insert and was named CD4-13-F4-10. The nucleotide sequence of the clone was translated into its amino acid sequence and those amino acid residues which deviate from the original BBP protein are given in Table 8. The sequencing revealed an amber stop codon, which was suppressed in the employed E. coli strains and translated to Gln, at positions 38 of the selected variant. The nucleotide and amino acid sequences of the BBP mutein CD4-13-F4-10 is also given as SEQ ID NOS: 33 (nucleotide sequence) and SEQ ID NO: 65 (amino acid sequence) in the sequence listing.

TABLE 8

Sequence characteristics of selected BBP muteins with specificity for the domain CD4-D1 of human CD4

| Pos. | BBP | CD4-13-F4-10 |
| --- | --- | --- |
| 35 | Ser | Pro |
| 36 | Val | Glu |
| 38 | Lys | Gln* |
| 39 | Tyr | Glu |
| 63 | His | Thr |
| 64 | Gly | Thr |
| 65 | Lys | Ala |
| 67 | Tyr | Asn |
| 90 | Tyr | Trp |
| 91 | Gly | Arg |
| 93 | Val | Ile |
| 116 | Lys | Ser |
| 118 | Asp | Arg |
| 120 | Asp | Trp |
| 121 | Lys | Phe |
| 125 | Gln | Phe |

*These glutamine residues were encoded by amber stop codons.

Example 21

Production of the BBP Mutein

For the preparative production of the mutein CD4-13-F4-10 obtained from Example 20 the mutagenized coding region between the two BstXI cleavage sites was subcloned from the vector pBBP41 on the expression plasmid pBBP46 as described under Example 4. The plasmid thus obtained encoded a fusion protein of the mutein with the OmpA signal sequence and the T7-tag at the N-terminus, and the STREP-TAG® II at the C-terminus. Due to an internal amber stop codon this BBP mutein was produced in E. coli-TG1F⁻ which was transformed with the respective plasmid.

A single colony of E. coli-TG1F⁻ transformed with the pBBP46 plasmids coding for the BBP mutein CD4-13-F4-10 was used for inoculating 100 ml of LB/Amp-medium, followed by incubation overnight at 37° C., 160 rpm. 2 l of LB/Amp-medium in a 5 l-Erlenmeyer flask were inoculated with 40 ml of this preculture and were shaken at 26° C., 160 rpm to an $OD_{550}$=0.4. Then the temperature was lowered to 22° C. and production of the recombinant protein was induced at an $OD_{550}$ of 0.5 by adding 200 µg/l anhydrotetracycline followed by shaking for 3 further hours at 22° C. at 160 rpm. Harvesting of the bacterial cells and purification of the recombinant proteins was performed as described under Example 2 and yielded approximately 100 µg of the recombinant BBP mutein per liter culture medium.

Example 22

Measurement of the Affinity of the BBP Mutein for the Domain CD4-D1 of Human CD4 in ELISA For the determination of the affinity constant of the mutein CD4-13-F4-10 from Example 21 for the CD4-D1 in an ELISA, the wells of a black Fluotrac 600 microtiter plate (Greiner; 384 well) were filled each with 20 µl of a solution of the recombinant BBP mutein at a concentration of 50 µg/ml in PBS and were incubated for 1 h at ambient temperature. After washing five times with 100 µl PBST/0.05 per well employing an automated ELISA plate washer, the wells were filled with 100 µl PBST containing 3% w/v non-fat dry milk powder (Vitalia), in order to saturate unspecific binding sites and incubated for one hour at room temperature. After blocking, the microtiter plate was washed two times with 100 μL PBST/ 0.05 as described above.

Then a dilution series of the prescribed recombinant protein target CD4-D1 (produced as described in Example 18) or the unrelated control protein RNaseB (Sigma), both conjugated with digoxigenin, was prepared in PBST starting from 2000 nM concentration and incubated for 1 h at room temperature. The conjugate of CD4-D1 was prepared as described in Example 20. The conjugate of RNaseB and digoxigenin was prepared by reacting RNaseB at a twofold molar ratio of DIG-NHS (Roche) according to the instructions of the manufacturer. Excess reactant was removed from the RNaseB-conjugate by means of size exclusion chromatography as described in Example 4.

After the incubation with the digoxigenin conjugates, plates were washed five times like above and 20 μl of an anti-digoxigenin-Fab-fragment-alkaline phosphatase-conjugate (Roche), diluted 1:1000 in PBST was added to each well and incubated for 1 hour at room temperature. Plates were washed five times and 20 μl of the fluorogenic substrate AttoPhos (Roche; prepared as described by the manufacturer) was added to detect bound CD4-D1 by means of the attached digoxigenin groups. After 10 minutes at room temperature fluorescence was excited at a wavelength of 430 nm (±17.5 nm) and measured at 535 nm (±12.5 nm) in a GENiosPlus plate reader.

Figure 13:
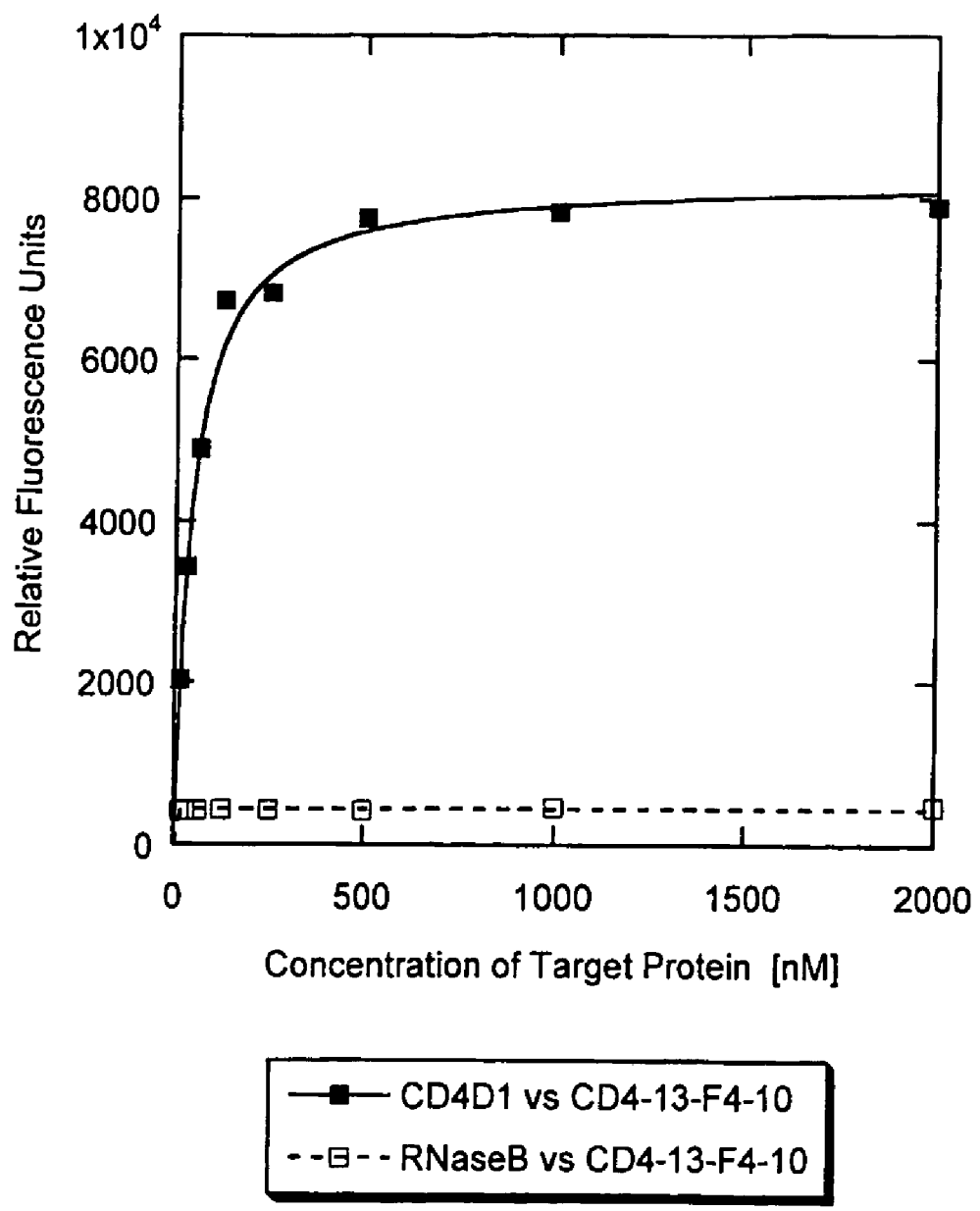
FIG. 13 depicts the binding of the BBP mutein CD4-13-F4-10 to CD4-VD1 and CD4-D1, respectively, in an ELISA.

The resulting binding curves were fitted by non-linear least squares regression as described in Example 8 and are depicted in FIG. 13. The value obtained for the apparent dissociation constant of the complex between the BBP mutein CD4-13-F4-10 and the prescribed target CD4-D1 are shown in Table 9.

TABLE 9

Affinity binding constants between the BBP mutein CD4-13-F4-10 and CD4-D1

| BBP mutein | $K_D$ [nM] CD4-D1 | $K_D$ [nM] RNaseB |
|---|---|---|
| CD4-13-F4-10 | 41 ± 4.2 | —* |

*No detectable binding activity

Example 23

Selection of BBP Muteins Against the Domain CD4-V of the Human CD4 Coreceptor Using Paramagnetic Beads The domain CD4-V of the human CD4 protein was conjugated with biotin groups and used as a target for affinity enrichment from the library of phagemids representing the BBP muteins together with streptavidin-coated paramagnetic particles (Dynal). The conjugate was prepared by reacting CD4-V (produced as described in Example 18) at a twofold molar ratio of sulfosuccinimidyl-2-(biotinamido)ethyl-1,3-dithiopropionate (Sulfo-NHS-SS-Biotin, Pierce) according to the instructions of the manufacturer. Excess reactant was removed from the CD4-V-conjugate by means of size exclusion chromatography as described in Example 4.

For the isolation of phagemids displaying a BBP mutein with affinity for CD4-V two different selection experiments were performed in parallel differing in the protocol for the blocking of non-specific binding sites on the surface of the employed phagemids. Therefore, two 2 ml aliquots of the precipitated phagemids obtained as described in Example 1 (about $10^{13}$ cfu) were centrifuged (20 minutes, 21460 g, 4° C.) and the supernatant was removed.

One aliquot of the sedimented phagemid particles was dissolved in 240 μl PBS, incubated for 30 minutes on ice and finally centrifuged (5 minutes, 21460 g, 4° C.) to remove residual aggregates. The phagemid containing supernatant was blocked by addition of 240 μl Chemiblocker (Chemicon) for 30 minutes at room temperature. At the same time, 90 μl of a 0.7 μM solution of biotinylated CD4-V from above was mixed with an equal volume of Chemiblocker and incubated for 30 minutes at room temperature. Subsequently the blocked phagemid solution (480 μl in total) was mixed with this blocked solution of biotinylatd CD4-V and incubated at room temperature for 1 h at 400 rpm in a Thermomixer (Eppendorf) so that complex formation between the recombinant protein and the muteins presented by the phagemids was able to occur.

The second aliquot of the sedimented phagemid particles was dissolved in 540 μl PBS, incubated for 30 minutes on ice and finally centrifuged (5 minutes, 21460 g, 4° C.) to remove residual aggregates. The phagemid containing supernatant was mixed with 90 μl of a 0.7 μM solution of biotinylated CD4-V from above and incubated at room temperature for 1 h at 400 rpm in a Thermomixer so that complex formation between the recombinant protein and the muteins presented by the phagemids was able to occur. Then, 200 μl of a solution of 8% w/v BSA, 0.4% v/v Tween 20 in PBS was added for blocking.

Parallel thereto, each 200 μl of a commercially available suspension of streptavidin-paramagnetic particles (Dynal) was washed three times with 200 μl PBS in two different wells of a 96-well Deepwell plate (Nunc) and prepared for the two different selection experiments. Herein, the particles were kept suspended for 1 min by shaking for 2 min at ambient temperature and 400 rpm like above, were then collected at the wall of the deep well plate with the aid of a 24-pin magnetic separator (Promega), and the supernatant was stripped off. In order to saturate unspecific binding sites, the paramagnetic particles were subsequently incubated with either 200 μl 50% v/v Chemiblocker in PBST or 200 μl PBST containing 2% w/v BSA at room temperature for 1 h at 400 rpm, respectively.

After removing the supernatants as above, the mixture of biotinylated CD4-V and the phagemids blocked with chemiblocker was added to the paramagnetic particles which had been blocked with the same reagent. The mixture to which the solution of BSA and Tween had been added was mixed with the particles that had been blocked with BSA. Subsequently, the particles were resuspended and incubated for 20 min at room temperature and 400 rpm.

Unbound phagemids were removed by washing the paramagnetic particles six times for 1 min at room temperature and 1000 rpm with 1 ml PBST and two times for 1 min with 1 ml PBS. Each time the particles were collected with the aid of the magnet and the supernatant was stripped off. Finally, the bound phagemids were eluted under reducing conditions in order to break up the disulfide bond contained in the linker molecule between CD4-V and the attached biotin group by resuspending the particles in 150 μl PBS containing 100 mM DTT and incubation for 20 minutes at room temperature and 1000 rpm. The particles were collected, the supernatant was stripped of and combined with the supernatant of a second elution step, which was performed in the same manner.

For the purpose of amplification, the eluted phagemid solution of both selection experiments (each 300 μl, containing between $10^6$ and $10^8$ cfu, depending on the selection cycle) was shortly warmed to 37° C., mixed with 3 ml each of an exponentially growing culture of *E. coli* XL1-blue ($OD_{550}$=0.5), and incubated for 30 minutes at 37° C., 140 rpm. The cells infected with the phagemids were subsequently sedimented (2 minutes, 4420 g, 4° C.), resuspended in 600 µl of the culture medium, and plated out each onto three agar plates with LB/Amp-medium (LB/Amp agar; 145 mm diameter)

After incubation for 14 hours at 32° C., the cells were scraped from the agar plates, each with addition of 10 ml 2×YT/Amp, were transferred to separate sterile Erlenmeyer-flasks (one flask for each selection experiment), and were shaken for 30 minutes at 37° C., 140 rpm for complete suspension. For the repeated production and affinity enrichment of phagemid particles two cultures with 25 ml of 2×YT/Amp were inoculated to an $OD_{550}$ of ca. 0.08 with an appropriate volume of each of the two obtained suspensions and incubated at 37° C., 160 rpm until the $OD_{550}$ reached 0.5.

After infection with VCS-M13 helper phage (Stratagene) at a moi of approximately 10 the cultures were shaken for additional 30 minutes at 37° C., 140 rpm. Kanamycin (70 µg/ml) was subsequently added, the incubator temperature was lowered to 26° C. and, after 10 minutes, anhydrotetracycline was added at 25 µg/l (3.1 µl of a 0.2 mg/ml stock solution in DMF) in order to induce gene expression. Incubation continued for another 15 hours at 26° C., 140 rpm.

The cells of both cultures were sedimented by centrifugation (15 minutes, 12100 g, 4° C.) and the supernatant containing the phagemid particles was sterile-filtered (0.45 µm), mixed with ¼ volume (6.3 ml) 20% w/v PEG 8000, 15% w/v NaCl, and incubated on ice for 30-60 minutes.

After centrifugation (20 minutes, 18000 g, 4° C.) the precipitated phagemid particles were dissolved each in 1 ml of cold PBS and the solutions were incubated on ice for 15-30 minutes. After centrifugation of undissolved components (5 minutes, 21460 g, 4° C.) each supernatant was transferred to a new reaction vessel.

The phagemid particles were each reprecipitated by mixing with ¼ volume 20% w/v PEG 8000, 15% w/v NaCl, followed by incubation for 30-60 minutes on ice. After centrifugation (20 minutes, 21460 g, 4° C.) the supernatants were removed and the precipitated phagemid particles (between $10^{11}$ and $10^{12}$ cfu) were dissolved in PBS. Here, 240 µl PBS were used for dissolving for the selection experiment performed with phagemids treated with Chemiblocker and 540 µl PBS were applied for the enrichment cycles which were performed with BSA-blocked phagemid preparations. After incubation for 15-30 minutes on ice, the solution was centrifuged (5 minutes, 21460 g, 4° C.) in order to remove residual aggregates and used for the affinity enrichment as described above.

Two further selection cycles, each with CD4-V, were carried out in the way that phagemids eluted as a result of a selection round which was performed with a particular blocking reagent (Chemiblocker or BSA) were treated with the same blocking reagent in subsequent selection cycles.

Example 24

Selection of BBP Muteins Against the Fusion Protein CD4-VD1 of the Human CD4 Coreceptor Using Paramagnetic Beads The recombinant fusion protein consisting of the domains CD4-V and CD4-D1 of the human CD4 protein (CD4-VD1) was conjugated with biotin groups and used as a target for affinity enrichment from the library of phagemids representing the BBP muteins together with streptavidin-coated paramagnetic particles (Dynal). The conjugate was prepared by reacting CD4-VD1 (produced as described in Example 18) at a twofold molar ratio of Sulfo-NHS-SS-Biotin (Pierce) according to the instructions of the manufacturer. Excess reactant was removed from the CD4-VD1-conjugate by means of size exclusion chromatography as described in Example 4.

For the isolation of phagemids displaying a BBP mutein with affinity for CD4-VD1 one 2 ml aliquot of the precipitated phagemids obtained as described in Example 1 (ca. $10^{13}$ cfu) was centrifuged (20 minutes, 21460 g, 4° C.) and the supernatant was removed. The sedimented phagemid particles were dissolved in 540 µl PBS, incubated for 30 minutes on ice and finally centrifuged (5 minutes, 21460 g, 4° C.) to remove residual aggregates. The phagemid containing supernatant was mixed with 60 µl of a 1 µM solution of biotinylated CD4-VD1 from above and incubated at room temperature for 1 h at 400 rpm in a Thermomixer (Eppendorf) so that complex formation between the recombinant protein and the muteins presented by the phagemids was able to occur. Then, 200 µl of a solution of 8% w/v BSA, 0.4% v/v Tween 20 in PBS was added for blocking of non-specific binding sites on the surface of the applied phagemids.

Parallel thereto, 200 µl of a commercially available suspension of streptavidin-paramagnetic particles (Dynal) was washed three times with 200 µl PBS in a 96-well Deepwell plate (Nunc). Herein, the particles were kept suspended for 1 min by shaking for 2 min at ambient temperature and 400 rpm like above, were then collected at the wall of the deep well plate with the aid of a 24-pin magnetic separator (Promega), and the supernatant was stripped off. In order to saturate unspecific binding sites, the paramagnetic particles were subsequently incubated with 200 µl PBST containing 2% w/v BSA at room temperature for 1 h at 400 rpm.

After removing the supernatant as above, the mixture of biotinylated CD4-VD1 and the phagemids was added to the paramagnetic particles, the particles were resuspended and incubated for 20 min at room temperature and 400 rpm. Unbound phagemids were removed by washing the paramagnetic particles six times for 1 min at room temperature and 1000 rpm with 1 ml PBST and two times for 1 min with 1 ml PBS. Each time the particles were collected with the aid of the magnet and the supernatant was stripped off. Finally, the bound phagemids were eluted under reducing conditions in order to break up the disulfide bond contained in the linker molecule between CD4-VD1 and the attached biotin group by resuspending the particles in 150 µl PBS containing 100 mM DTT and incubation for 20 minutes at room temperature and 1000 rpm. The particles were collected, the supernatant was stripped of and combined with the supernatant of a second elution step, which was performed in the same manner.

For the purpose of amplification, the eluted phagemid solution (300 µl, containing between $10^6$ and $10^8$ cfu, depending on the selection cycle) was shortly warmed to 37° C., mixed with 3 ml of an exponentially growing culture of *E. coli* XL1-blue ($OD_{550}$=0.5), and incubated for 30 minutes at 37° C., 140 rpm. The cells infected with the phagemids were subsequently sedimented (2 minutes, 4420 g, 4° C.), resuspended in 600 µl of the culture medium, and plated out onto three agar plates with LB/Amp-medium (LB/Amp agar; 145 mm diameter)

After incubation for 14 hours at 32° C., the cells were scraped from the agar plates, each with addition of 10 ml 2×YT/Amp, were transferred to a sterile Erlenmeyer-flask, and were shaken for 30 minutes at 37° C., 140 rpm for complete suspension. For the repeated production and affinity enrichment of phagemid particles 25 ml of 2×YT/Amp were inoculated to an OD$_{550}$ of ca. 0.08 with an appropriate volume of the obtained suspension and incubated at 37° C., 160 rpm until the OD$_{550}$ reached 0.5.

After infection with VCS-M13 helper phage (Stratagene) at a moi of approximately 10 the culture was shaken for additional 30 minutes at 37° C., 140 rpm. Kanamycin (70 µg/ml) was subsequently added, the incubator temperature was lowered to 26° C. and, after 10 minutes, anhydrotetracycline was added at 25 µg/l (3.1 µl of a 0.2 mg/ml stock solution in DMF) in order to induce gene expression. Incubation continued for another 15 hours at 26° C., 140 rpm.

The cells were sedimented by centrifugation (15 minutes, 12100 g, 4° C.) and the supernatant containing the phagemid particles was sterile-filtered (0.45 µm), mixed with ¼ volume (6.3 ml) 20% w/v PEG 8000, 15% w/v NaCl, and incubated on ice for 30-60 minutes. After centrifugation (20 minutes, 18000 g, 4° C.) the precipitated phagemid particles were dissolved in 1 ml of cold PBS and the solution was incubated on ice for 15-30 minutes. After centrifugation of undissolved components (5 minutes, 21460 g, 4° C.) the supernatant was transferred to a new reaction vessel.

The phagemid particles were reprecipitated by mixing with ¼ volume 20% w/v PEG 8000, 15 % w/v NaCl, followed by incubation for 30-60 minutes on ice. After centrifugation (20 minutes, 21460 g, 4° C.) the supernatant was removed and the precipitated phagemid particles (between $10^{11}$ and $10^{12}$ cfu) were dissolved in 540 µl PBS. After incubation for 15-30 minutes on ice, the solution was centrifuged (5 minutes, 21460 g, 4° C.) in order to remove residual aggregates and used for the affinity enrichment as described above. Two further selection cycles with CD4-VD1 were carried out in this way Example 25

Identification of CD4-VD1-Binding BBP Muteins by Use of an Automated Colony Screening Method For the analytical production of the BBP muteins obtained in Example 23 and Example 24 as fusion proteins with the STREP-TAG® II and the albumin-binding domain (ABD) and their characterization by colony screening, the gene cassette between the two BstXI cleavage sites was subcloned from the phagemid vector pBBP38 on the vector pBBP41 (FIG. 10).

For this purpose the phasmid DNA was isolated from the mixture of the E. coli clones obtained by infection with the phagemids either of the two selection experiments of Example 23 or of Example 24, eluted each as a result of the last selection cycle, using the Plasmid Miniprep Spin kit (Genomed). The DNA was cut with the restriction enzyme BstXI and the smaller of the two fragments (335 bp) was purified by preparative agarose gel electrophoresis as described in Example 1. The DNA of the vector pBBP41 was likewise cut with BstXI and the larger one of the two fragments (3548 bp) was isolated in the same way.

For the ligation, 50 fmol of the isolated small DNA-fragment was mixed with 50 fmol of the large DNA-fragment and incubated with 3 Weiss Units of T4 DNA ligase (Promega) in a total volume of 20 µl (30 mM Tris/HCl pH 7.8, 10 mM MgCl$_2$, 10 mM DTT, 1 mM ATP), followed by incubation overnight at 16° C. E. coli TG1-F$^-$ was transformed with 4 µl of this ligation mixture according to the CaCl$_2$-method, yielding 1.0 ml of a cell suspension which was subsequently stored at −80° C. after adding ¼ volume 80% v/v glycerol.

An appropriate volume of these glycerol stocks was uniformly plated onto LB/Amp-agar plates (22 cm×22 cm) in order to yield each ca. 1000 to 5000 transformants and was incubated at 32° C. for 16 hours until the colonies had reached a size of 0.5 mm to 2 mm.

A collection of 345 single E. coli colonies each from both selection experiments of Example 23 as well as 345 colonies from Example 24 was picked from such an agar plate into 70 µl per well 2×YT/Amp in flat bottom 384 well plates (Greiner) by means of an automated colony picker (Genetix) and grown overnight at 37° C. at 700 rpm on a benchtop shaker in a humidified incubator at 60% relative humidity (rH) as described in Example 4.

A hydrophilic PVDF membrane (Millipore, type GVWP, pore size 0.22 µm) labelled at two positions and cut to size (22 cm×22 cm), was laid onto an LB/Amp agar plate (22 cm×22 cm). The cultures from above were transferred in duplicates onto this membrane by means of a 384 pin head (Genetix) in a way that each 9 clones were spottet within a 3×3 grid of the size of 3 mm×3 mm. 384 of these 3×3 grids were equally distributed within a 16×24 grid which was in turn within a pattern of 7.3 cm×11 cm in size. Six of those patterns were spottet on the membrane within a 2×3 grid resulting in six identical patterns of E. coli clones on the 22 cm×22 cm membrane. The LB/Amp agar plate with the membrane on top was incubated for 3 hours at 37° C. until the colonies had reached a size of approximately 0.5 mm. The corresponding 384 well plates from which the clones had been transferred were kept as "master" plates at −80° C. after adding glycerol to a final concentration of 15% v/v to each well.

In the meantime, a hydrophobic membrane (Immobilon P), also cut to size (22 cm×22 cm), was moistened with water according to the instructions of the manufacturer and subsequently agitated for 4 hours at room temperature in 60 ml of a solution of 10 mg/ml HSA in PBS. Remaining binding sites on the membrane were saturated by incubation with 100 ml PBS containing 0.5% Tween 20 and 3% w/v BSA for 2 hours at room temperature. The membrane was washed twice for 10 minutes with 100 ml PBS and immersed afterwards for 10 minutes in 60 ml LB/Amp medium, which was supplemented with 200 µg/l anhydrotetracycline. It was subsequently marked at two positions and laid onto a culture plate with LB/Amp agar (22 cm×22 cm), which additionally contained 200 µg/l anhydrotetracycline. The hydrophilic membrane from above, on which the colonies were grown, was laid onto the hydrophobic membrane in such a way that the marks superimposed. The culture plate was incubated with the stack of both membranes at 22° C. for 15 hours. During this phase the respective BBP muteins were released from the colonies on the upper membrane and became immobilized via their albumin-binding domain to the HSA at the lower membrane.

After incubation, the hydrophilic membrane carrying the colonies was discarded and the hydrophobic membrane was cut into six equal pieces (7.3 cm×11 cm in size) corresponding to the patterns described above, each with the identical invisible replica of the immobilized BBP muteins. For binding analysis, the six hydrophobic membranes were washed three times for 5 minutes each with 20 ml PBST.

Then, five of the membranes were incubated, respectively, with 20 ml of conjugates of digoxigenin and either CD4-VD1 (produced as described in Example 18) or the unrelated control proteins RNaseB (Roche), transferrin (Roche), CD47 (produced as described in Example 2), a recombinantly produced extracellular domain of murine B7. 1 (Freeman et al., J. Exp. Med. 174 (1991), 625-631) carrying an N-terminal His6-tag (SEQ ID NO: 73), each at a concentration of 50 nM in PBS for 1 h. The conjugates were prepared by reacting the respective proteins at a twofold molar ratio of DIG-NHS (Roche) according to the instructions of the manufacturer. Excess reactant was removed from the conjugates as described in Example 4.

After incubation with the conjugate, each membrane was washed three times with 20 ml PBST, followed by incubation for 1 hour with 20 ml anti-digoxigenin Fab-alkaline-phosphatase conjugate (Roche), diluted 1:2000 in PBST, for the detection of bound CD4-VD1 or control proteins via their digoxigenin groups. Each membrane was washed twice with 20 ml PBST and twice with 20 ml PBS, each for 5 minutes, and agitated for 10 minutes in 20 ml AP-buffer (0.1 M Tris/HCl pH 8.8, 0.1 M NaCl, 5 mM $MgCl_2$). For the chromogenic reaction, the membranes were incubated in 20 ml AP-buffer, to which 60 µl 5-bromo-4-chloro-3-indolyl phosphate 4-toluidine salt (dissolved at 50 µg/ml in dimethylformamide) and 10 µl nitro blue tetrazolium (75 µg/ml in 70% v/v dimethylformamide) were added, until distinct colour signals could be recognized at the positions of some of the colonies.

The sixth membrane was incubated with 20 ml anti STREP-TAG® II monoclonal antibody-HRP-conjugate (IBA; 1:2000 in PBS containing 0.2% w/v BSA) for 1 h as a control in order to visualize immobilized BBP muteins on the hydrophobic membrane via their STREP-TAG® II affinity tag. Therefore, the membrane was washed twice with 20 ml PBST and twice with 20 ml PBS, each for 5 minutes. For the chromogenic reaction, the membrane was incubated in 15 ml 3,3'-diaminobenzidine solution (Vector Laboratories), prepared as described by the manufacturer, until distinct colour signals could be recognized at the positions of most of the colonies.

The membranes were washed with deionized water, digitized with a scanner (Agfa Snapscan) and analyzed with an automated image analyzer software (Raytest). 15 of 790 tested clones derived from Example 23 as well as 11 of 345 tested clones derived from Example 24 gave rise to intense color signals on the membrane probed with the conjugate of CD4-VD1 and digoxigenin but showed weak or no cross-reactivity on the unrelated control proteins. 6 clones from the former as well as 4 clones from the latter collection were cultured using the stored 384 well master plates, their plasmid DNA was isolated and and the BBP gene cassette was subjected to sequence analysis by means of an automated Genetic Analyzer system according to the instructions of the manufacturer using the oligodeoxynucleotide SEQ ID NO: 14 as primer as described in Example 4.

4 of the 6 clones obtained from Example 23 and 3 of the 4 clones from Example 24 carried a functional insert with different nucleotide sequences, indicating that multiple muteins were enriched during the selection procedure. This muteins were named CD4-2C3-K20, CD4-2C3-N22, CD4-2G3-H22, CD4-2G3-L22, and CD4-7B4-K21, CD4-7B4-K23, CD4-7B4-N14, respectively.

The nucleotide sequences of the clones were translated into their amino acid sequence and those amino acid residues which deviate from the original BBP protein are given in Table 10. The nucleotide sequences and the full amino acid sequences of the BBP muteins CD4-2C3-K20, CD4-2C3-N22, CD4-2G3-H22, CD4-2G3-L22, CD4-7B4-K21, CD4-7B4-K23, and CD4-7B4-N14 are also given as SEQ ID NOS: 34 (nucleotide sequence) and SEQ ID NO: 66 (amino acid sequence), SEQ ID NOS: 35 (nucleotide sequence) and SEQ ID NO: 67 (amino acid sequence), SEQ ID NOS: 36 (nucleotide sequence) and SEQ ID NO: 68 (amino acid sequence), SEQ ID NOS: 37 (nucleotide sequence) and SEQ ID NO: 69 (amino acid sequence), SEQ ID NOS: 38 (nucleotide sequence) and SEQ ID NO: 70 (amino acid sequence), SEQ ID NOS: 39 (nucleotide sequence) and SEQ ID NO: 71 (amino acid sequence), and SEQ ID NOS: 40 (nucleotide sequence) and SEQ ID NO: 72 (amino acid sequence).

TABLE 10

Sequence characteristics of selected BBP muteins with specificity for CD4-V or CD4-VD1

| Pos. | BBP | CD4-2C3-K20 | CD4-2C3-N22 | CD4-2G3-H22 | CD4-2G3-L22 | CD4-7B4-K21 | CD4-7B4-K23 | CD4-7B4-N14 |
|---|---|---|---|---|---|---|---|---|
| 35 | Ser | Thr | Ala | Met | Ile | Lys | Gly | Arg |
| 36 | Val | Ser | Lys | Thr | Ala | Lys | Asn | Ala |
| 38 | Lys | His | Ser | Val | Leu | Gly | Leu | Ile |
| 39 | Tyr | Ser | Pro | Lys | Gly | Arg | Arg | Gly |
| 63 | His | Lys | Gln | Arg | Asn | Thr | Asn | Lys |
| 64 | Gly | Lys | Arg | Glu | Trp | Gly | Thr | Gln |
| 65 | Lys | Lys | Leu | Lys | Asn | Asn | Ser | Trp |
| 67 | Tyr | Arg | Gly | Trp | Met | Ile | Gly | Lys |
| 75° | Pro | Ser | Pro | Pro | Pro | Pro | Pro | Pro |
| 76° | Val | Ala | Val | Val | Val | Val | Val | Val |
| 85° | Tyr | Tyr | Tyr | Tyr | Ser | Tyr | Tyr | Tyr |
| 90 | Tyr | Ser | Thr | Ile | Lys | Lys | Asn | Gly |
| 91 | Gly | Val | Trp | Ser | Val | Thr | Thr | Thr |
| 93 | Val | Lys | Leu | Leu | Gln | Ser | Met | Ser |
| 106° | Asn | Asn | Asn | Asp | Asn | Asn | Asn | Asn |
| 116 | Lys | Ser | Gly | Lys | Gln | Val | Ser | Asn |
| 117° | Tyr | Tyr | Tyr | Tyr | Tyr | Tyr | Trp | Tyr |
| 118 | Asp | Lys | Val | Met | Ser | Leu | Glu | His |
| 119° | Glu | Glu | Glu | Glu | Glu | Glu | Val | Glu |
| 120 | Asp | Lys | Lys | Leu | Arg | Tyr | Ser | Ser |
| 121 | Lys | Thr | Ser | Trp | Ala | Ser | Δ | Arg |
| 125 | Gln | Gly | Pro | Arg | Leu | Arg | His | Arg |

°These amino acid substitutions arose from accidental mutations outside the randomized positions.
ΔThis amino acid deletion arose due to an accidental mutation outside the randomized positions.

Example 26

Production of the BBP Muteins

The muteins CD4-2C3-K20, CD4-2C3-N22, CD4-2G3-H22, CD4-2G3-L22, CD4-7B4-K21, CD4-7B4-K23, and CD4-7B4-N14 obtained from Example 25 were encoded on the colony screening vector pBBP41 carrying an amber stop codon between the Strep-tag® II affinity tag and the albumin binding domain. Therefore, these constructs were directly suited for subsequent preparative production and affinity testing after transformation of the non-suppressor strain *E. coli* JM83 with the respective plasmids.

Single colonies of *E. coli* JM83 transformed with the pBBP41 plasmids coding for the BBP muteins CD4-2C3-K20, CD4-2C3-N22, CD4-2G3-H22, CD4-2G3-L22, CD4-7B4-K21, CD4-7B4-K23, and CD4-7B4-N14 were used for the production of the recombinant BBP muteins as described in Example 16.

Harvesting of the bacterial cells and purification of the recombinant proteins was performed as described under Example 2. The protein yield for each of the BBP muteins was approximately 50-150 µg per 1 l culture.

Example 27

Measurement of the Affinity of the BBP Muteins Selected in Example 23 and Example 24 for CD4-VD1 in ELISA For the determination of affinity constants of the BBP muteins selected against CD4-V (Example 23) as well as CD4-VD1 (Example 24) for CD4-VD1 in an ELISA, the wells of a black Fluotrac 600 microtiter plate (Greiner; 384 well) were filled each with 20 μl of a solution of the muteins from Example 26 at a concentration of 50 μg/ml in PBS-buffer and were incubated for 1 h at ambient temperature.

After washing five times with 100 μl PBST/0.05 per well employing an automated ELISA plate washer, the wells were filled with 100 μl PBST containing 3% w/v non-fat dry milk powder (Vitalia), in order to saturate unspecific binding sites and incubated for one hour at room temperature. After blocking, the microtiter plate was washed two times with 100 μl PBST/0.05 as described above.

Then a dilution series of conjugates of digoxigenin and either the prescribed protein target CD4-VD1 or the unrelated control protein RNaseB, both produced as described in Example 25, was prepared in PBST starting from 2000 nM concentration and incubated for 1 h at room temperature. Subsequently, plates were washed again five times like above and 20 μl of an anti-digoxigenin-Fab-fragment-alkaline phosphatase-conjugate (Roche), diluted 1:1000 in PBST was added to each well and incubated for 1 hour at room temperature. Plates were washed again five times as described above and 20 μl of the fluorogenic substrate AttoPhos (Roche; prepared as described by the manufacturer) was added to detect bound CD4-VD1 by means of the attached digoxigenin groups. After 10 minutes at room temperature fluorescence was excited at a wavelength of 430 nm (±17.5 nm) and measured at 535 nm (±12.5 nm) in a GENiosPlus plate reader.

Figure 14:
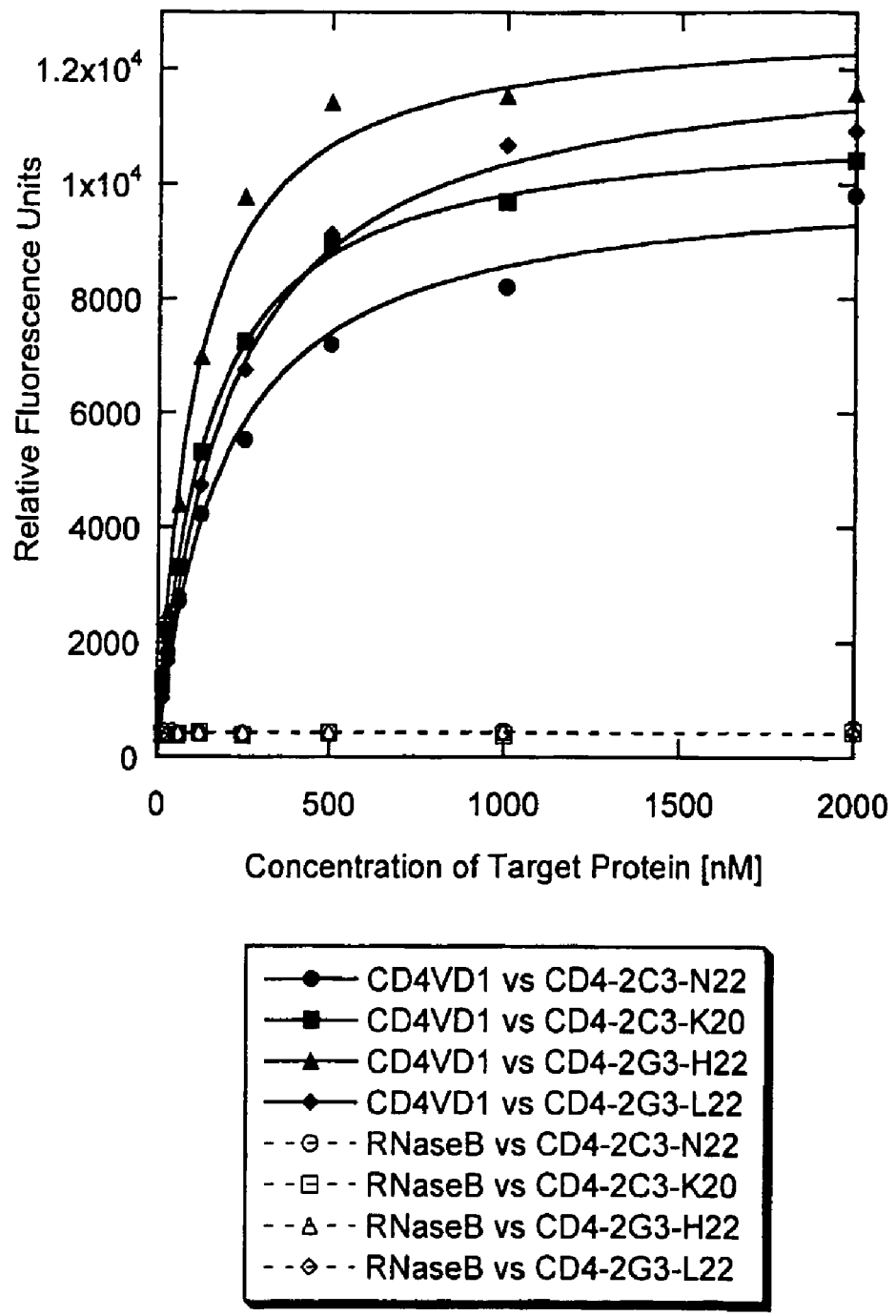
FIG. 14 depicts the binding of BBP muteins CD4-2C3-K20, CD4-2C3-N22, CD4-2G3-H22, CD4-2G3-L22 to CD4-VD1 in an ELISA.

The resulting binding curves were fitted by non-linear least squares regression as described in Example 8 and are depicted in FIG. 14 and FIG. 15. The values obtained for the apparent dissociation constants of the complexes between the BBP muteins CD4-2C3-K20, CD4-2C3-N22, CD4-2G3-H22, CD4-2G3-L22, CD4-7B4-K21, CD4-7B4-K23, and CD4-7B4-N14 and the prescribed target protein CD4-VD1 as well as for the complexes between the BBP muteins and the control protein RNaseB are summarized in Table 11.

TABLE 11

Affinity binding constants between the BBP muteins and CD4-VD1

| BBP mutein | $K_D$ [nM] CD4-VD1 | $K_D$ [nM] RNaseB |
|---|---|---|
| CD4-2C3-K20 | 136 ± 6.3 | —* |
| CD4-2C3-N22 | 185 ± 23.4 | —* |
| CD4-2G3-H22 | 105 ± 14.2 | —* |
| CD4-2G3-L22 | 200 ± 13.7 | —* |
| CD4-7B4-K21 | 105 ± 9.4 | —* |
| CD4-7B4-K23 | 169 ± 19.4 | —* |
| CD4-7B4-N14 | 177 ± 7.1 | —* |

*No detectable binding activity

What is claimed is:

1. A lipocalin mutein derived from the bilin-binding protein of *Pieris Brassicae*, wherein the mutein comprises at least 5-16 mutated amino acid residues with respect to the wild-type amino acid sequence and wherein said mutations are selected from the amino acid sequence positions corresponding to sequence positions 35, 36, 38, 63, 64, 65, 67, 90, 91, 93, 116, 118, 120, 121 and 125 of the full-length bilin-binding protein of *Pieris Brassicae* and said mutein binds a given target with detectable affinity.

2. The mutein of claim 1, comprising at least 6 mutated amino acid residues at any of the sequence positions corresponding to the sequence positions 38, 39, 63, 64, 65, 67, 91, 118, 120, and 121 of the linear polypeptide sequence of the bilin-binding protein of *Pieris brassicae*.

3. The mutein of claim 1 further comprising at least one mutated amino acid residue at any of the sequence positions corresponding to the sequence positions 35, 36, 90, 93, 116, and 125 of the linear polypeptide sequence of the bilin-binding protein of *Pieris brassicae*.

4. The mutein of claim 3 comprising at least 7 mutated amino acid residues at any of the sequence positions corresponding to the sequence positions 35, 36, 38, 39, 63, 64, 65, 67, 90, 91, 93, 116, 118, 120, 121, and 125 of the linear polypeptide sequence of the bilin-binding protein of *Pieris brassicae*.

5. The mutein of claim 4, wherein the mutein comprises mutated amino acid residues at least any 8 of said sequence positions.

6. The mutein of claim 4, wherein the mutein comprises mutated amino acid residues at least any 10 to 12 of said sequence positions.

7. The mutein of claim 4, wherein the mutein comprises mutated amino acid residues at all 16 of said sequence positions.

8. The mutein of claim 1, wherein the mutein binds a macromolecular target selected from the group consisting of proteinaceous molecules, nucleic acids, and carbohydrates.

9. The mutein of claim 8, wherein the mutein binds a proteinaceous molecule selected from the group consisting of a protein, a protein domain, and a peptide.

10. The mutein of claim 9, wherein the proteinaceous molecule is selected from the group consisting of CD47, ferritin, CD154, CD4, a fragment or a homologue thereof comprising at least 80% sequence homology.

11. The mutein of claim 9, wherein the mutein binds to CD47 or a fragment thereof.

12. The mutein of claim 11, wherein the mutein is selected from the group of muteins encoded by the nucleic acid sequences consisting of SEQ ID NO: 16, SEQ ID NO: 17, and SEQ ID NO: 18.

13. The mutein of claim 9, wherein the mutein binds to ferritin.

14. The mutein of claim 13, wherein the mutein is selected from the group of muteins encoded by the nucleic acid sequences consisting of SEQ ID NO: 19, SEQ ID NO: 20, SEQ ID NO: 21, SEQ ID NO: 22, SEQ ID NO: 23, and SEQ ID NO: 24.

15. The mutein of claim 9, wherein the mutein binds to CD154 or a fragment thereof.

16. The mutein of claim 15, wherein the mutein is selected from the group of muteins encoded by the nucleic acid sequences consisting of SEQ ID NO: 28, SEQ ID NO: 29, SEQ ID NO: 30, SEQ ID NO: 31, and SEQ ID NO: 32.

17. The mutein of claim 9, wherein the mutein binds to CD4 or a fragment thereof.

18. The mutein of claim 17, wherein the mutein is selected from the group of muteins encoded by the nucleic acid sequences consisting of SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

19. The mutein of claim 1, wherein the mutein is conjugated to a label selected from the group consisting of organic molecules, enzyme labels, radioactive labels, colored labels, fluorescent labels, chromogenic labels, luminescent labels, haptens, digoxigenin, biotin, metal complexes, metals, and colloidal gold.

20. The mutein of claim 1, wherein the mutein is fused at its N-terminus or its C-terminus to a protein, a protein domain or a peptide.

21. A pharmaceutical composition comprising at least one mutein of claim 1.

22. A method of binding/detection of a given target, comprising:
(a) contacting a mutein as defined in claim 1 with a test sample supposed to contain said target, and
(b) detecting the mutein/target complex by a suitable signal.

23. A method for separating a given target, comprising:
(a) contacting a mutein as defined in claim 1 with a sample supposed to contain said target, and
(b) separating the mutein/target complex from the sample.

24. The method of claim 22, wherein the mutein/target complex is bound onto a solid phase.

25. The method of claim 23, wherein the mutein/target complex is bound onto a solid phase.

26. A method for targeting a compound to a preselected site comprising
(a) contacting a mutein as defined in claim 1 with said compound, and
(b) delivering the mutein/compound complex to the preselected site.

* * * * *